US011872131B2

(12) United States Patent
Hariton et al.

(10) Patent No.: US 11,872,131 B2
(45) Date of Patent: Jan. 16, 2024

(54) PROSTHETIC VALVE AND DELIVERY TOOL THEREFOR

(71) Applicant: CARDIOVALVE LTD., Or Yehuda (IL)

(72) Inventors: Ilia Hariton, Zichron Yaackov (IL); Boaz Harari, Ganey Tikva (IL); Meni Iamberger, Kfar Saba (IL)

(73) Assignee: CARDIOVALVE LTD., Or Yehuda (IL)

( * ) Notice: Subject to any disclaimer, the term of this patent is extended or adjusted under 35 U.S.C. 154(b) by 37 days.

(21) Appl. No.: 17/839,538

(22) Filed: Jun. 14, 2022

(65) Prior Publication Data

US 2022/0338985 A1  Oct. 27, 2022

Related U.S. Application Data

(63) Continuation of application No. 16/768,909, filed as application No. PCT/IL2018/051350 on Dec. 12, 2018, now Pat. No. 11,382,746.

(30) Foreign Application Priority Data

Dec. 13, 2017  (GB) ...................................... 1720803

(51) Int. Cl.
*A61F 2/24*  (2006.01)

(52) U.S. Cl.
CPC .......... *A61F 2/2436* (2013.01); *A61F 2/2418* (2013.01); *A61F 2/2433* (2013.01);
(Continued)

(58) Field of Classification Search
CPC .... A61F 2/2436; A61F 2/2418; A61F 2/2433; A61F 2210/0014; A61F 2250/0048
See application file for complete search history.

(56) References Cited

U.S. PATENT DOCUMENTS

| 3,874,388 A | 4/1975 | King |
| 4,222,126 A | 9/1980 | Boretos |

(Continued)

FOREIGN PATENT DOCUMENTS

| CA | 2822801 | 8/2006 |
| CN | 103974674 | 8/2014 |

(Continued)

OTHER PUBLICATIONS

International Search Report and Written Opinion issued in App. No. PCT/IL2021/051433, dated May 3, 2022, 26 pages.

(Continued)

*Primary Examiner* — Suba Ganesan
(74) *Attorney, Agent, or Firm* — DILWORTH IP, LLC

(57) ABSTRACT

Embodiments of the present disclosure include a method for use at a native valve of a heart of a subject. At a distal portion of a delivery tool, a balloon is coupled to a shaft. The distal portion is advanced to the heart with an implant and the balloon disposed within a capsule. The implant includes a tubular frame and one or more shape-memory flanges. The tubular frame is compressed around the balloon, and the flanges are constrained within a downstream capsule-portion of the capsule. The flanges are exposed from the downstream capsule-portion such that the flanges automatically deflect radially outward. Subsequently, the flanges are pressed against a downstream surface of the native valve by moving the implant in an upstream direction. While the flanges are in contact with the downstream surface, the tubular frame is plastically expanded radially by inflating the balloon. Other embodiments are also described.

20 Claims, 21 Drawing Sheets

(52) U.S. Cl.
CPC ............... *A61F 2210/0014* (2013.01); *A61F 2250/0048* (2013.01); *A61F 2250/0063* (2013.01); *A61F 2250/0065* (2013.01)

(56) References Cited

U.S. PATENT DOCUMENTS

| | | | |
|---|---|---|---|
| 4,261,342 A | 4/1981 | Aranguren Duo | |
| 4,275,469 A | 6/1981 | Gabbay | |
| 4,340,091 A | 7/1982 | Skelton | |
| 4,423,525 A | 1/1984 | Vallana | |
| 4,853,986 A | 8/1989 | Allen | |
| 4,892,541 A | 1/1990 | Alonso | |
| 4,972,494 A | 11/1990 | White | |
| 4,994,077 A | 2/1991 | Dobben | |
| 5,078,739 A | 1/1992 | Martin | |
| 5,108,420 A | 4/1992 | Marks | |
| 5,201,757 A | 4/1993 | Heyn | |
| 5,314,473 A | 5/1994 | Godin | |
| 5,332,402 A | 7/1994 | Teitelbaum | |
| 5,397,351 A | 3/1995 | Pavcnik | |
| 5,405,378 A | 4/1995 | Strecker | |
| 5,443,500 A | 8/1995 | Sigwart | |
| 5,473,812 A | 12/1995 | Morris | |
| 5,607,444 A | 3/1997 | Sharon | |
| 5,607,470 A | 3/1997 | Milo | |
| 5,647,857 A | 7/1997 | Anderson | |
| 5,702,397 A | 12/1997 | Goble | |
| 5,713,948 A | 2/1998 | Uflacker | |
| 5,716,417 A | 2/1998 | Girard | |
| 5,741,297 A | 4/1998 | Simon | |
| 5,765,682 A | 6/1998 | Bley | |
| 5,776,140 A | 7/1998 | Cottone | |
| 5,868,777 A | 2/1999 | Sharon | |
| 5,873,906 A | 2/1999 | Lau | |
| 5,954,766 A | 9/1999 | Zadno-Azizi | |
| 5,957,949 A | 9/1999 | Eonhardt | |
| 5,980,565 A | 11/1999 | Jayaraman | |
| 6,010,530 A | 1/2000 | Goicoechea | |
| 6,019,787 A | 2/2000 | Richard | |
| 6,042,607 A | 3/2000 | Williamson, IV | |
| 6,059,827 A | 5/2000 | Fenton, V | |
| 6,074,417 A | 6/2000 | Peredo | |
| 6,113,612 A | 9/2000 | Swanson | |
| 6,120,534 A | 9/2000 | Ruiz | |
| 6,126,686 A | 10/2000 | Badylak | |
| 6,152,937 A | 11/2000 | Peterson | |
| 6,165,183 A | 12/2000 | Kuehn | |
| 6,165,210 A | 12/2000 | Lilip | |
| 6,187,020 B1 | 2/2001 | Zegdi | |
| 6,193,686 B1 | 2/2001 | Estrada | |
| 6,193,745 B1 | 2/2001 | Fogarty | |
| 6,254,609 B1 | 7/2001 | Vrba | |
| 6,264,700 B1 | 7/2001 | Kilcoyne | |
| 6,287,339 B1 | 9/2001 | Vazquez | |
| 6,312,465 B1 | 11/2001 | Griffin | |
| 6,332,893 B1 | 12/2001 | Mortier | |
| 6,334,873 B1 | 1/2002 | Ernest | |
| 6,346,074 B1 | 2/2002 | Roth | |
| 6,350,278 B1 | 2/2002 | Lenker | |
| 6,352,561 B1 | 3/2002 | Leopold | |
| 6,391,036 B1 | 5/2002 | Berg | |
| 6,402,780 B2 | 6/2002 | Williamson, IV | |
| 6,409,755 B1 | 6/2002 | Vrba | |
| 6,419,696 B1 | 7/2002 | Ortiz | |
| 6,428,550 B1 | 8/2002 | Vargas | |
| 6,440,164 B1 | 8/2002 | DiMatteo | |
| 6,454,799 B1 | 9/2002 | Schreck | |
| 6,458,153 B1 | 10/2002 | Bailey | |
| 6,478,807 B1 | 11/2002 | Foreman | |
| 6,482,228 B1 | 11/2002 | Norred | |
| 6,491,711 B1 | 12/2002 | Durcan | |
| 6,511,491 B2 | 1/2003 | Grudem | |
| 6,530,952 B2 | 3/2003 | Vesely | |
| 6,540,782 B1 | 4/2003 | Snyders | |
| 6,551,350 B1 | 4/2003 | Thornton | |
| 6,558,396 B1 | 5/2003 | Inoue | |
| 6,558,418 B2 | 5/2003 | Carpentier | |
| 6,569,196 B1 | 5/2003 | Vesely | |
| 6,602,263 B1 | 8/2003 | Swanson | |
| 6,616,675 B1 | 9/2003 | Evard | |
| 6,652,556 B1 | 11/2003 | Vantassel | |
| 6,669,724 B2 | 12/2003 | Park | |
| 6,682,558 B2 | 1/2004 | Tu | |
| 6,699,256 B1 | 3/2004 | Logan | |
| 6,716,244 B2 | 4/2004 | Klaco | |
| 6,719,781 B1 | 4/2004 | Kim | |
| 6,719,788 B2 | 4/2004 | Cox | |
| 6,730,118 B2 | 5/2004 | Spenser | |
| 6,733,525 B2 | 5/2004 | Jibin | |
| 6,752,813 B2 | 6/2004 | Goldfarb | |
| 6,764,518 B2 | 7/2004 | Godin | |
| 6,767,362 B2 | 7/2004 | Schreck | |
| 6,797,002 B2 | 9/2004 | Spence | |
| 6,821,297 B2 | 11/2004 | Snyders | |
| 6,830,585 B1 | 12/2004 | Artof | |
| 6,830,638 B2 | 12/2004 | Boylan | |
| 6,884,257 B1 | 4/2005 | Cox | |
| 6,893,460 B2 | 5/2005 | Spenser | |
| 6,926,715 B1 | 8/2005 | Hauck | |
| 6,951,571 B1 | 10/2005 | Srivastava | |
| 6,960,217 B2 | 11/2005 | Bolduc | |
| 6,964,684 B2 | 11/2005 | Ortiz | |
| 6,974,476 B2 | 12/2005 | McGuckin, Jr. | |
| 7,011,681 B2 | 3/2006 | Vesely | |
| 7,018,406 B2 | 3/2006 | Seguin | |
| 7,041,132 B2 | 5/2006 | Quijano | |
| 7,074,236 B2 | 7/2006 | Rabkin | |
| 7,077,861 B2 | 7/2006 | Spence | |
| 7,101,395 B2 | 9/2006 | Tremulis | |
| 7,101,396 B2 | 9/2006 | Artof | |
| 7,137,184 B2 | 11/2006 | Schreck | |
| 7,172,625 B2 | 2/2007 | Shu | |
| 7,175,656 B2 | 2/2007 | Khairkhahan | |
| 7,198,646 B2 | 4/2007 | Figulla | |
| 7,201,772 B2 | 4/2007 | Schwammenthal | |
| 7,226,467 B2 | 6/2007 | Lucatero | |
| 7,226,477 B2 | 6/2007 | Cox | |
| 7,261,686 B2 | 8/2007 | Couvillon, Jr. | |
| 7,288,097 B2 | 10/2007 | Seguin | |
| 7,288,111 B1 | 10/2007 | Holloway | |
| 7,316,716 B2 | 1/2008 | Egan | |
| 7,329,279 B2 | 2/2008 | Haug | |
| 7,335,213 B1 | 2/2008 | Hyde | |
| 7,351,256 B2 | 4/2008 | Hojeibane | |
| 7,374,573 B2 | 5/2008 | Gabbay | |
| 7,377,938 B2 | 5/2008 | Sarac | |
| 7,381,218 B2 | 6/2008 | Schreck | |
| 7,381,219 B2 | 6/2008 | Salahieh | |
| 7,404,824 B1 | 7/2008 | Webler | |
| 7,422,603 B2 | 9/2008 | Lane | |
| 7,429,269 B2 | 9/2008 | Schwammenthal | |
| 7,442,204 B2 | 10/2008 | Schwammenthal | |
| 7,445,630 B2 | 11/2008 | Ashinski | |
| 7,455,677 B2 | 11/2008 | Vargas | |
| 7,455,688 B2 | 11/2008 | Furst | |
| 7,462,162 B2 | 12/2008 | Phan | |
| 7,481,838 B2 | 1/2009 | Carpentier | |
| 7,510,575 B2 | 3/2009 | Spenser | |
| 7,513,909 B2 | 4/2009 | Lane | |
| 7,527,646 B2 | 5/2009 | Rahdert | |
| 7,556,632 B2 | 7/2009 | Zadno | |
| 7,556,646 B2 | 7/2009 | Yang | |
| 7,563,267 B2 | 7/2009 | Goldfarb | |
| 7,563,273 B2 | 7/2009 | Goldfarb | |
| 7,582,111 B2 | 9/2009 | Krolik | |
| 7,585,321 B2 | 9/2009 | Cribier | |
| 7,597,711 B2 | 10/2009 | Drews | |
| 7,608,091 B2 | 10/2009 | Goldfarb | |
| 7,611,534 B2 | 11/2009 | Kapadia | |
| 7,621,948 B2 | 11/2009 | Herrmann | |
| 7,625,403 B2 | 12/2009 | Krivoruchko | |
| 7,632,302 B2 | 12/2009 | Vreeman | |
| 7,635,329 B2 | 12/2009 | Goldfarb | |
| 7,648,528 B2 | 1/2010 | Styrc | |

(56) References Cited

U.S. PATENT DOCUMENTS

| | | |
|---|---|---|
| 7,655,015 B2 | 2/2010 | Goldfarb |
| 7,682,380 B2 | 3/2010 | Thornton |
| 7,708,775 B2 | 5/2010 | Rowe |
| 7,717,952 B2 | 5/2010 | Case |
| 7,717,955 B2 | 5/2010 | Ernest |
| 7,731,741 B2 | 6/2010 | Eidenschink |
| 7,731,742 B2 | 6/2010 | Schlick |
| 7,736,388 B2 | 6/2010 | Goldfarb |
| 7,748,389 B2 | 7/2010 | Salahieh |
| 7,753,922 B2 | 7/2010 | Starksen |
| 7,753,949 B2 | 7/2010 | Amphere |
| 7,758,595 B2 | 7/2010 | Allen |
| 7,758,632 B2 | 7/2010 | Hojeibane |
| 7,758,640 B2 | 7/2010 | Vesely |
| 7,771,467 B2 | 8/2010 | Svensson |
| 7,771,469 B2 | 8/2010 | Liddicoat |
| 7,776,080 B2 | 8/2010 | Bei |
| 7,776,083 B2 | 8/2010 | Vesely |
| 7,780,726 B2 | 8/2010 | Seguin |
| 7,785,341 B2 | 8/2010 | Forster |
| 7,799,069 B2 | 9/2010 | Bailey |
| 7,803,181 B2 | 9/2010 | Furst |
| 7,811,296 B2 | 10/2010 | Goldfarb |
| 7,811,316 B2 | 10/2010 | Kalmann |
| 7,824,442 B2 | 11/2010 | Salahieh |
| 7,837,645 B2 | 11/2010 | Bessler |
| 7,837,727 B2 | 11/2010 | Goetz |
| 7,842,081 B2 | 11/2010 | Yadin |
| 7,850,725 B2 | 12/2010 | Vardi |
| 7,871,432 B2 | 1/2011 | Bergin |
| 7,871,436 B2 | 1/2011 | Ryan |
| 7,887,583 B2 | 2/2011 | Macoviak |
| 7,892,281 B2 | 2/2011 | Seguin |
| 7,896,915 B2 | 3/2011 | Guyenot |
| 7,914,544 B2 | 3/2011 | Nguyen |
| 7,914,569 B2 | 3/2011 | Nguyen |
| 7,927,370 B2 | 4/2011 | Webler |
| 7,942,927 B2 | 5/2011 | Kaye |
| 7,947,072 B2 | 5/2011 | Yang |
| 7,947,075 B2 | 5/2011 | Goetz |
| 7,955,375 B2 | 6/2011 | Agnew |
| 7,955,377 B2 | 6/2011 | Melsheimer |
| 7,955,384 B2 | 6/2011 | Rafiee |
| 7,959,666 B2 | 6/2011 | Salahieh |
| 7,959,672 B2 | 6/2011 | Salahieh |
| 7,967,833 B2 | 6/2011 | Sterman |
| 7,967,857 B2 | 6/2011 | Ernest |
| 7,981,151 B2 | 7/2011 | Rowe |
| 7,981,153 B2 | 7/2011 | Fogarty |
| 7,992,567 B2 | 8/2011 | Hirotsuka |
| 7,993,393 B2 | 8/2011 | Carpentier |
| 8,002,825 B2 | 8/2011 | Brice |
| 8,002,826 B2 | 8/2011 | Seguin |
| 8,016,877 B2 | 9/2011 | Seguin |
| 8,016,882 B2 | 9/2011 | Macoviak |
| 8,021,420 B2 | 9/2011 | Dolan |
| 8,021,421 B2 | 9/2011 | Fogarty |
| 8,025,695 B2 | 9/2011 | Fogarty |
| 8,029,518 B2 | 10/2011 | Goldfarb |
| 8,029,557 B2 | 10/2011 | Sobrino-Serrano |
| 8,029,564 B2 | 10/2011 | Johnson |
| 8,034,104 B2 | 10/2011 | Carpentier |
| 8,038,720 B2 | 10/2011 | Wallace |
| 8,043,360 B2 | 10/2011 | Mcnamara |
| 3,057,532 A1 | 11/2011 | Hoffman |
| 8,048,138 B2 | 11/2011 | Sullivan |
| 8,048,140 B2 | 11/2011 | Purdy |
| 8,048,153 B2 | 11/2011 | Salahieh |
| 8,052,592 B2 | 11/2011 | Goldfarb |
| 8,052,741 B2 | 11/2011 | Bruszewski |
| 8,052,749 B2 | 11/2011 | Salahieh |
| 8,057,493 B2 | 11/2011 | Goldfarb |
| 8,057,540 B2 | 11/2011 | Brice |
| 8,062,355 B2 | 11/2011 | Figulla |
| 8,062,359 B2 | 11/2011 | Marquez |
| 8,070,708 B2 | 12/2011 | Rottenberg |
| 8,070,800 B2 | 12/2011 | Lock |
| 8,070,802 B2 | 12/2011 | Amphere |
| 8,070,804 B2 | 12/2011 | Hyde |
| 8,075,611 B2 | 12/2011 | Millwee |
| 8,080,054 B2 | 12/2011 | Rowe |
| 8,083,793 B2 | 12/2011 | Ernest |
| D652,927 S | 1/2012 | Braido |
| D653,341 S | 1/2012 | Braido |
| 8,092,518 B2 | 1/2012 | Schreck |
| 8,092,520 B2 | 1/2012 | Quadri |
| 8,092,521 B2 | 1/2012 | Figulla |
| 8,105,377 B2 | 1/2012 | Liddicoat |
| 8,109,996 B2 | 2/2012 | Stacchino |
| 8,118,866 B2 | 2/2012 | Herrmann |
| 8,133,270 B2 | 3/2012 | Kheradvar |
| 8,136,218 B2 | 3/2012 | Millwee |
| 8,137,398 B2 | 3/2012 | Tuval |
| 8,142,492 B2 | 3/2012 | Forster |
| 8,142,494 B2 | 3/2012 | Rahdert |
| 8,142,496 B2 | 3/2012 | Berreklouw |
| 8,142,497 B2 | 3/2012 | Friedman |
| 8,147,504 B2 | 4/2012 | Harry |
| 8,157,852 B2 | 4/2012 | Bloom |
| 8,157,853 B2 | 4/2012 | Laske |
| 8,157,860 B2 | 4/2012 | Mcnamara |
| 8,163,008 B2 | 4/2012 | Wilson |
| 8,163,014 B2 | 4/2012 | Ernest |
| D660,433 S | 5/2012 | Braido |
| D660,967 S | 5/2012 | Braido |
| 8,167,894 B2 | 5/2012 | Miles |
| 8,167,932 B2 | 5/2012 | Bourang |
| 8,167,935 B2 | 5/2012 | McGuckin, Jr. |
| 8,172,896 B2 | 5/2012 | McNamara |
| 8,172,898 B2 | 5/2012 | Alferness |
| 8,177,836 B2 | 5/2012 | Anthony |
| 8,182,528 B2 | 5/2012 | Salahieh |
| 8,211,169 B2 | 7/2012 | Lane |
| 8,216,256 B2 | 7/2012 | Raschdorf, Jr. |
| 8,216,301 B2 | 7/2012 | Bonhoeffer |
| 8,221,492 B2 | 7/2012 | Case |
| 8,221,493 B2 | 7/2012 | Boyle |
| 8,226,710 B2 | 7/2012 | Nguyen |
| 8,231,670 B2 | 7/2012 | Salahieh |
| 8,236,045 B2 | 8/2012 | Benichou |
| 8,236,049 B2 | 8/2012 | Rowe |
| 8,252,042 B2 | 8/2012 | McNamara et al. |
| 8,252,051 B2 | 8/2012 | Chau |
| 8,252,052 B2 | 8/2012 | Salahieh |
| 8,257,390 B2 | 9/2012 | Carley |
| 8,267,988 B2 | 9/2012 | Hamer |
| 8,277,501 B2 | 10/2012 | Chalekian |
| 8,287,591 B2 | 10/2012 | Keidar |
| 8,298,280 B2 | 10/2012 | Yadin |
| 8,303,653 B2 | 11/2012 | Bonhoeffer |
| 8,308,798 B2 | 11/2012 | Pintor |
| 8,317,853 B2 | 11/2012 | Agnew |
| 8,317,855 B2 | 11/2012 | Gregorich |
| 8,323,335 B2 | 12/2012 | Rowe |
| 8,328,868 B2 | 12/2012 | Paul |
| 8,337,541 B2 | 12/2012 | Quadri |
| 8,343,174 B2 | 1/2013 | Goldfarb |
| 8,343,213 B2 | 1/2013 | Salahieh |
| 8,348,999 B2 | 1/2013 | Kheradvar |
| 8,366,767 B2 | 2/2013 | Zhang |
| 8,372,140 B2 | 2/2013 | Hoffman |
| 8,377,119 B2 | 2/2013 | Drews |
| 8,398,708 B2 | 3/2013 | Meiri |
| 8,403,981 B2 | 3/2013 | Forster |
| 8,403,983 B2 | 3/2013 | Quadri |
| 8,408,214 B2 | 4/2013 | Spenser |
| 8,414,644 B2 | 4/2013 | Quadri |
| 8,425,593 B2 | 4/2013 | Braido |
| 8,430,934 B2 | 4/2013 | Das |
| 8,444,689 B2 | 5/2013 | Zhang |
| 8,449,599 B2 | 5/2013 | Chau |
| 8,449,625 B2 | 5/2013 | Campbell |
| 8,454,686 B2 | 6/2013 | Alkhatib |
| 8,460,365 B2 | 6/2013 | Haverkost |

(56) References Cited

U.S. PATENT DOCUMENTS

| | | |
|---|---|---|
| 8,474,460 B2 | 7/2013 | Barrett |
| 8,500,821 B2 | 8/2013 | Sobrino-Serrano |
| 8,512,400 B2 | 8/2013 | Tran |
| 8,539,662 B2 | 9/2013 | Stacchino |
| 8,540,767 B2 | 9/2013 | Zhang |
| 8,545,544 B2 | 10/2013 | Spenser |
| 8,551,160 B2 | 10/2013 | Figulla |
| 8,551,161 B2 | 10/2013 | Dolan |
| 8,562,672 B2 | 10/2013 | Bonhoeffer |
| 8,568,475 B2 | 10/2013 | Nguyen |
| 8,579,964 B2 | 11/2013 | Lane |
| 8,579,965 B2 | 11/2013 | Bonhoeffer |
| 8,585,755 B2 | 11/2013 | Chau |
| 8,585,756 B2 | 11/2013 | Bonhoeffer |
| 8,591,460 B2 | 11/2013 | Wilson |
| 8,591,570 B2 | 11/2013 | Revuelta |
| 8,623,075 B2 | 1/2014 | Murray, III |
| 8,623,080 B2 | 1/2014 | Fogarty |
| 8,628,569 B2 | 1/2014 | Benichou |
| 8,628,570 B2 | 1/2014 | Seguin |
| 8,628,571 B1 | 1/2014 | Hacohen |
| 8,652,203 B2 | 2/2014 | Quadri |
| 8,652,204 B2 | 2/2014 | Quill |
| 8,657,872 B2 | 2/2014 | Seguin |
| 8,663,322 B2 | 3/2014 | Olli |
| 8,673,020 B2 | 3/2014 | Sobrino-Serrano |
| 8,679,174 B2 | 3/2014 | Ottma |
| 8,685,086 B2 | 4/2014 | Navia |
| 8,696,742 B2 | 4/2014 | Pintor |
| 8,728,155 B2 | 5/2014 | Montorfano |
| 8,734,507 B2 | 5/2014 | Keränen |
| 8,747,460 B2 | 6/2014 | Tuval |
| 8,771,345 B2 | 7/2014 | Tuval |
| 8,784,472 B2 | 7/2014 | Eidenschink |
| 8,784,479 B2 | 7/2014 | Antonsson |
| 8,784,481 B2 | 7/2014 | Alkhatib |
| 8,795,355 B2 | 8/2014 | Alkhatib |
| 8,795,356 B2 | 8/2014 | Quadri |
| 8,795,357 B2 | 8/2014 | Yohanan |
| 8,801,776 B2 | 8/2014 | House |
| 8,808,366 B2 | 8/2014 | Braido |
| 8,840,663 B2 | 9/2014 | Salahieh |
| 8,840,664 B2 | 9/2014 | Karapetian |
| 8,845,722 B2 | 9/2014 | Gabbay |
| 8,852,261 B2 | 10/2014 | White |
| 8,852,272 B2 | 10/2014 | Gross |
| 8,870,948 B1 | 10/2014 | Erzberger |
| 8,870,949 B2 | 10/2014 | Rowe |
| 8,870,950 B2 | 10/2014 | Hacohen |
| 8,876,800 B2 | 11/2014 | Behan |
| 8,894,702 B2 | 11/2014 | Quadri |
| 8,900,294 B2 | 12/2014 | Paniagua |
| 8,900,295 B2 | 12/2014 | Migliazza |
| 8,906,083 B2 | 12/2014 | Obermiller |
| 8,911,455 B2 | 12/2014 | Quadri |
| 8,911,489 B2 | 12/2014 | Ben-Muvhar |
| 8,911,493 B2 | 12/2014 | Rowe |
| 8,932,343 B2 | 1/2015 | Alkhatib |
| 8,945,177 B2 | 2/2015 | Dell |
| 8,961,595 B2 | 2/2015 | Alkhatib |
| 8,979,922 B2 | 3/2015 | Jayasinghe |
| 8,986,370 B2 | 3/2015 | Annest |
| 8,986,373 B2 | 3/2015 | Chau |
| 8,986,375 B2 | 3/2015 | Garde |
| 8,992,599 B2 | 3/2015 | Thubrikar |
| 8,992,604 B2 | 3/2015 | Gross |
| 8,992,608 B2 | 3/2015 | Haug |
| 8,998,982 B2 | 4/2015 | Richter |
| 9,005,273 B2 | 4/2015 | Salahieh |
| 9,011,468 B2 | 4/2015 | Ketai |
| 9,011,527 B2 | 4/2015 | Li |
| 9,017,399 B2 | 4/2015 | Gross |
| D730,520 S | 5/2015 | Braido |
| D730,521 S | 5/2015 | Braido |
| 9,023,100 B2 | 5/2015 | Quadri |
| 9,034,032 B2 | 5/2015 | Mclean |
| 9,034,033 B2 | 5/2015 | Mclean |
| 9,039,757 B2 | 5/2015 | Mclean |
| D732,666 S | 6/2015 | Nguyen |
| 9,050,188 B2 | 6/2015 | Schweich, Jr. |
| 9,060,858 B2 | 6/2015 | Thornton |
| 9,072,603 B2 | 7/2015 | Tuval |
| 9,084,676 B2 | 7/2015 | Chau |
| 9,095,434 B2 | 8/2015 | Rowe |
| 9,119,719 B2 | 9/2015 | Zipory |
| 9,125,738 B2 | 9/2015 | Figulla |
| 9,125,740 B2 | 9/2015 | Morriss |
| 9,132,006 B2 | 9/2015 | Spenser |
| 9,132,009 B2 | 9/2015 | Hacohen |
| 9,138,312 B2 | 9/2015 | Tuval |
| 9,155,619 B2 | 10/2015 | Liu |
| 9,173,659 B2 | 11/2015 | Bodewadt |
| 9,173,738 B2 | 11/2015 | Murray, III |
| 9,220,594 B2 | 12/2015 | Braido |
| 9,226,820 B2 | 1/2016 | Braido |
| 9,226,839 B1 | 1/2016 | Kariniemi |
| 9,232,995 B2 | 1/2016 | Kovalsky |
| 9,241,790 B2 | 1/2016 | Matthew |
| 9,241,791 B2 | 1/2016 | Braido |
| 9,241,792 B2 | 1/2016 | Benichou |
| 9,241,794 B2 | 1/2016 | Braido |
| 9,248,014 B2 | 2/2016 | Matthew |
| 9,277,994 B2 | 3/2016 | Miller |
| 9,289,290 B2 | 3/2016 | Alkhatib |
| 9,289,291 B2 | 3/2016 | Gorman, III |
| 9,295,550 B2 | 3/2016 | Nguyen |
| 9,295,551 B2 | 3/2016 | Straubinger |
| 9,295,552 B2 | 3/2016 | Mclean |
| 9,301,836 B2 | 4/2016 | Buchbinder |
| 9,320,591 B2 | 4/2016 | Bolduc |
| D755,384 S | 5/2016 | Pesce |
| 9,326,852 B2 | 5/2016 | Spenser |
| 9,326,876 B2 | 5/2016 | Acosta |
| 9,345,573 B2 | 5/2016 | Nyuli |
| 9,387,078 B2 | 7/2016 | Gross |
| 9,393,110 B2 | 7/2016 | Levi |
| 9,421,098 B2 | 8/2016 | Gifford, III |
| 9,427,303 B2 | 8/2016 | Liddy |
| 9,427,316 B2 | 8/2016 | Schweich, Jr. |
| 9,439,757 B2 | 9/2016 | Wallace |
| 9,463,102 B2 | 10/2016 | Kelly |
| 9,474,638 B2 | 10/2016 | Robinson |
| 9,480,559 B2 | 11/2016 | Robert |
| 9,492,273 B2 | 11/2016 | Wallace |
| 9,498,314 B2 | 11/2016 | Niall |
| 9,498,332 B2 | 11/2016 | Gili |
| 9,510,947 B2 | 12/2016 | Straubinger |
| 9,532,870 B2 | 1/2017 | Cooper |
| 9,554,897 B2 | 1/2017 | Matthew |
| 9,554,899 B2 | 1/2017 | Granada |
| 9,561,103 B2 | 2/2017 | Granada |
| 9,566,152 B2 | 2/2017 | Schweich, Jr. |
| 9,597,182 B2 | 3/2017 | Straubinger |
| 9,629,716 B2 | 4/2017 | Seguin |
| 9,662,203 B2 | 5/2017 | Sheahan |
| 9,681,952 B2 | 6/2017 | Hacohen |
| 9,717,591 B2 | 8/2017 | Chau |
| 9,743,932 B2 | 8/2017 | Amplatz |
| 9,763,657 B2 | 9/2017 | Hacohen |
| 9,763,817 B2 | 9/2017 | Roeder |
| 9,770,256 B2 | 9/2017 | Cohen |
| D800,908 S | 10/2017 | Hariton |
| 9,788,941 B2 | 10/2017 | Hacohen |
| 9,895,226 B1 | 2/2018 | Harari |
| 9,987,132 B1 | 6/2018 | Ilia |
| 10,010,414 B2 | 7/2018 | Cooper |
| 10,076,415 B1 | 9/2018 | Metchik |
| 10,105,222 B1 | 10/2018 | Metchik |
| 10,111,751 B1 | 10/2018 | Metchik |
| 10,123,873 B1 | 11/2018 | Metchik |
| 10,130,475 B1 | 11/2018 | Metchik |
| 10,136,993 B1 | 11/2018 | Metchik |
| 10,143,552 B2 | 12/2018 | Wallace |
| 10,149,761 B2 | 12/2018 | Granada |

(56) References Cited

U.S. PATENT DOCUMENTS

| | | |
|---|---|---|
| 10,154,903 B2 | 12/2018 | Albitov |
| 10,154,906 B2 | 12/2018 | Granada |
| 10,159,570 B1 | 12/2018 | Metchik |
| 10,182,908 B2 | 1/2019 | Tubishevitz |
| 10,226,341 B2 | 3/2019 | Gross |
| 10,231,837 B1 | 3/2019 | Metchik |
| 10,238,493 B1 | 3/2019 | Metchik |
| 10,245,143 B2 | 4/2019 | Gross |
| 10,245,144 B1 | 4/2019 | Metchik |
| 10,258,471 B2 | 4/2019 | Georg |
| 10,299,927 B2 | 5/2019 | Mclean |
| 10,321,995 B1 | 6/2019 | Christianson |
| 10,322,020 B2 | 6/2019 | Cang |
| 10,327,895 B2 | 6/2019 | Lozonschi |
| 10,335,278 B2 | 7/2019 | Mclean |
| 10,376,361 B2 | 8/2019 | Gross |
| 10,390,952 B2 | 8/2019 | Hariton |
| 10,426,614 B2 | 10/2019 | Hariton |
| 10,507,108 B2 | 12/2019 | Delgado |
| 10,507,109 B2 | 12/2019 | Metchik |
| 10,512,456 B2 | 12/2019 | Hacohen |
| 10,517,719 B2 | 12/2019 | Miller |
| 10,524,792 B2 | 1/2020 | Hernandez |
| 10,524,910 B2 | 1/2020 | Hammer |
| 10,531,866 B2 | 1/2020 | Hariton |
| 10,531,872 B2 | 1/2020 | Hacohen |
| 10,548,731 B2 | 2/2020 | Randall |
| 10,575,948 B2 | 3/2020 | Meni |
| 10,595,992 B2 | 3/2020 | Chambers |
| 10,595,997 B2 | 3/2020 | Metchik |
| 10,610,358 B2 | 4/2020 | Vidlund |
| 10,631,871 B2 | 4/2020 | Goldfarb |
| 10,646,342 B1 | 5/2020 | Marr |
| 10,667,912 B2 | 6/2020 | Dixon |
| 10,702,385 B2 | 7/2020 | Hacohen |
| 10,758,342 B2 | 9/2020 | Chau |
| 10,813,760 B2 | 10/2020 | Metchik |
| 10,820,998 B2 | 11/2020 | Marr |
| 10,842,627 B2 | 11/2020 | Delgado |
| 10,856,972 B2 | 12/2020 | Hariton |
| 10,856,975 B2 | 12/2020 | Hariton |
| 10,856,978 B2 | 12/2020 | Straubinger |
| 10,874,514 B2 | 12/2020 | Dixon |
| 10,888,422 B2 | 1/2021 | Hariton |
| 10,888,644 B2 | 1/2021 | Ratz |
| 10,905,552 B2 | 2/2021 | Dixon |
| 10,905,554 B2 | 2/2021 | Cao |
| 10,918,483 B2 | 2/2021 | Metchik |
| 10,945,844 B2 | 3/2021 | Mccann |
| 10,959,846 B2 | 3/2021 | Marr |
| 10,993,809 B2 | 5/2021 | Mccann |
| 11,083,582 B2 | 8/2021 | Mccann |
| 11,147,672 B2 | 10/2021 | Mccann |
| 11,304,806 B2 | 4/2022 | Hariton |
| 11,389,297 B2 | 7/2022 | Franklin |
| 2001/0002445 A1 | 5/2001 | Vesely |
| 2001/0005787 A1 | 6/2001 | Oz |
| 2001/0021872 A1 | 9/2001 | Bailey |
| 2001/0056295 A1 | 12/2001 | Solem |
| 2002/0013571 A1 | 1/2002 | Goldfarb |
| 2002/0032481 A1 | 3/2002 | Gabbay |
| 2002/0099436 A1 | 7/2002 | Thornton |
| 2002/0151970 A1 | 10/2002 | Garrison |
| 2002/0177894 A1 | 11/2002 | Acosta |
| 2003/0036791 A1 | 2/2003 | Philipp |
| 2003/0050694 A1 | 3/2003 | Yang |
| 2003/0060875 A1 | 3/2003 | Wittens |
| 2003/0069635 A1 | 4/2003 | Cartledge |
| 2003/0074052 A1 | 4/2003 | Besselink |
| 2003/0083742 A1 | 5/2003 | Spence |
| 2003/0105519 A1 | 6/2003 | Fasol |
| 2003/0158578 A1 | 8/2003 | Pantages |
| 2004/0010272 A1 | 1/2004 | Manetakis |
| 2004/0030382 A1 | 2/2004 | Frederick |
| 2004/0039414 A1 | 2/2004 | Carley |
| 2004/0039436 A1 | 2/2004 | Spenser |
| 2004/0093060 A1 | 5/2004 | Seguin |
| 2004/0122503 A1 | 6/2004 | Campbell |
| 2004/0122514 A1 | 6/2004 | Fogarty |
| 2004/0133267 A1 | 7/2004 | James |
| 2004/0143315 A1 | 7/2004 | Bruun |
| 2004/0176839 A1 | 9/2004 | Huynh |
| 2004/0186558 A1 | 9/2004 | Pavcnik |
| 2004/0186565 A1 | 9/2004 | Schreck |
| 2004/0186566 A1 | 9/2004 | Hindrichs |
| 2004/0210244 A1 | 10/2004 | Vargas |
| 2004/0210304 A1 | 10/2004 | Seguin |
| 2004/0220593 A1 | 11/2004 | Greenhalgh |
| 2004/0225354 A1 | 11/2004 | Allen |
| 2004/0236354 A1 | 11/2004 | Seguin |
| 2004/0249433 A1 | 12/2004 | Freitag |
| 2004/0260389 A1 | 12/2004 | Case |
| 2004/0260394 A1 | 12/2004 | Douk |
| 2005/0004668 A1 | 1/2005 | Aklog |
| 2005/0021056 A1 | 1/2005 | Frederick |
| 2005/0027305 A1 | 2/2005 | Shiu |
| 2005/0027348 A1 | 2/2005 | Case |
| 2005/0038494 A1 | 2/2005 | Eidenschink |
| 2005/0055086 A1 | 3/2005 | Stobie |
| 2005/0075726 A1 | 4/2005 | Svanidze |
| 2005/0075731 A1 | 4/2005 | Artof |
| 2005/0080430 A1 | 4/2005 | Wright |
| 2005/0080474 A1 | 4/2005 | Andreas |
| 2005/0085900 A1 | 4/2005 | Case |
| 2005/0137686 A1 | 6/2005 | Salahieh |
| 2005/0137688 A1 | 6/2005 | Salahieh |
| 2005/0137689 A1 | 6/2005 | Salahieh |
| 2005/0137690 A1 | 6/2005 | Salahieh |
| 2005/0137691 A1 | 6/2005 | Salahieh |
| 2005/0137692 A1 | 6/2005 | Haug |
| 2005/0137693 A1 | 6/2005 | Haug |
| 2005/0137695 A1 | 6/2005 | Salahieh |
| 2005/0137697 A1 | 6/2005 | Salahieh |
| 2005/0137699 A1 | 6/2005 | Salahieh |
| 2005/0143809 A1 | 6/2005 | Salahieh |
| 2005/0149160 A1 | 7/2005 | McFerran |
| 2005/0154443 A1 | 7/2005 | Linder |
| 2005/0182483 A1 | 8/2005 | Osborne |
| 2005/0182486 A1 | 8/2005 | Gabbay |
| 2005/0197695 A1 | 9/2005 | Stacchino |
| 2005/0203549 A1 | 9/2005 | Realyvasquez |
| 2005/0203618 A1 | 9/2005 | Sharkawy |
| 2005/0216079 A1 | 9/2005 | MaCoviak |
| 2005/0234508 A1 | 10/2005 | Cummins |
| 2005/0240200 A1 | 10/2005 | Bergheim |
| 2005/0251251 A1 | 11/2005 | Cribier |
| 2005/0256566 A1 | 11/2005 | Gabbay |
| 2005/0267573 A9 | 12/2005 | Macoviak |
| 2006/0004439 A1 | 1/2006 | Spenser |
| 2006/0004469 A1 | 1/2006 | Sokel |
| 2006/0015171 A1 | 1/2006 | Armstrong |
| 2006/0020275 A1 | 1/2006 | Goldfarb |
| 2006/0020327 A1 | 1/2006 | Lashinski |
| 2006/0020333 A1 | 1/2006 | Lashinski |
| 2006/0041189 A1 | 2/2006 | Vancaillie |
| 2006/0047297 A1 | 3/2006 | Case |
| 2006/0052867 A1 | 3/2006 | Revuelta |
| 2006/0089627 A1 | 4/2006 | Burnett |
| 2006/0111773 A1 | 5/2006 | Rittgers |
| 2006/0116750 A1 | 6/2006 | Hebert |
| 2006/0122692 A1 | 6/2006 | Gilad |
| 2006/0135964 A1 | 6/2006 | Vesely |
| 2006/0155357 A1 | 7/2006 | Melsheimer |
| 2006/0161250 A1 | 7/2006 | Shaw |
| 2006/0178700 A1 | 8/2006 | Quinn |
| 2006/0178740 A1 | 8/2006 | Stacchino |
| 2006/0184203 A1 | 8/2006 | Martin |
| 2006/0190036 A1 | 8/2006 | Wendel |
| 2006/0190038 A1 | 8/2006 | Carley |
| 2006/0195183 A1 | 8/2006 | Navia |
| 2006/0195184 A1 | 8/2006 | Lane |
| 2006/0201519 A1 | 9/2006 | Frazier |
| 2006/0212111 A1 | 9/2006 | Case |
| 2006/0216404 A1 | 9/2006 | Seyler |

(56) References Cited

U.S. PATENT DOCUMENTS

| | | |
|---|---|---|
| 2006/0229708 A1 | 10/2006 | Powell |
| 2006/0241656 A1 | 10/2006 | Starksen |
| 2006/0241745 A1 | 10/2006 | Solem |
| 2006/0241748 A1 | 10/2006 | Lee |
| 2006/0247680 A1 | 11/2006 | Amplatz |
| 2006/0253191 A1 | 11/2006 | Salahieh |
| 2006/0259136 A1 | 11/2006 | Nguyen |
| 2006/0259137 A1 | 11/2006 | Artof |
| 2006/0271166 A1 | 11/2006 | Thill |
| 2006/0271171 A1 | 11/2006 | McQuinn |
| 2006/0282150 A1 | 12/2006 | Olson |
| 2006/0287719 A1 | 12/2006 | Rowe |
| 2007/0016286 A1 | 1/2007 | Herrmann |
| 2007/0016288 A1 | 1/2007 | Gurskis |
| 2007/0027528 A1 | 2/2007 | Agnew |
| 2007/0027549 A1 | 2/2007 | Godin |
| 2007/0038293 A1 | 2/2007 | St.Goar |
| 2007/0038295 A1 | 2/2007 | Case |
| 2007/0043435 A1 | 2/2007 | Seguin |
| 2007/0055340 A1 | 3/2007 | Pryor |
| 2007/0056346 A1 | 3/2007 | Spenser |
| 2007/0078510 A1 | 4/2007 | Ryan |
| 2007/0112422 A1 | 5/2007 | Dehdashtian |
| 2007/0118151 A1 | 5/2007 | Davidson |
| 2007/0162103 A1 | 7/2007 | Case |
| 2007/0162107 A1 | 7/2007 | Haug |
| 2007/0162111 A1 | 7/2007 | Fukamachi |
| 2007/0173932 A1 | 7/2007 | Cali |
| 2007/0197858 A1 | 8/2007 | Goldfarb |
| 2007/0198077 A1 | 8/2007 | Cully |
| 2007/0198097 A1 | 8/2007 | Zegdi |
| 2007/0208550 A1 | 9/2007 | Cao |
| 2007/0213810 A1 | 9/2007 | Newhauser |
| 2007/0213813 A1 | 9/2007 | Von Segesser |
| 2007/0219630 A1 | 9/2007 | Chu |
| 2007/0225759 A1 | 9/2007 | Thommen |
| 2007/0225760 A1 | 9/2007 | Moszner |
| 2007/0233186 A1 | 10/2007 | Meng |
| 2007/0233237 A1 | 10/2007 | Krivoruchko |
| 2007/0239272 A1 | 10/2007 | Navia |
| 2007/0239273 A1 | 10/2007 | Allen |
| 2007/0244546 A1 | 10/2007 | Francis |
| 2007/0255400 A1 | 11/2007 | Parravicini |
| 2008/0004688 A1 | 1/2008 | Spenser |
| 2008/0004697 A1 | 1/2008 | Lichtenstein |
| 2008/0051703 A1 | 2/2008 | Thornton |
| 2008/0071361 A1 | 3/2008 | Tuval |
| 2008/0071363 A1 | 3/2008 | Tuval |
| 2008/0071366 A1 | 3/2008 | Tuval |
| 2008/0071369 A1 | 3/2008 | Tuval |
| 2008/0077235 A1 | 3/2008 | Kirson |
| 2008/0082083 A1 | 4/2008 | Forde |
| 2008/0082159 A1 | 4/2008 | Tseng |
| 2008/0082166 A1 | 4/2008 | Styrc |
| 2008/0086164 A1 | 4/2008 | Rowe |
| 2008/0086204 A1 | 4/2008 | Rankin |
| 2008/0091261 A1 | 4/2008 | Long |
| 2008/0097595 A1 | 4/2008 | Gabbay |
| 2008/0132989 A1 | 6/2008 | Snow |
| 2008/0140003 A1 | 6/2008 | Bei |
| 2008/0147182 A1 | 6/2008 | Righini |
| 2008/0161910 A1 | 7/2008 | Revuelta |
| 2008/0167705 A1 | 7/2008 | Agnew |
| 2008/0167714 A1 | 7/2008 | St. Goar |
| 2008/0188929 A1 | 8/2008 | Schreck |
| 2008/0195200 A1 | 8/2008 | Vidlund |
| 2008/0200980 A1 | 8/2008 | Robin |
| 2008/0208328 A1 | 8/2008 | Antocci |
| 2008/0208332 A1 | 8/2008 | Lamphere |
| 2008/0221672 A1 | 9/2008 | Lamphere |
| 2008/0234814 A1 | 9/2008 | Salahieh |
| 2008/0243245 A1 | 10/2008 | Thambar |
| 2008/0255580 A1 | 10/2008 | Hoffman |
| 2008/0262609 A1 | 10/2008 | Gross |
| 2008/0269879 A1 | 10/2008 | Sathe |
| 2008/0281411 A1 | 11/2008 | Berreklouw |
| 2008/0294234 A1 | 11/2008 | Hartley |
| 2009/0005863 A1 | 1/2009 | Goetz |
| 2009/0036966 A1 | 2/2009 | O'Connor |
| 2009/0054969 A1 | 2/2009 | Salahieh |
| 2009/0082844 A1 | 3/2009 | Zacharias |
| 2009/0088836 A1 | 4/2009 | Bishop |
| 2009/0099554 A1 | 4/2009 | Forster |
| 2009/0099650 A1 | 4/2009 | Bolduc |
| 2009/0105794 A1 | 4/2009 | Ziarno |
| 2009/0112159 A1 | 4/2009 | Slattery |
| 2009/0125098 A1 | 5/2009 | Chuter |
| 2009/0157175 A1 | 6/2009 | Benichou |
| 2009/0171363 A1 | 7/2009 | Chocron |
| 2009/0177278 A1 | 7/2009 | Spence |
| 2009/0210052 A1 | 8/2009 | Forster |
| 2009/0222081 A1 | 9/2009 | Linder |
| 2009/0240320 A1 | 9/2009 | Tuval |
| 2009/0248143 A1 | 10/2009 | Laham |
| 2009/0259306 A1 | 10/2009 | Rowe |
| 2009/0264859 A1 | 10/2009 | Mas |
| 2009/0264994 A1 | 10/2009 | Saadat |
| 2009/0276040 A1 | 11/2009 | Rowe |
| 2009/0281619 A1 | 11/2009 | Le |
| 2009/0287299 A1 | 11/2009 | Tabor |
| 2009/0287304 A1 | 11/2009 | Dahlgren |
| 2009/0299449 A1 | 12/2009 | Styrc |
| 2009/0306768 A1 | 12/2009 | Quadri |
| 2009/0319037 A1 | 12/2009 | Rowe |
| 2010/0022823 A1 | 1/2010 | Goldfarb |
| 2010/0023117 A1 | 1/2010 | Yoganathan |
| 2010/0023120 A1 | 1/2010 | Holecek |
| 2010/0036479 A1 | 2/2010 | Hill |
| 2010/0036484 A1 | 2/2010 | Hariton |
| 2010/0049313 A1 | 2/2010 | Alon |
| 2010/0069852 A1 | 3/2010 | Kelley |
| 2010/0076548 A1 | 3/2010 | Konno |
| 2010/0082094 A1 | 4/2010 | Quadri |
| 2010/0100167 A1 | 4/2010 | Bortlein |
| 2010/0114299 A1 | 5/2010 | Ben Muvhar |
| 2010/0131054 A1 | 5/2010 | Tuval |
| 2010/0137979 A1 | 6/2010 | Tuval |
| 2010/0160958 A1 | 6/2010 | Clark |
| 2010/0161036 A1 | 6/2010 | Pintor |
| 2010/0161042 A1 | 6/2010 | Maisano |
| 2010/0174363 A1 | 7/2010 | Castro |
| 2010/0179643 A1 | 7/2010 | Shalev |
| 2010/0179648 A1 | 7/2010 | Richter |
| 2010/0179649 A1 | 7/2010 | Richter |
| 2010/0185277 A1 | 7/2010 | Braido |
| 2010/0217382 A1 | 8/2010 | Chau |
| 2010/0222810 A1 | 9/2010 | Debeer |
| 2010/0228285 A1 | 9/2010 | Miles |
| 2010/0234940 A1 | 9/2010 | Dolan |
| 2010/0249908 A1 | 9/2010 | Chau |
| 2010/0249917 A1 | 9/2010 | Zhang |
| 2010/0256737 A1 | 10/2010 | Pollock |
| 2010/0262232 A1 | 10/2010 | Annest |
| 2010/0280603 A1 | 11/2010 | Maisano |
| 2010/0280606 A1 | 11/2010 | Naor |
| 2010/0312333 A1 | 12/2010 | Navia |
| 2010/0324595 A1 | 12/2010 | Linder |
| 2010/0331971 A1 | 12/2010 | Keraenen |
| 2011/0004227 A1 | 1/2011 | Goldfarb |
| 2011/0004296 A1 | 1/2011 | Lutter |
| 2011/0004299 A1 | 1/2011 | Navia |
| 2011/0015729 A1 | 1/2011 | Jimenez |
| 2011/0015731 A1 | 1/2011 | Carpentier |
| 2011/0021985 A1 | 1/2011 | Spargias |
| 2011/0022165 A1 | 1/2011 | Oba |
| 2011/0029072 A1 | 2/2011 | Gabbay |
| 2011/0040374 A1 | 2/2011 | Goetz |
| 2011/0040375 A1 | 2/2011 | Brice |
| 2011/0046662 A1 | 2/2011 | Moszner |
| 2011/0054466 A1 | 3/2011 | Rothstein |
| 2011/0054596 A1 | 3/2011 | Taylor |
| 2011/0054598 A1 | 3/2011 | Johnson |
| 2011/0066233 A1 | 3/2011 | Thornton |
| 2011/0071626 A1 | 3/2011 | Wright |

(56) References Cited

U.S. PATENT DOCUMENTS

| | | |
|---|---|---|
| 2011/0077730 A1 | 3/2011 | Fenster |
| 2011/0082538 A1 | 4/2011 | Dahlgren |
| 2011/0087322 A1 | 4/2011 | Brice |
| 2011/0093063 A1 | 4/2011 | Schreck |
| 2011/0098525 A1 | 4/2011 | Kermode |
| 2011/0106247 A1 | 5/2011 | Miller |
| 2011/0112625 A1 | 5/2011 | Ben-Muvhar |
| 2011/0112632 A1 | 5/2011 | Chau |
| 2011/0113768 A1 | 5/2011 | Bauer |
| 2011/0118830 A1 | 5/2011 | Liddicoat |
| 2011/0125257 A1 | 5/2011 | Seguin |
| 2011/0125258 A1 | 5/2011 | Centola |
| 2011/0137326 A1 | 6/2011 | Bachman |
| 2011/0137397 A1 | 6/2011 | Chau |
| 2011/0137409 A1 | 6/2011 | Yang |
| 2011/0137410 A1 | 6/2011 | Gil |
| 2011/0144742 A1 | 6/2011 | Madrid |
| 2011/0166636 A1 | 7/2011 | Rowe |
| 2011/0172784 A1 | 7/2011 | Richter |
| 2011/0178597 A9 | 7/2011 | Navia |
| 2011/0184510 A1 | 7/2011 | Maisano |
| 2011/0190877 A1 | 8/2011 | Ernest |
| 2011/0190879 A1 | 8/2011 | Bobo |
| 2011/0202076 A1 | 8/2011 | Richter |
| 2011/0208283 A1 | 8/2011 | Rust |
| 2011/0208293 A1 | 8/2011 | Tabor |
| 2011/0208298 A1 | 8/2011 | Tuval |
| 2011/0213459 A1 | 9/2011 | Garrison |
| 2011/0213461 A1 | 9/2011 | Seguin |
| 2011/0218619 A1 | 9/2011 | Benichou |
| 2011/0218620 A1 | 9/2011 | Meiri |
| 2011/0224785 A1 | 9/2011 | Hacohen |
| 2011/0238159 A1 | 9/2011 | Guyenot |
| 2011/0245911 A1 | 10/2011 | Quill |
| 2011/0245917 A1 | 10/2011 | Savage |
| 2011/0251675 A1 | 10/2011 | Dwork |
| 2011/0251676 A1 | 10/2011 | Sweeney |
| 2011/0251678 A1 | 10/2011 | Eidenschink |
| 2011/0251679 A1 | 10/2011 | Wiemeyer |
| 2011/0251680 A1 | 10/2011 | Tran |
| 2011/0251682 A1 | 10/2011 | Murray, III |
| 2011/0251683 A1 | 10/2011 | Tabor |
| 2011/0257721 A1 | 10/2011 | Tabor |
| 2011/0257729 A1 | 10/2011 | Spenser |
| 2011/0257736 A1 | 10/2011 | Marquez |
| 2011/0257737 A1 | 10/2011 | Fogarty |
| 2011/0264191 A1 | 10/2011 | Rothstein |
| 2011/0264196 A1 | 10/2011 | Savage |
| 2011/0264198 A1 | 10/2011 | Murray, III |
| 2011/0264199 A1 | 10/2011 | Tran |
| 2011/0264200 A1 | 10/2011 | Tran |
| 2011/0264201 A1 | 10/2011 | Yeung |
| 2011/0264202 A1 | 10/2011 | Murray, III |
| 2011/0264203 A1 | 10/2011 | Dwork |
| 2011/0264206 A1 | 10/2011 | Tabor |
| 2011/0264208 A1 | 10/2011 | Duffy |
| 2011/0270276 A1 | 11/2011 | Rothstein |
| 2011/0271967 A1 | 11/2011 | Mortier |
| 2011/0282438 A1 | 11/2011 | Drews |
| 2011/0282439 A1 | 11/2011 | Thill |
| 2011/0282440 A1 | 11/2011 | Cao |
| 2011/0283514 A1 | 11/2011 | Fogarty |
| 2011/0288632 A1 | 11/2011 | White |
| 2011/0288634 A1 | 11/2011 | Tuval |
| 2011/0295354 A1 | 12/2011 | Bueche |
| 2011/0295363 A1 | 12/2011 | Girard |
| 2011/0301688 A1 | 12/2011 | Dolan |
| 2011/0301698 A1 | 12/2011 | Miller |
| 2011/0301701 A1 | 12/2011 | Padala |
| 2011/0301702 A1 | 12/2011 | Rust |
| 2011/0306916 A1 | 12/2011 | Nitzan |
| 2011/0307049 A1 | 12/2011 | Kao |
| 2011/0313452 A1 | 12/2011 | Carley |
| 2011/0313515 A1 | 12/2011 | Quadri |
| 2011/0319989 A1 | 12/2011 | Lane |
| 2011/0319991 A1 | 12/2011 | Hariton |
| 2012/0010694 A1 | 1/2012 | Lutter |
| 2012/0016468 A1 | 1/2012 | Robin |
| 2012/0022629 A1 | 1/2012 | Perera |
| 2012/0022633 A1 | 1/2012 | Olson |
| 2012/0022637 A1 | 1/2012 | Ben-Muvhar |
| 2012/0022639 A1 | 1/2012 | Hacohen |
| 2012/0022640 A1 | 1/2012 | Gross |
| 2012/0035703 A1 | 2/2012 | Lutter |
| 2012/0035713 A1 | 2/2012 | Lutter |
| 2012/0035722 A1 | 2/2012 | Tuval |
| 2012/0041547 A1 | 2/2012 | Duffy |
| 2012/0041551 A1 | 2/2012 | Spenser |
| 2012/0046738 A1 | 2/2012 | Lau |
| 2012/0046742 A1 | 2/2012 | Tuval |
| 2012/0053676 A1 | 3/2012 | Ku |
| 2012/0053682 A1 | 3/2012 | Kovalsky |
| 2012/0053688 A1 | 3/2012 | Fogarty |
| 2012/0059337 A1 | 3/2012 | Eilat |
| 2012/0059454 A1 | 3/2012 | Millwee |
| 2012/0059458 A1 | 3/2012 | Buchbinder |
| 2012/0065464 A1 | 3/2012 | Ellis |
| 2012/0078237 A1 | 3/2012 | Wang |
| 2012/0078353 A1 | 3/2012 | Quadri |
| 2012/0078357 A1 | 3/2012 | Conklin |
| 2012/0083832 A1 | 4/2012 | Delaloye |
| 2012/0083839 A1 | 4/2012 | Letac |
| 2012/0083879 A1 | 4/2012 | Eberhardt |
| 2012/0089223 A1 | 4/2012 | Nguyen |
| 2012/0101570 A1 | 4/2012 | Tuval |
| 2012/0101571 A1 | 4/2012 | Thambar |
| 2012/0101572 A1 | 4/2012 | Kovalsky |
| 2012/0123511 A1 | 5/2012 | Brown |
| 2012/0123529 A1 | 5/2012 | Tamir |
| 2012/0123530 A1 | 5/2012 | Carpentier |
| 2012/0130473 A1 | 5/2012 | Norris |
| 2012/0130474 A1 | 5/2012 | Buckley |
| 2012/0130475 A1 | 5/2012 | Shaw |
| 2012/0136434 A1 | 5/2012 | Carpentier |
| 2012/0150218 A1 | 6/2012 | Sandgren |
| 2012/0165915 A1 | 6/2012 | Melsheimer |
| 2012/0165930 A1 | 6/2012 | Gifford, III |
| 2012/0179244 A1 | 7/2012 | Schankereli |
| 2012/0197292 A1 | 8/2012 | Chin-Chen |
| 2012/0283824 A1 | 11/2012 | Lutter |
| 2012/0290062 A1 | 11/2012 | Mcnamara |
| 2012/0296360 A1 | 11/2012 | Norris |
| 2012/0296418 A1 | 11/2012 | Bonyuet |
| 2012/0300063 A1 | 11/2012 | Majkrzak |
| 2012/0310328 A1 | 12/2012 | Olson |
| 2012/0323316 A1 | 12/2012 | Chau |
| 2012/0330408 A1 | 12/2012 | Hillukka |
| 2013/0006347 A1 | 1/2013 | Mchugo |
| 2013/0018450 A1 | 1/2013 | Hunt |
| 2013/0018458 A1 | 1/2013 | Yohanan |
| 2013/0030519 A1 | 1/2013 | Tran |
| 2013/0035759 A1 | 2/2013 | Gross |
| 2013/0041204 A1 | 2/2013 | Heilman |
| 2013/0041451 A1 | 2/2013 | Patterson |
| 2013/0046373 A1 | 2/2013 | Cartledge |
| 2013/0066342 A1 | 3/2013 | Dell |
| 2013/0079872 A1 | 3/2013 | Gallagher |
| 2013/0116779 A1 | 5/2013 | Weber |
| 2013/0116780 A1 | 5/2013 | Miller |
| 2013/0123896 A1 | 5/2013 | Bloss |
| 2013/0123900 A1 | 5/2013 | Eblacas |
| 2013/0150945 A1 | 6/2013 | Crawford |
| 2013/0150956 A1 | 6/2013 | Yohanan |
| 2013/0158647 A1 | 6/2013 | Norris |
| 2013/0166017 A1 | 6/2013 | Cartledge |
| 2013/0166022 A1 | 6/2013 | Conklin |
| 2013/0172978 A1 | 7/2013 | Robert |
| 2013/0172992 A1 | 7/2013 | Gross |
| 2013/0178930 A1 | 7/2013 | Straubinger |
| 2013/0190861 A1 | 7/2013 | Chau |
| 2013/0211501 A1 | 8/2013 | Buckley |
| 2013/0231735 A1 | 9/2013 | Deem |
| 2013/0245742 A1 | 9/2013 | Norris |
| 2013/0253634 A1 | 9/2013 | Wilson |

(56) References Cited

U.S. PATENT DOCUMENTS

| | | |
|---|---|---|
| 2013/0253643 A1 | 9/2013 | Rolando |
| 2013/0261737 A1 | 10/2013 | Costello |
| 2013/0261738 A1 | 10/2013 | Clague |
| 2013/0274870 A1 | 10/2013 | Lombardi |
| 2013/0282059 A1 | 10/2013 | Ketai |
| 2013/0289711 A1 | 10/2013 | Liddy |
| 2013/0289740 A1 | 10/2013 | Liddy |
| 2013/0297013 A1 | 11/2013 | Klima |
| 2013/0304197 A1 | 11/2013 | Buchbinder |
| 2013/0304200 A1 | 11/2013 | Mclean |
| 2013/0310928 A1 | 11/2013 | Morriss |
| 2013/0325114 A1 | 12/2013 | Mclean |
| 2013/0331929 A1 | 12/2013 | Mitra |
| 2014/0000112 A1 | 1/2014 | Braido |
| 2014/0005778 A1* | 1/2014 | Buchbinder .......... A61F 2/2445 623/2.37 |
| 2014/0018911 A1 | 1/2014 | Zhou |
| 2014/0018915 A1 | 1/2014 | Biadillah |
| 2014/0031928 A1 | 1/2014 | Murphy |
| 2014/0046430 A1 | 2/2014 | Shaw |
| 2014/0052237 A1 | 2/2014 | Lane |
| 2014/0067050 A1 | 3/2014 | Costello |
| 2014/0067054 A1 | 3/2014 | Chau |
| 2014/0081376 A1 | 3/2014 | Burkart |
| 2014/0106951 A1 | 4/2014 | Brandon |
| 2014/0120287 A1 | 5/2014 | Jacoby |
| 2014/0121749 A1 | 5/2014 | Roeder |
| 2014/0121763 A1 | 5/2014 | Duffy |
| 2014/0135894 A1 | 5/2014 | Norris |
| 2014/0135895 A1 | 5/2014 | Andress |
| 2014/0142681 A1 | 5/2014 | Norris |
| 2014/0142688 A1 | 5/2014 | Duffy |
| 2014/0148891 A1 | 5/2014 | Johnson |
| 2014/0163690 A1 | 6/2014 | White |
| 2014/0172069 A1 | 6/2014 | Roeder |
| 2014/0172077 A1 | 6/2014 | Bruchman |
| 2014/0172082 A1 | 6/2014 | Bruchman |
| 2014/0188210 A1 | 7/2014 | Beard |
| 2014/0188221 A1 | 7/2014 | Chung |
| 2014/0194970 A1 | 7/2014 | Chobotov |
| 2014/0194981 A1 | 7/2014 | Menk |
| 2014/0194983 A1 | 7/2014 | Kovalsky |
| 2014/0207231 A1 | 7/2014 | Hacohen |
| 2014/0214159 A1 | 7/2014 | Robert |
| 2014/0222136 A1 | 8/2014 | Geist |
| 2014/0222142 A1 | 8/2014 | Kovalsky |
| 2014/0236287 A1 | 8/2014 | Clague |
| 2014/0236289 A1 | 8/2014 | Alkhatib |
| 2014/0249622 A1 | 9/2014 | Carmi |
| 2014/0257461 A1 | 9/2014 | Robinson |
| 2014/0257467 A1 | 9/2014 | Lane |
| 2014/0257475 A1 | 9/2014 | Gross |
| 2014/0257476 A1 | 9/2014 | Montorfano |
| 2014/0277358 A1 | 9/2014 | Slazas |
| 2014/0277409 A1 | 9/2014 | Börtlein |
| 2014/0277411 A1 | 9/2014 | Börtlein |
| 2014/0277418 A1 | 9/2014 | Noam |
| 2014/0277422 A1 | 9/2014 | Ratz |
| 2014/0277427 A1 | 9/2014 | Ratz |
| 2014/0296962 A1 | 10/2014 | Cartledge |
| 2014/0296969 A1 | 10/2014 | Tegels |
| 2014/0324164 A1* | 10/2014 | Gross .................. A61F 2/2418 623/2.37 |
| 2014/0336744 A1 | 11/2014 | Tani |
| 2014/0343670 A1 | 11/2014 | Bakis |
| 2014/0358222 A1 | 12/2014 | Gorman, III |
| 2014/0358224 A1 | 12/2014 | Tegels |
| 2014/0379065 A1 | 12/2014 | Johnson |
| 2014/0379074 A1 | 12/2014 | Spence |
| 2014/0379076 A1 | 12/2014 | Vidlund |
| 2015/0018944 A1 | 1/2015 | O'Connell |
| 2015/0032205 A1 | 1/2015 | Matheny |
| 2015/0045880 A1 | 2/2015 | Hacohen |
| 2015/0045881 A1 | 2/2015 | Lim |
| 2015/0094802 A1 | 4/2015 | Buchbinder |
| 2015/0119970 A1 | 4/2015 | Nakayama |
| 2015/0127097 A1 | 5/2015 | Neumann |
| 2015/0142100 A1 | 5/2015 | Morriss |
| 2015/0142103 A1 | 5/2015 | Vidlund |
| 2015/0148894 A1 | 5/2015 | Damm |
| 2015/0157457 A1 | 6/2015 | Hacohen |
| 2015/0157458 A1 | 6/2015 | Thambar |
| 2015/0173896 A1 | 6/2015 | Richter |
| 2015/0173897 A1 | 6/2015 | Raanani |
| 2015/0196390 A1 | 7/2015 | Ma |
| 2015/0196393 A1 | 7/2015 | Vidlund |
| 2015/0216661 A1 | 8/2015 | Hacohen |
| 2015/0238313 A1 | 8/2015 | Spence |
| 2015/0245934 A1 | 9/2015 | Lombardi |
| 2015/0250588 A1 | 9/2015 | Yang |
| 2015/0272730 A1 | 10/2015 | Melnick |
| 2015/0272731 A1 | 10/2015 | Racchini |
| 2015/0272734 A1 | 10/2015 | Sheps |
| 2015/0282964 A1 | 10/2015 | Beard |
| 2015/0320556 A1 | 11/2015 | Levi |
| 2015/0327994 A1 | 11/2015 | Morriss |
| 2015/0328000 A1 | 11/2015 | Ratz |
| 2015/0335429 A1 | 11/2015 | Morriss |
| 2015/0342736 A1 | 12/2015 | Rabito |
| 2015/0351903 A1 | 12/2015 | Morriss |
| 2015/0351904 A1 | 12/2015 | Cooper |
| 2015/0351906 A1 | 12/2015 | Hammer |
| 2015/0359629 A1 | 12/2015 | Ganesan |
| 2016/0030169 A1 | 2/2016 | Shahriari |
| 2016/0030171 A1 | 2/2016 | Quijano |
| 2016/0089482 A1 | 3/2016 | Siegenthaler |
| 2016/0095700 A1 | 4/2016 | Righini |
| 2016/0100939 A1 | 4/2016 | Armstrong |
| 2016/0106539 A1 | 4/2016 | Buchbinder |
| 2016/0113766 A1 | 4/2016 | Ganesan |
| 2016/0113768 A1 | 4/2016 | Ganesan |
| 2016/0125160 A1 | 5/2016 | Heneghan |
| 2016/0175095 A1 | 6/2016 | Dienno |
| 2016/0213473 A1 | 7/2016 | Hacohen |
| 2016/0220367 A1 | 8/2016 | Barrett |
| 2016/0228247 A1 | 8/2016 | Maimon |
| 2016/0242902 A1 | 8/2016 | Morriss |
| 2016/0270911 A1 | 9/2016 | Ganesan |
| 2016/0296330 A1 | 10/2016 | Hacohen |
| 2016/0310268 A1 | 10/2016 | Oba |
| 2016/0310274 A1 | 10/2016 | Gross |
| 2016/0317301 A1 | 11/2016 | Quadri |
| 2016/0317305 A1 | 11/2016 | Pelled |
| 2016/0324633 A1 | 11/2016 | Gross |
| 2016/0324635 A1 | 11/2016 | Vidlund |
| 2016/0324640 A1 | 11/2016 | Gifford, III |
| 2016/0331526 A1 | 11/2016 | Schweich, Jr. |
| 2016/0331527 A1 | 11/2016 | Robert |
| 2016/0338706 A1 | 11/2016 | Rowe |
| 2016/0367360 A1 | 12/2016 | Cartledge |
| 2016/0367368 A1 | 12/2016 | Vidlund |
| 2016/0374801 A1 | 12/2016 | Jimenez |
| 2016/0374802 A1 | 12/2016 | Levi |
| 2017/0042678 A1 | 2/2017 | Ganesan |
| 2017/0049435 A1 | 2/2017 | Sauer |
| 2017/0056166 A1 | 3/2017 | Ratz |
| 2017/0056171 A1 | 3/2017 | Cooper |
| 2017/0065407 A1 | 3/2017 | Hacohen |
| 2017/0065411 A1 | 3/2017 | Grundeman |
| 2017/0128205 A1 | 5/2017 | Tamir |
| 2017/0135816 A1 | 5/2017 | Randall |
| 2017/0189174 A1 | 7/2017 | Braido |
| 2017/0196688 A1 | 7/2017 | Christianson |
| 2017/0196692 A1 | 7/2017 | Kirk |
| 2017/0209264 A1 | 7/2017 | Chau |
| 2017/0216026 A1 | 8/2017 | Quill |
| 2017/0224323 A1 | 8/2017 | Rowe |
| 2017/0231757 A1 | 8/2017 | Gassler |
| 2017/0231759 A1 | 8/2017 | Geist |
| 2017/0231760 A1 | 8/2017 | Lane |
| 2017/0239048 A1 | 8/2017 | Goldfarb |
| 2017/0333183 A1 | 11/2017 | Backus |
| 2017/0333187 A1 | 11/2017 | Hariton |
| 2018/0000580 A1 | 1/2018 | Wallace |

(56) References Cited

U.S. PATENT DOCUMENTS

| | | |
|---|---|---|
| 2018/0021129 A1 | 1/2018 | Peterson |
| 2018/0028215 A1 | 2/2018 | Cohen |
| 2018/0049873 A1 | 2/2018 | Manash |
| 2018/0055628 A1 | 3/2018 | Patel |
| 2018/0055630 A1 | 3/2018 | Patel |
| 2018/0098850 A1 | 4/2018 | Rafiee |
| 2018/0116843 A1 | 5/2018 | Schreck |
| 2018/0125644 A1 | 5/2018 | Conklin |
| 2018/0153687 A1 | 6/2018 | Ilia |
| 2018/0153689 A1 | 6/2018 | Maimon |
| 2018/0153696 A1 | 6/2018 | Albitov |
| 2018/0177593 A1 | 6/2018 | Hariton |
| 2018/0177594 A1 | 6/2018 | Patel |
| 2018/0185148 A1 | 7/2018 | Hariton |
| 2018/0206983 A1 | 7/2018 | Noe |
| 2018/0214263 A1 | 8/2018 | Rolando |
| 2018/0250126 A1 | 9/2018 | O'Connor |
| 2018/0250147 A1 | 9/2018 | Syed |
| 2018/0296336 A1 | 10/2018 | Cooper |
| 2018/0296341 A1 | 10/2018 | Noe |
| 2018/0325671 A1 | 11/2018 | Abunassar |
| 2018/0344457 A1 | 12/2018 | Gross |
| 2018/0344490 A1 | 12/2018 | Fox |
| 2018/0353294 A1 | 12/2018 | Calomeni |
| 2018/0360457 A1 | 12/2018 | Ellis |
| 2019/0053896 A1 | 2/2019 | Adamek-Bowers |
| 2019/0060060 A1 | 2/2019 | Chau |
| 2019/0060068 A1 | 2/2019 | Cope |
| 2019/0060070 A1 | 2/2019 | Groothuis |
| 2019/0069997 A1 | 3/2019 | Ratz |
| 2019/0105153 A1 | 4/2019 | Barash |
| 2019/0117391 A1 | 4/2019 | Humair |
| 2019/0167423 A1 | 6/2019 | Hariton |
| 2019/0175339 A1 | 6/2019 | Vidlund |
| 2019/0175342 A1 | 6/2019 | Hariton |
| 2019/0183639 A1 | 6/2019 | Moore |
| 2019/0192295 A1 | 6/2019 | Spence |
| 2019/0216602 A1 | 7/2019 | Lozonschi |
| 2019/0231525 A1 | 8/2019 | Hariton |
| 2019/0336280 A1 | 11/2019 | Naor |
| 2019/0350701 A1 | 11/2019 | Adamek-Bowers |
| 2019/0365530 A1 | 12/2019 | Hoang |
| 2019/0388218 A1 | 12/2019 | Vidlund |
| 2019/0388220 A1 | 12/2019 | Vidlund |
| 2020/0000449 A1 | 1/2020 | Goldfarb |
| 2020/0000579 A1 | 1/2020 | Manash |
| 2020/0015964 A1 | 1/2020 | Noe |
| 2020/0030098 A1 | 1/2020 | Delgado |
| 2020/0054335 A1 | 2/2020 | Hernandez |
| 2020/0060818 A1 | 2/2020 | Geist |
| 2020/0113677 A1 | 4/2020 | Mccann |
| 2020/0113689 A1 | 4/2020 | Mccann |
| 2020/0113692 A1 | 4/2020 | Mccann |
| 2020/0138567 A1 | 5/2020 | Marr |
| 2020/0163761 A1 | 5/2020 | Hariton |
| 2020/0214832 A1 | 7/2020 | Metchik |
| 2020/0237512 A1 | 7/2020 | Mccann |
| 2020/0246136 A1 | 8/2020 | Marr |
| 2020/0246140 A1 | 8/2020 | Hariton |
| 2020/0253600 A1 | 8/2020 | Darabian |
| 2020/0261094 A1 | 8/2020 | Goldfarb |
| 2020/0306037 A1 | 10/2020 | Siegel |
| 2020/0315786 A1 | 10/2020 | Metchik |
| 2020/0337842 A1 | 10/2020 | Metchik |
| 2021/0093449 A1 | 4/2021 | Hariton |
| 2021/0106419 A1 | 4/2021 | Abunassar |
| 2021/0113331 A1 | 4/2021 | Quadri |

FOREIGN PATENT DOCUMENTS

| | | |
|---|---|---|
| EP | 0170262 | 2/1986 |
| EP | 1264582 | 12/2002 |
| EP | 1637092 A2 | 3/2006 |
| EP | 1768630 | 4/2007 |
| EP | 2349124 B1 | 10/2018 |
| EP | 3583922 A1 | 12/2019 |
| EP | 3270825 B1 | 4/2020 |
| EP | 2485795 B1 | 9/2020 |
| JP | S53152790 | 12/1978 |
| KR | 20010046894 | 6/2001 |
| WO | 9843557 | 10/1998 |
| WO | 1999030647 | 6/1999 |
| WO | 2000047139 | 8/2000 |
| WO | 2001062189 | 8/2001 |
| WO | 0182832 | 11/2001 |
| WO | 0187190 | 11/2001 |
| WO | 2003020179 | 3/2003 |
| WO | 2003028558 | 4/2003 |
| WO | 2004028399 A2 | 4/2004 |
| WO | 2004108191 | 12/2004 |
| WO | 2005107650 | 11/2005 |
| WO | 2006007389 A1 | 1/2006 |
| WO | 2006007401 | 1/2006 |
| WO | 06054930 | 5/2006 |
| WO | 2006070372 | 7/2006 |
| WO | 2006086434 | 8/2006 |
| WO | 2006089236 | 8/2006 |
| WO | 2006116558 | 11/2006 |
| WO | 2006128193 | 11/2006 |
| WO | 2007047488 A2 | 4/2007 |
| WO | 2007059252 | 5/2007 |
| WO | 08013915 | 1/2008 |
| WO | 2008029296 | 3/2008 |
| WO | 2008031103 | 3/2008 |
| WO | 2008070797 | 6/2008 |
| WO | 2008103722 | 8/2008 |
| WO | 09033469 | 3/2009 |
| WO | 09053497 | 4/2009 |
| WO | 2009091509 | 7/2009 |
| WO | 2010006627 | 1/2010 |
| WO | 2010027485 A1 | 3/2010 |
| WO | 2010037141 | 4/2010 |
| WO | 2010045297 | 4/2010 |
| WO | 2010057262 | 5/2010 |
| WO | 2010073246 | 7/2010 |
| WO | 2010081033 | 7/2010 |
| WO | 2010121076 | 10/2010 |
| WO | 2011025972 | 3/2011 |
| WO | 2011069048 | 6/2011 |
| WO | 2011089601 | 7/2011 |
| WO | 2011106137 | 9/2011 |
| WO | 2011111047 | 9/2011 |
| WO | 2011137531 | 11/2011 |
| WO | 2011143263 | 11/2011 |
| WO | 2011144351 A2 | 11/2011 |
| WO | 2011154942 | 12/2011 |
| WO | 2012011108 | 1/2012 |
| WO | 2012024428 | 2/2012 |
| WO | 2012036740 | 3/2012 |
| WO | 2012048035 | 4/2012 |
| WO | 2012127309 | 9/2012 |
| WO | 2012177942 | 12/2012 |
| WO | 2013021374 | 2/2013 |
| WO | 2013021375 | 2/2013 |
| WO | 2013021384 | 2/2013 |
| WO | 2013059747 | 4/2013 |
| WO | 2013072496 | 5/2013 |
| WO | 2013078497 | 6/2013 |
| WO | 2013114214 | 8/2013 |
| WO | 2013128436 | 9/2013 |
| WO | 2013175468 | 11/2013 |
| WO | 2014022124 | 2/2014 |
| WO | 2014076696 | 5/2014 |
| WO | 2014115149 | 7/2014 |
| WO | 2014121280 A2 | 8/2014 |
| WO | 2014144937 A2 | 9/2014 |
| WO | 2014145338 | 9/2014 |
| WO | 2014164364 | 10/2014 |
| WO | 2014194178 | 12/2014 |
| WO | 2015173794 | 11/2015 |
| WO | 2016016899 | 2/2016 |
| WO | 2016093877 | 6/2016 |
| WO | 2016125160 A1 | 8/2016 |
| WO | 2017223486 | 12/2017 |

(56) References Cited

FOREIGN PATENT DOCUMENTS

| | | |
|---|---|---|
| WO | 2018025260 | 2/2018 |
| WO | 2018025263 | 2/2018 |
| WO | 2018029680 | 2/2018 |
| WO | 2018039631 | 3/2018 |
| WO | 2018106837 | 6/2018 |
| WO | 2018108837 | 6/2018 |
| WO | 2018112429 | 6/2018 |
| WO | 2018118717 | 6/2018 |
| WO | 2018131042 | 7/2018 |
| WO | 2018131043 | 7/2018 |
| WO | 2019026059 | 2/2019 |
| WO | 2019027507 | 2/2019 |
| WO | 2019030753 | 2/2019 |
| WO | 2019077595 | 4/2019 |
| WO | 2019116369 | 6/2019 |
| WO | 2019138400 | 7/2019 |
| WO | 2019195860 | 10/2019 |
| WO | 2019202579 | 10/2019 |
| WO | 2020058972 | 3/2020 |
| WO | 2020167677 | 8/2020 |

OTHER PUBLICATIONS

Jansen, J., Willeke, S., Reul, H. and Rum, G. (1992), Detachable Shape-Memory Sewing Ring for Heart Valves. Artificial Organs, 16:294-297. 1992 (an abstract).
Alexander S. Geha, et al., Replacement of degenerated mitral and aortic bioprostheses without explanation Ann Thorac Surg. Jun. 2001; 72:1509-1514.
An International Search Report and a Written Opinion both dated Oct. 13, 2011 which issued during the prosecution of Applicant's PCT/IL11/00231.
An Office Action dated Jul. 1, 2016, which issued during the prosecution of U.S. Appl. No. 14/161,921.
An International Search Report and a Written Opinion both dated Dec. 5, 2011, which issued during the prosecution of Applicant's PCT/IL11/00582.
An Office Action dated May 29, 2012, which issued during the prosecution of U.S. Appl. No. 12/840,463.
U.S. Appl. No. 61/555,160, filed Nov. 3, 2011.
U.S. Appl. No. 61/525,281, filed Aug. 19, 2011.
U.S. Appl. No. 61/537,276, filed Sep. 21, 2011.
U.S. Appl. No. 61/515,372, filed Aug. 5, 2011.
U.S. Appl. No. 61/492,449, filed Jun. 2, 2011.
U.S. Appl. No. 61/588,892, filed Jan. 20, 2012.
An International Search Report and a Written Opinion both dated Feb. 6, 2013, which issued during the prosecution of Applicant's PCT/IL12/00292.
An International Search Report and a Written Opinion both dated Feb. 6, 2013, which issued during the prosecution of Applicant's PCT/IL12/00293.
An Office Action dated Nov. 28, 2012, which issued during the prosecution of U.S. Appl. No. 12/961,721.
An Office Action dated Feb. 15, 2013, which issued during the prosecution of U.S. Appl. No. 12/840,463.
An Office Action dated Feb. 10, 2014, which issued during the prosecution of U.S. Appl. No. 13/033,852.
An Office Action dated Sep. 19, 2014, which issued during the prosecution of U.S. Appl. No. 13/044,694.
An International Search Report and a Written Opinion both dated Sep. 4, 2014 which issued during the prosecution of Applicant's PCT/IL2014/050087.
Invitation to Pay Additional Fees dated Jun. 12, 2014 PCTYIL2014/050087.
An Office Action dated Jun. 17, 2014, which issued during the prosecution of U.S. Appl. No. 12/961,721.
An Office Action dated Jul. 3, 2014, which issued during the prosecution of U.S. Appl. No. 13/033,852.
An Office Action dated May 23, 2014, which issued during the prosecution of U.S. Appl. No. 13/412,814.
Dominique Himbert; Mitral Regurgitation and Stenosis from Bioprosthesis and Annuloplasty Failure: Transcatheter approaches and outcomes, 24 pages Oct. 28, 2013.
An International Preliminary Report on patentabilty dated Dec. 2, 2013, which issued during the prosecution of Applicant's PCT/IL11/00582.
An Office Action dated Sep. 12, 2013, which issued during the prosecution of U.S. Appl. No. 13/412,814.
An Office Action dated Aug. 2, 2013, which issued during the prosecution of U.S. Appl. No. 13/033,852.
An International Preliminary Report on patentabilty dated Sep. 11, 2012, which issued during the prosecution of Applicant's PCT/IL2011/000231.
An Office Action dated Jul. 2, 2014, which issued during the prosecution of U.S. Appl. No. 13/811,308.
An Office Action dated Jan. 20, 2016, which issued during the prosecution of U.S. Appl. No. 14/161,921.
An Office Action dated Jul. 23, 2013, which issued during the prosecution of U.S. Appl. No. 12/961,721.
An Office Action dated Jul. 18, 2013, which issued during the prosecution of U.S. Appl. No. 13/044,694.
An Office Action dated Nov. 8, 2013, which issued during the prosecution of U.S. Appl. No. 12/840,463.
An Office Action dated Jun. 4, 2014, which issued during the prosecution of U.S. Appl. No. 12/840,463.
An Office Action dated Aug. 13, 2012, which issued during the prosecution of U.S. Appl. No. 13/044,694.
An Office Action dated Jul. 2, 2012, which issued during the prosecution of U.S. Appl. No. 13/033,852.
An Office Action dated Feb. 3, 2014, which issued during the prosecution of U.S. Appl. No. 13/811,308.
An International Preliminary Report on patentabilty dated Feb. 11, 2014, which issued during the prosecution of Applicant's PCT/IL12/00292.
An International Preliminary Report on patentabilty dated Feb. 11, 2014, which issued during the prosecution of Applicant's PCT/IL12/00293.
A Notice of Allowance dated Aug. 15, 2014, which issued during the prosecution of U.S. Appl. No. 13/412,814.
An Office Action dated Aug. 14, 2012, which issued during the prosecution of U.S. Appl. No. 12/961,721.
U.S. Appl. No. 61/283,819, filed Dec. 8, 2009.
Notice of Allowance dated Apr. 8, 2016, which issued during the prosecution of U.S. Appl. No. 14/237,258.
U.S. Appl. No. 61/756,034, filed Jan. 24, 2013.
U.S. Appl. No. 61/756,049, filed Jan. 24, 2013.
An International Preliminary Report on Patentability dated Jan. 31, 2017, which issued during the prosecution of Applicant's PCT/IL2015/050792.
An Invitation to pay additional fees dated Mar. 14, 2019, which issued during the prosecution of Applicant's PCT/IL2018/051350.
Notice of Allowance dated Apr. 20, 2018, which issued during the prosecution of U.S. Appl. No. 15/878,206.
An Office Action dated Dec. 10, 2015, which issued during the prosecution of U.S. Appl. No. 14/237,258.
An International Preliminary Report on Patentability dated Jul. 28, 2015, which issued during the prosecution of Applicant's PCT/IL2014/050087.
European Search Report dated Mar. 20, 2023 which issued during the prosecution of Applicant's European App No. 22204764.9.
An Office Action dated Apr. 14, 2023, which issued during the prosecution of U.S. Appl. No. 16/144,054.
An Office Action dated May 15, 2023, which issued during the prosecution of U.S. Appl. No. 16/656,790.
An Office Action dated May 16, 2023, which issued during the prosecution of U.S. Appl. No. 17/114,771.
An Office Action dated May 17, 2023, which issued during the prosecution of U.S. Appl. No. 17/466,785.
An Office Action dated May 25, 2023, which issued during the prosecution of U.S. Appl. No. 17/397,235.
Notice of Allowance dated Mar. 12, 2020, which issued during the prosecution of U.S. Appl. No. 16/460,313.

(56) References Cited

OTHER PUBLICATIONS

An Office Action dated Jan. 9, 2020, which issued during the prosecution of U.S. Appl. No. 15/600,190.
An Office Action dated Jan. 3, 2020, which issued during the prosecution of U.S. Appl. No. 16/678,355.
An Office Action dated Feb. 6, 2020, which issued during the prosecution of U.S. Appl. No. 15/668,659.
An Office Action dated Sep. 6, 2018, which issued during the prosecution of U.S. Appl. No. 15/994,022.
An Office Action dated Sep. 7, 2018, which issued during the prosecution of U.S. Appl. No. 15/995,725.
An International Search Report and a Written Opinion both dated Mar. 27, 2018, which issued during the prosecution of Applicant's PCT/IL2017/050849.
Notice of Allowance dated Oct. 5, 2018, which issued during the prosecution of U.S. Appl. No. 15/886,517.
An Office Action dated Oct. 12, 2018, which issued during the prosecution of U.S. Appl. No. 15/970,314.
An Office Action dated May 11, 2018, which issued during the prosecution of U.S. Appl. No. 15/899,858.
An Office Action dated Jul. 26, 2018, which issued during the prosecution of U.S. Appl. No. 15/979,686.
An Office Action dated Sep. 10, 2018, which issued during the prosecution of U.S. Appl. No. 16/008,618.
European Search Report dated Jun. 10, 2021 which issued during the prosecution of Applicant's European App No. 21157988.3.
An Invitation to pay additional fees dated May 19, 2021, which issued during the prosecution of Applicant's PCT/IL2021/050132.
An International Search Report and a Written Opinion both dated Jul. 12, 2021, which issued during the prosecution of Applicant's PCT/IL2021/050132.
IPR2021-00383 Petitioners' Authorized Reply to Patent Owner's Preliminary Response dated May 27, 2021.
Exhibit 1014—Transcript of proceedings held May 20, 2021 (*Edwards Lifesciences* vs. *Cardiovalve*).
Exhibit 1015—Facilitate, Meriam-Webster.com, https://www.merriamwebster.com/dictionary/facilitate (visited May 26, 2021).
Patent Owner's Authorized Surreply to Petitioner's Reply to Patent Owner's Preliminary Response dated Jun. 4, 2021 (*Edwards Lifesciences* vs. *Cardiovalve*).
An Office Action dated Aug. 18, 2021, which issued during the prosecution of U.S. Appl. No. 17/210,183.
Institution decision dated Jul. 20, 2021 (*Edwards Lifesciences* vs. *Cardiovalve*).
Office Action dated Sep. 9, 2021 for U.S. Appl. No. 16/768,909 (pp. 1-8).
Notice of Allowance dated May 26, 2021, which issued during the prosecution of U.S. Appl. No. 16/135,599.
Office Action dated Oct. 14, 2021, which issued during the prosecution of U.S. Appl. No. 16/680,739.
An Office Action dated Oct. 21, 2021, which issued during the prosecution of U.S. Appl. No. 17/335,845.
European Search Report dated Oct. 11, 2021 which issued during the prosecution of Applicant's European App No. 21176010.3.
Fann, James I., et al. "Beating heart catheter-based edge-to-edge mitral valve procedure in a porcine model: efficacy and healing response." Circulation 110.8 (2004): 988-993.
Feldman, Ted, et al. "Percutaneous mitral repair with the MitraClip system: safety and midterm durability in the initial EVEREST (Endovascular Valve Edge-to-Edge Repair Study) cohort." Journal of the American College of Cardiology 54.8 (2009): 686-694.
IPR2021-00383 Patent Owner's Contingent Motion To Amend Under 37 C.F.R. 42.121 dated Oct. 13, 2021.
IPR2021-00383 Patent Owner's Response Pursuant To 37 C.F.R. 42.120 dated Oct. 13, 2021.
IPR2021-00383 Second Declaration of Dr. Michael Sacks dated Oct. 13, 2021.
An Office Action dated Oct. 21, 2021, which issued during the prosecution of U.S. Appl. No. 17/306,231.
Maisano, Francesco, et al. "The evolution from surgery to percutaneous mitral valve interventions: the role of the edge-to-edge technique." Journal of the American College of Cardiology 58.21 (2011): 2174-2182.
IPR2021-00383 Deposition of Dr. Ivan Vesely, dated Sep. 22, 2021.
Cardiovalve Exhibit 2009—Percutaneous Mitral Leaflet Repair: MitraClip® Therapy for Mitral Regurgitation (2012).
Feldman, Ted, et al. "Percutaneous mitral valve repair using the edge-to-edge technique: six-month results of the EVEREST Phase I Clinical Trial." Journal of the American College of Cardiology 46.11 (2005): 2134-2140.
An Office Action summarized English translation and Search Report dated Oct. 8, 2021, which issued during the prosecution of Chinese Patent Application No. 201780061210.3.
An Office Action dated Nov. 4, 2021, which issued during the prosecution of U.S. Appl. No. 17/366,711.
An Office Action summarized English translation and Search Report dated Aug. 12, 2021, which issued during the prosecution of Chinese Patent Application No. 201880058940.2.
Petitioners' Opposition to Patent Owner's Contingent Motion to Amend, Filed Jan. 5, 2022, *Edwards Lifesciences Corporation and Edwards Lifesciences LLC* v. *Cardiovalve Ltd.*, IPR2021-00383, 32 pages.
Petitioners' Reply to Patent Owner's Reponse, Filed Jan. 5, 2022, *Edwards Lifesciences Corporation and Edwards lifesciences LLC* v. *Cardiovalve Ltd.*, IPR2021-00383, 41 pages.
Notice of Allowance dated Dec. 6, 2021, issued for U.S. Appl. No. 16/738,516, 30 pages.
Notice of Allowance dated Dec. 29, 2021, issued for U.S. Appl. No. 17/210,183, 13 pages.
Notice of Allowance dated Dec. 7, 2021, issued for U.S. Appl. No. 17/394,807, 115 pages.
Non-Final Office Action dated Jan. 12, 2022, issued for U.S. Appl. No. 17/101,787, 17 pages.
European Patent Office Communication pursuant to Rule 164(2)(b) and Article 94(3) EPC for App. No. EP18826823.9, dated Nov. 25, 2021, 14 pages.
European Patent Office Communication pursuant to Article 94(3) EPC for App. No. EP20714289.4, dated Sep. 22, 2021, 5 pages.
Decision Granting Institution of Inter Partes Review 35 USC §314, dated Dec. 10, 2021, *Edwards Lifesciences Corporation and Edwards Lifesciences LLC* v. *Cardiovalve Ltd.*, IPR2021-00383, 42 pages.
English translation of Chinese Office Action issued for CN201880064313.X, dated Jan. 6, 2022, 3 pages.
Office Action (Notice of Allowance and Fees Due (PTOL-85)) dated Mar. 4, 2022 for U.S. Appl. No. 16/768,909 (pp. 1-29).
An Office Action dated Sep. 29, 2022, which issued during the prosecution of U.S. Appl. No. 17/010,886.
An Office Action dated Sep. 29, 2022, which issued during the prosecution of U.S. Appl. No. 16/656,790.
An Office Action dated Nov. 2, 2022, which issued during the prosecution of U.S. Appl. No. 17/004,693.
An Office Action dated Nov. 28, 2022, which issued during the prosecution of U.S. Appl. No. 17/141,853.
An Office Action dated Oct. 19, 2022, which issued during the prosecution of U.S. Appl. No. 17/875,589.
An Office Action dated Oct. 26, 2022, which issued during the prosecution of U.S. Appl. No. 16/746,489.
An Office Action dated Mar. 29, 2021, which issued during the prosecution of U.S. Appl. No. 16/738,516.
Ando, Tomo, et al. "Iatrogenic ventricular septal defect following transcatheter aortic valve replacement: a systematic review." Heart, Lung and Circulation 25.10 (2016): 968-974.
Urena, Marina, et al. "Transseptal transcatheter mitral valve replacement using balloon-expandable transcatheter heart valves: a step-by-step approach." JACC: Cardiovascular Interventions 10.19 (2017): 1905-1919.
An English summary of an Official Action dated Mar. 29, 2021, which issued during the prosecution of Chinese Patent Application No. 201780061210.3.
An International Search Report and a Written Opinion both dated Jan. 28, 2020, which issued during the prosecution of Applicant's PCT/IL2019/051031.

(56) References Cited

OTHER PUBLICATIONS

An International Preliminary Report on Patentability dated Mar. 9, 2021, which issued during the prosecution of Applicant's PCT/IL2019/051031.
An Office Action dated May 4, 2021, which issued during the prosecution of U.S. Appl. No. 16/636,204.
Notice of Allowance dated May 17, 2021, which issued during the prosecution of U.S. Appl. No. 16/138,129.
Notice of Allowance dated Jun. 4, 2021, which issued during the prosecution of U.S. Appl. No. 16/802,353.
An Office Action dated May 12, 2021, which issued during the prosecution of Canadian Patent Application No. 2,973,940.
Petition for Inter Partes Review of U.S. Pat. No. 10,702,385—dated Jun. 4, 2021.
Declaration of Ivan Vesely, Ph.D. In Support of Petition for Inter Partes Review of U.S. Pat. No. 10,702,385—dated Jun. 4, 2021.
An Office Action dated Dec. 24, 2020, which issued during the prosecution of U.S. Appl. No. 16/144,054.
An Office Action dated Feb. 2, 2021, which issued during the prosecution of U.S. Appl. No. 16/811,732.
An Office Action dated Jan. 13, 2021, which issued during the prosecution of European Patent Application No. 15751089.2.
Maisano, F., et al. "The edge-to-edge technique: a simplified method to correct mitral insufficiency." European journal of cardio-thoracic surgery 13.3 (1998): 240-246.
Declaration of Dr. Ivan Vesely, Ph.D. in Support of Petition for Inter Partes Review of U.S. Pat. No. 10,226,341—dated Dec. 17, 2020.
Petition for Inter Partes Review of U.S. Pat. No. 10,226,341 and EXHIBITS 1001-1013—dated Dec. 29, 2020.
An Office Action together with an English summary dated Mar. 3, 2021, which issued during the prosecution of Chinese Patent Application No. 201780047391.4.
Fucci, C, et al. "Improved results with mitral valve repair using new surgical techniques." European journal of cardio-thoracic surgery 9.11 (1993): 621-627.
U.S. Appl. No. 60/128,690, filed Apr. 9, 1999.
Declaration of Ivan Vesely, Ph.D., in Support of Petition for Inter Partes Review of U.S. Pat. No. 7,563,267—dated May 29, 2019.
Batista, Randas JV, et al. "Partial left ventriculectomy to treat end-stage heart disease." The Annals of thoracic surgery 64.3 (1997): 634-638.
Beall Jr. Arthur C, et al. "Clinical experience with a dacron velour-covered teflon-disc mitral valve prosthesis." The Annals of thoracic surgery 5.5 (1968): 402-410.
Mitral Valve Academic Research Consortium. "Clinical Trial Design Principles and Endpoint Definitions for Transcatheter Mitral Valve Repair and Replacement: Part 1: Clinical Trial Design Principles A Consensus Document from the Mitral Valve Academic Research Consortium." Journal of the American College of Cardiology 66.3 (2015): 278-307.
Kalbacher, D., et al. "1000 MitraClip™ procedures: Lessons learnt from the largest single-centre experience worldwide." (2019): 3137-3139.
U.S. Appl. No. 60/613,867, filed Sep. 27, 2004.
An International Preliminary Report on Patentability dated Oct. 20, 2020, which issued during the prosecution of Applicant's PCTYIL2019/050142.
An Office Action dated Oct. 5, 2020, which issued during the prosecution of Canadian Patent Application No. 2.973,940.
Notice of Allowance dated Nov. 19, 2020, which issued during the prosecution of U.S. Appl. No. 16/318,025.
An Office Action dated Sep. 24, 2020. which issued during the prosecution of U.S. Appl. No. 16/811,732.
An Office Action summarized English translation and Search Report dated Nov. 25, 2020, which issued during the prosecution of Chinese Patent Application No. 201910449820.1.
An Office Action dated Nov. 30, 2020, which issued during the prosecution of U.S. Appl. No. 16/138,129.
Sundermann, Simon H., et al. "Feasibility of the Engager™ aortic transcatheter valve system using a flexible over-the-wire design." European Journal of Cardio-Thoracic Surgery 42.4 (2012): e48-e52.
Serruys, P. W., Piazza, N., Cribier, A., Webb, J., Laborde, J. C, & de Jaegere, P. (Eds.). (2009). Transcatheter aortic valve implantation: tips and tricks to avoid failure. CRC Press.—Screenshots from Google Books downloaded from: https://books.google.co.il/books ?id=FLzLBQAAQBAJ&lpg=PA198&ots=soqWr DH-y_&dq=%20%22Edwards%20SAPIEN%22&Ir&pg=PA20#v=onepage&q=%22E dwards%20SAPIEN%22&f=false ; Downloaded on Jun. 18, 2020.
Notice of Allowance dated May 7, 2020, which issued during the prosecution of U.S. Appl. No. 16/637,166.
Notice of Allowance dated Sep. 10, 2020, which issued during the prosecution of U.S. Appl. No. 15/600,190.
Notice of Allowance dated Jul. 29, 2020, which issued during the prosecution of U.S. Appl. No. 16/132,937.
An International Search Report and a Written Opinion both dated Jun. 24, 2020, which issued during the prosecution of Applicant's PCT/IL2019/051398.
An Office Action dated Jul. 29, 2020, which issued during the prosecution of U.S. Appl. No. 16/269,328.
Notice of Allowance dated Aug. 26, 2020, which issued during the prosecution of U.S. Appl. No. 16/269,328.
An Office Action dated Jul. 14, 2020, which issued during the prosecution of U.S. Appl. No. 16/324,339.
Notice of Allowance dated Aug. 28, 2020, which issued during the prosecution of U.S. Appl. No. 16/324,339.
An Office Action summarized English translation and Search Report dated Jul. 3, 2020, which issued during the prosecution of Chinese Patent Application No. 201780061210.3.
An Office Action dated Nov. 23, 2012, which issued during the prosecution of U.S. Appl. No. 13/033,852.
An Office Action dated Dec. 31, 2012, which issued during the prosecution of U.S. Appl. No. 13/044,694.
An Office Action dated Feb. 6, 2013, which issued during the prosecution of U.S. Appl. No. 13/412,814.
Langer F et al., "RING plus STRING: Papillary muscle repositioning as an adjunctive repair technique for ischemic mitral regurgitation," J Thorac Cardiovasc Surg 133:247-9, Jan. 2007.
Langer F et al., "RING+STRING: Successful repair technique for ischemic mitral regurgitation with severe leaflet tethering," Circulation 120[suppl 1]: S85-S91, Sep. 2009.
"Transcatheter Valve-in-Valve Implantation for Failed Bioprosthetic Heart Valves", J Webb et al., Circulation. Apr. 2010; 121: 1848-1857.
An Office Action dated Nov. 27, 2015, which issued during the prosecution of U.S. Appl. No. 14/626,267.
An Office Action dated Jan. 21, 2016, which issued during the prosecution of U.S. Appl. No. 14/237,264.
An Office Action dated Jan. 30, 2015, which issued during the prosecution of UK Patent Application No. 1413474.6.
An International Search Report and a Written Opinion both dated May 30, 2016, which issued during the prosecution of Applicant's PCT/IL2016/050125.
An Office Action dated Sep. 26, 2016, which issued during the prosecution of U.S. Appl. No. 14/763,004.
An Office Action dated Jan. 18, 2017, which issued during the prosecution of U.S. Appl. No. 14/626,267.
An Office Action dated Feb. 7, 2017, which issued during the prosecution of U.S. Appl. No. 14/689,608.
An Office Action dated Feb. 8, 2017, which issued during the prosecution of UK Patent Application No. 1613219.3.
An Office Action together dated Feb. 10, 2017, which issued during the prosecution of European Patent Application No. 12821522.5.
An International Search Report and a Written Opinion both dated Oct. 27, 2015, which issued during the prosecution of Applicant's PCT/IL2015/050792.
European Search Report dated Feb. 18, 2015, which issued during the prosecution of Applicant's European App No. 12821522.5.
Saturn Project—a novel solution for transcatheter heart valve replacement specifically designed to address clinical therapeutic needs on mitral valve: Dec. 2016.

(56) References Cited

OTHER PUBLICATIONS

Righini presentation EuroPCR May 2015 (Saturn)-(downloaded from: https://www.pcronline.com/Cases-resourcesimages/Resources/Course-videos-slides/2015/Cardiovascularinnovation-pipeline-Mitral-and-tricuspid-valve-interventions).
An Advisory Action dated Apr. 2, 2018, which issued during the prosecution of U.S. Appl. No. 14/763,004.
An Office Action dated Jul. 26, 2018, which issued during the prosecution of U.S. Appl. No. 15/872,501.
An Office Action dated May 4, 2018, which issued during the prosecution of U.S. Appl. No. 15/872,501.
An Office Action dated Apr. 20, 2018, which issued during the prosecution of U.S. Appl. No. 15/886,517.
An Office Action dated Aug. 9, 2018, which issued during the prosecution of U.S. Appl. No. 15/899,858.
An Office Action dated Aug. 9, 2018, which issued during the prosecution of U.S. Appl. No. 15/902,403.
An Office Action dated Jun. 28, 2018, which issued during the prosecution of US Design U.S. Appl. No. 29/635,658.
An Office Action dated Jun. 28, 2018, which issued during the prosecution of US Design U.S. Appl. No. 29/635,661.
Georg Lutter, MD, et al.; "Percutaneous Valve Replacement: Current State and Future Prospects", The Annals of Thoracic Surgery ; vol. 78, pp. 2199-2206; Dec. 2004.
An Office Action dated Jun. 6, 2018, which issued during the prosecution of UK Patent Application No. 1720803.4.
International Search Report and Written Opinion issued in PCT Application No. PCT/IL2018/050024 dated Jun. 20, 2018.
An Office Action dated Jun. 18, 2018, which issued during the prosecution of UK Patent Application No. 1800399.6.
An Office Action dated Oct. 23, 2017, which issued during the prosecution of U.S. Appl. No. 14/763,004.
An Office Action dated Dec. 7, 2017, which issued during the prosecution of U.S. Appl. No. 15/213,791.
Interview Summary dated Feb. 8, 2018, which issued during the prosecution of U.S. Appl. No. 15/213,791.
An Office Action dated Feb. 7, 2018, which issued during the prosecution of U.S. Appl. No. 15/197,069.
An Office Action dated Jun. 15, 2018, which issued during the prosecution of U.S. Appl. No. 15/970,314.
An Office Action dated Jan. 5, 2018, which issued during the prosecution of U.S. Appl. No. 15/541,783.
An Office Action dated Feb. 2, 2018, which issued during the prosecution of U.S. Appl. No. 15/329,920.
An Invitation to pay additional fees dated Jan. 2, 2018, which issued during the prosecution of Applicant's PCT7IL2017/050849.
An Invitation to pay additional fees dated Sep. 29, 2017, which issued during the prosecution of Applicant's PCT/IL2017/050873.
European Search Report dated Jun. 29, 2017, which issued during the prosecution of Applicant's European App No. 11809374.9.
An Invitation to pay additional fees dated Oct. 11, 2018, which issued during the prosecution of Applicant's PCT/IL2018/050725.
An Office Action dated Dec. 4, 2018, which issued during the prosecution of U.S. Appl. No. 16/045,059.
An Office Action together with the English translation dated Nov. 5, 2018 which issued during the prosecution of Chinese Patent Application No. 201680008328.5.
Notice of Allowance dated Sep. 25, 2018, which issued during the prosecution of U.S. Appl. No. 15/188,507.
European Search Report dated Sep. 26, 2018 which issued during the prosecution of Applicant's European App No. 18186784.7.
An Office Action dated Jun. 30, 2015, which issued during the prosecution of U.S. Appl. No. 14/522,987.
Notice of Allowance dated Dec. 13, 2013, which issued during the prosecution of U.S. Appl. No. 13/675,119.
An International Preliminary Report on Patentability dated Aug. 8, 2017, which issued during the prosecution of Applicant's PCT/IL2016/050125.
An Office Action dated Jan. 17, 2018, which issued during the prosecution of U.S. Appl. No. 14/763,004.
An Office Action dated Mar. 25, 2015, which issued during the prosecution of U.S. Appl. No. 12/840,463.
An Office Action dated Feb. 25, 2016, which issued during the prosecution of U.S. Appl. No. 14/522,987.
An Office Action dated Apr. 13, 2016, which issued during the prosecution of U.S. Appl. No. 14/626,267.
An Office Action dated Aug. 28, 2015, which issued during the prosecution of U.S. Appl. No. 14/237,264.
Maisano (2015) TCR presentation re Cardiovalve.
Notice of Allowance dated Sep. 29, 2016, which issued during the prosecution of U.S. Appl. No. 14/442,541.
Notice of Allowance dated May 10, 2016, which issued during the prosecution of U.S. Appl. No. 14/237,258.
Notice of Allowance dated May 20, 2016, which issued during the prosecution of U.S. Appl. No. 14/237,258.
An International Preliminary Report on Patentability dated May 19, 2015, which issued during the prosecution of Applicant's PCT/IL2013/050937.
Dusan Pavcnik, MD, PhD2, et al.; "Development and Initial Experimental Evaluation of a Prosthetic Aortic Valve for Transcatheter Placement", Cardiovascular Radiology. Radiology Apr. 1992, vol. 183, pp. 151-154.
Notice of Allowance dated Oct. 16, 2013, which issued during the prosecution of U.S. Appl. No. 13/675,119.
Notice of Allowance dated Feb. 11, 2015, which issued during the prosecution of U.S. Appl. No. 13/033,852.
Notice of Allowance dated May 5, 2015, which issued during the prosecution of U.S. Appl. No. 12/840,463.
Notice of Allowance dated Mar. 10, 2015, which issued during the prosecution of U.S. Appl. No. 13/811,308.
Notice of Allowance dated Jul. 1, 2016, which issued during the prosecution of U.S. Appl. No. 14/442,541.
Office Action dated Mar. 25, 2019, issued in European Patent Application No. 14710060.6, 4 pages.
PCT International Search Report and a Written Opinion dated Nov. 9, 2018, in corresponding Application No. PCT/IL2018/050869, 19 pages.
PCT International Search Report and Written Opinion dated Dec. 5, 2018 in corresponding Application No. PCT/IL2018/050725, 19 pages.
PCT International Search Report and Written Opinion dated Apr. 25, 2019 in corresponding Application No. PCT/IL2019/050142, 12 pages.
PCT International Preliminary Report on Patentability dated Feb. 12, 2019 in corresponding Application No. PCT/IL2017/050873, 13 pages.
An Office Action dated Sep. 13, 2019, which issued during the prosecution of U.S. Appl. No. 16/460,313.
An Office Action dated Nov. 26, 2019, which issued during the prosecution of U.S. Appl. No. 16/532,945.
An Office Action dated Aug. 16, 2019, which issued during the prosecution of U.S. Appl. No. 15/668,659.
An Office Action dated Nov. 1, 2010 which issued during the prosecution of U.S. Appl. No. 15/872,501.
An Office Action dated Jun. 14, 2019, which issued during the prosecution of U.S. Appl. No. 15/703,385.
Office Action dated Oct. 4, 2019, which issued during the prosecution of U.S. Appl. No. 16/183,140.
An Office Action dated Jun. 13, 2019, which issued during the prosecution of U.S. Appl. No. 16/388,038.
PCT International Search Report and Written Opinion dated Jan. 25, 2019 in corresponding Application No. PCT/IL2018/051122, 36 pages.
Office Action dated Oct. 25, 2018, issued in U.S. Appl. No. 14/763,004, 18 pages.
PCT International Search Report and Written Opinion dated May 13, 2019 in corresponding Application No. PCT/IL2018/051350, 17 pages.
PCT International Preliminary Report on Patentability dated Feb. 5, 2019 in corresponding Application No. PCT/IL2017/050849, 12 pages.
Notice of Allowance dated Jan. 13, 2020, which issued during the prosecution of U.S. Appl. No. 15/956,956.

(56) References Cited

OTHER PUBLICATIONS

Office Action dated Mar. 4, 2019, issued in U.S. Appl. No. 14/763,004, 29 pages.
Office Action dated Jan. 9, 2019, issued in U.S. Appl. No. 15/329,920, 19 pages.
Office Action dated Jan. 30, 2019, issued in U.S. Appl. No. 15/872,501, 34 pages.
Office Action dated Feb. 5, 2019, issued in U.S. Appl. No. 15/899,858, 24 pages.
Office Action dated May 23, 2019, issued in U.S. Appl. No. 15/668,659, 19 pages.
Office Action dated Aug. 1, 2019, which issued during the prosecution of U.S. Appl. No. 15/668,559.
An Office Action dated Jun. 19, 2019, which issued during the prosecution of U.S. Appl. No. 15/682,789.
An Office Action dated Jun. 25, 2019, which issued during the prosecution of U.S. Appl. No. 15/329,920.
An Office Action dated May 16, 2019, which issued during the prosecution of U.S. Appl. No. 15/433,547.
U.S. Appl. No. 62/112,343, filed Feb. 5, 2015.
An Office Action dated Nov. 16, 2018, which issued during the prosecution of U.S. Appl. No. 16/042,028.
An Office Action dated May 8, 2018, which issued during the prosecution of U.S. Appl. No. 15/902,403.
Tchetche, D. and Nicolas M. Van Mieghem: "New-generation TAVI devices: description and specifications" EuroIntervention, 2014, No. 10:U90-U100.
An Office Action dated Jan. 6, 2020, which issued during the prosecution of U.S. Appl. No. 16/660,231.
An Advisory Action dated Jan. 2, 2020, which issued during the prosecution of U.S. Appl. No. 15/668,659.
Notice of Allowance dated Jul. 19, 2019, which issued during the prosecution of U.S. Appl. No. 15/899,858.
An Office Action dated Nov. 23, 2018, which issued during the prosecution of U.S. Appl. No. 16/041,208.
An Office Action dated Jul. 11, 2018, which issued during the prosecution of U.S. Appl. No. 15/978,494.
Symetis S.A.: "ACURATE neo™ Aortic Bioprosthesis for Implantation using the ACURATE neo™ TA Transapical Delivery System in Patients with Severe Aortic Stenosis," Clinical Investigation Plan, Protocol No. 2015-01, Vs. No. 2, 2015:1-76.
An Office Action dated Nov. 26, 2018, which issued during the prosecution of U.S. Appl. No. 16/040,831.
An Office Action dated Dec. 31, 2019, which issued during the prosecution of U.S. Appl. No. 16/183,140.
An Office Action dated Jan. 14, 2020, which issued during the prosecution of U.S. Appl. No. 16/284,331.
European Search Report dated Mar. 5, 2020 which issued during the prosecution of Applicant's European App No. 17752184.6.
An Office Action dated Mar. 4, 2020, which issued during the prosecution of European Patent Application No. 16706913.7.
An Office Action dated Sep. 21, 2022, which issued during the prosecution of U.S. Appl. No. 16/776,581. 142 pages.
An Office Action dated Jul. 20, 2022, which issued during the prosecution of U.S. Appl. No. 17/101,787. 26 pages.
An Office Action dated Sep. 16, 2022, which issued during the prosecution of U.S. Appl. No. 16/135,466. 19 pages.
An Office Action dated Aug. 1, 2022, which issued during the prosecution of European Patent Application No. 18826823.9. 5 pages.
European Search Report dated Sep. 6, 2022 which issued during the prosecution of Applicant's European App No. 22161862.2. 6 pages.
IPR2021-01051 Petitioners' Reply To Preliminary Guidance dated Aug. 2, 2022, 17 pages.
IPR2021-01051 Patent Owner's Sur-Reply To Petitioners' Reply To Preliminary Guidance dated Aug. 23, 2022, 10 pages.
An Office Action dated Aug. 5, 2022, which issued during the prosecution of U.S. Appl. No. 16/760,147. 137 pages.
An Office Action dated Sep. 8, 2022, which issued during the prosecution of U.S. Appl. No. 16/896,858. 116 pages.
An Office Action dated Jul. 27, 2022, which issued during the prosecution of U.S. Appl. No. 16/881,350. 176 pages.

\* cited by examiner

PROSTHETIC VALVE AND DELIVERY TOOL THEREFOR

CROSS-REFERENCES TO RELATED APPLICATIONS

The present application is a Continuation of U.S. Ser. No. 16/768,909 to Hariton et al., filed Jun. 2, 2020, and entitled "PROSTHETIC VALVE AND DELIVERY TOOL THEREFOR," which issued as U.S. Pat. No. 11,382,746, and which is the US National Phase of PCT application IL2018/051350 to Hariton et al., filed Dec. 12, 2018, and entitled "PROSTHETIC VALVE AND DELIVERY TOOL THEREFOR," which published as WO/2019/116369, and which claims priority from UK patent application GB 1720803.4, filed Dec. 13, 2017, and entitled "Prosthetic valve and delivery tool therefor."

Each of the applications mentioned above is assigned to the assignee of the present application and is incorporated herein by reference.

FIELD OF THE INVENTION

Some applications of the present invention relate in general to percutaneous delivery of medical implants. More specifically, some applications of the present invention relate to prosthetic cardiac valves and techniques for implantation thereof.

BACKGROUND

Dilation of the annulus of a heart valve, such as that caused by ischemic heart disease, prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF THE INVENTION

An implant is provided having self-expanding portions, and non-self-expanding portions. The implant comprises a non-self-expanding tubular frame, which is balloon-expandable. The implant further comprises an outer frame, which comprises self-expanding flanges and a self-expanding upstream support portion. The self-expanding nature of the flanges and upstream support portion is provided by the outer frame being composed of a shape-memory alloy. The tubular frame is composed of a different material.

The outer frame is coupled to the tubular frame via pins that are composed of the same material as the tubular frame. One end of each pin is secured to the outer frame by a head of the pin. The other end of each pin is secured to the tubular frame by welding.

A delivery tool comprises a capsule that has two capsule-portions, one to constrain the flanges, and one to constrain the upstream support portion. The delivery tool further comprises a balloon, disposed within the tubular frame. At the implantation site, the flanges and upstream support portion are released from the capsule, and automatically deflect radially outwards. Subsequently, the balloon is inflated to radially expand the tubular frame.

The delivery tool further comprises projections, which are sufficiently rigid to axially push the tubular frame in order to press the flanges against tissue at the implantation site, but which are sufficiently flexible to not inhibit inflation of the balloon.

There is therefore provided, in accordance with an application of the present invention, apparatus for use at a native valve of a heart of a subject, the apparatus including:
  a delivery tool, including:
    a shaft, having a shaft-axis;
    a capsule, disposed at a distal portion of the tool, and including an upstream capsule-portion and a downstream capsule-portion, the capsule being openable by moving the upstream capsule-portion and the downstream capsule-portion apart; and
    a balloon, coupled to the shaft, and disposed within the capsule; and
  a prosthetic valve, including:
    a tubular frame, compressed around the balloon, and disposed within the capsule;
    one or more shape-memory flanges, constrained within the downstream capsule-portion; and
    a shape-memory upstream support portion, constrained within the upstream capsule-portion,
and:
  the flanges are configured to automatically deflect radially outward upon exposure from the downstream capsule-portion,
  the upstream support portion is configured to automatically deflect radially outward upon exposure from the upstream capsule-portion,
  the tubular frame is configured to remain compressed around the balloon upon exposure of the tubular frame from the capsule, and
  while the tubular frame is exposed from the capsule, inflation of the balloon plastically expands the tubular frame radially.

In an application, the prosthetic valve further includes one or more prosthetic valve leaflets disposed within the lumen and coupled to the tubular frame.

In an application, the tubular frame is disposed within the downstream capsule-portion of the capsule.

In an application, the tubular frame is composed of a material that is not a shape-memory alloy.

In an application, the tubular frame is composed of steel.

In an application, the tubular frame is composed of cobalt chrome.

In an application, the flanges are composed of a shape-memory alloy.

In an application, the flanges are composed of nickel titanium.

In an application, the balloon is fixed to the shaft.

In an application, both the upstream capsule-portion and the downstream capsule-portion are axially movable with respect to the shaft.

In an application:
  a first capsule-portion selected from the group consisting of: the upstream capsule-portion and the downstream capsule-portion is attached to a tube, and is axially movable with respect to the shaft by the tube being slid over the shaft, and
  a second capsule-portion selected from the group is attached to a rod, and is axially movable with respect to the shaft by the rod being slid though the shaft.

In an application, the upstream capsule-portion is retractable from over the upstream support portion by being moved away from the balloon, and the downstream capsule-portion is retractable from over the flanges by being moved away from the balloon.

In an application, the delivery tool further includes one or more elongate projections disposed within the downstream capsule-portion, each of the projections having (i) a tip-portion, and (ii) a base-portion, disposed deeper than the tip-portion into the downstream capsule-portion, the projections arranged circumferentially around the shaft-axis such that the tip-portions are arranged circumferentially around a downstream balloon-portion of the balloon, with the tip-portion of each projection being closer than its corresponding base-portion to the tubular frame.

In an application, each of the projections is sufficiently stiff that, when pushed against the tubular frame, it is capable of applying, to the tubular frame, an axial pushing force of at least 0.5 N.

In an application, each of the projections is sufficiently stiff that, when pushed against the tubular frame, the one or more projections are capable collectively of applying, to the tubular frame, an axial pushing force of at least 3 N.

In an application, when pushed against the tubular frame, the one or more projections are capable collectively of applying, to the tubular frame, an axial pushing force of at least 3 N and no more than 100 N.

In an application, when pushed against the tubular frame, the one or more projections are capable collectively of applying, to the tubular frame, an axial pushing force of at least 3 N and no more than 30 N.

In an application, when pushed against the tubular frame, the one or more projections are capable collectively of applying, to the tubular frame, an axial pushing force of at least 6 N and no more than 30 N.

In an application, when pushed against the tubular frame, the one or more projections are capable collectively of applying, to the tubular frame, an axial pushing force of at least 40 N and no more than 100 N.

In an application, when pushed against the tubular frame, the one or more projections are capable collectively of applying, to the tubular frame, an axial pushing force of at least 40 N and no more than 80 N.

In an application, when pushed against the tubular frame, the one or more projections are capable collectively of applying, to the tubular frame, an axial pushing force of at least 60 N and no more than 100 N.

In an application, the tubular frame is disposed within the downstream capsule-portion of the capsule, and the downstream capsule-portion is retractable from over the tubular frame and at least the tip-portions, exposing, from the downstream capsule-portion, the tubular frame and at least the tip-portions.

In an application, while the tubular frame and the tip-portions are exposed from the downstream capsule-portion, inflation of the balloon (i) radially expands the tubular frame, and (ii) deflects each of the projections radially outward within a respective radial plane on which the shaft-axis and the projection lie.

In an application, while the tubular frame and the tip-portions are exposed from the downstream capsule-portion, inflation of the balloon uniformly fills the lumen of the tubular frame.

In an application, a widest part of the balloon is disposed within the lumen.

In an application, each projection has a radial stiffness in its radial plane, and has a lateral stiffness in a respective lateral plane, the lateral stiffness being greater than the radial stiffness.

In an application:
the balloon has an upstream balloon-portion, a downstream balloon-portion, and a body balloon-portion therebetween,
the tubular frame is compressed around the body balloon-portion, and
while the tubular frame and the tip-portions are exposed from the downstream capsule-portion, inflation of the balloon (i) radially expands the tubular frame by pressing the body balloon-portion radially outward against the tubular frame, and (ii) deflects the projections radially outward by pressing the downstream balloon-portion radially outward against the projections.

In an application, the downstream balloon-portion of the balloon extends away from the tubular frame, and is tapered.

In an application, the upstream balloon-portion of the balloon extends away from the tubular frame, and is tapered.

In an application, the tip-portion of each of the projections abuts the tubular frame, and the apparatus is configured such that the tip-portion of each of the projections remains in contact with the tubular frame as the balloon is inflated.

In an application, a downstream end of the tubular frame defines a frame-circumference, the tip-portions define a projection-circumference, and while the tubular frame and the tip-portions are exposed from the downstream capsule-portion, inflation of the balloon increases the projection-circumference at the same rate as the balloon increases the frame-circumference.

In an application, the tip-portion of each of the projections abuts the tubular frame.

In an application, the projections are not attached to the tubular frame.

There is further provided, in accordance with an application of the present invention, apparatus for delivery of a prosthetic heart valve to an annulus of a native heart valve, the apparatus including:
a shaft, having a longitudinal shaft-axis;
an inflatable balloon, disposed at a distal end of the shaft; and
one or more projections extending distally from the shaft, such that the projections are arranged around a proximal portion of the balloon,
and:
inflation of the balloon causes radial expansion of the balloon, the radial expansion of the balloon applying a radial force to each of the projections, and
each of the projections is sufficiently radially flexible that the radial force deflects the projections radially outward.

In an application, for each of the projections:
the projection defines:
a respective radial plane on which the shaft-axis and the projection lie, and within which the projection deflects in response to the radial force, and
a lateral plane, tangential to the circumference, and on which the projection lies,
the projection has a radial stiffness, in its radial plane, and the projection has a lateral stiffness, in its lateral plane, that is greater than the radial stiffness.

In an application, the apparatus further includes a tubular frame at the distal end of the shaft, the tubular frame defining a longitudinal lumen, and the balloon is disposed within the lumen.

In an application, each of the projections is sufficiently stiff that it is capable of applying, to the tubular frame, an axial pushing force of at least 0.5 N.

In an application, each of the projections is sufficiently stiff that the one or more projections are capable collectively of applying, to the tubular frame, an axial pushing force of at least 3 N.

In an application, the apparatus further includes one or more prosthetic valve leaflets disposed within the lumen and coupled to the tubular frame.

In an application, the balloon:
has a longitudinal balloon-axis, collinear with the longitudinal shaft-axis, the balloon-axis extending through the lumen,
has (i) a deflated state, and (ii) an inflated state in which the balloon has a widest part, and
is positioned with respect to the tubular frame such that the widest part is within the lumen.

In an application, the balloon, in its inflated state, uniformly fills the lumen.

In an application, in the inflated state of the balloon, the proximal portion of the balloon tapers proximally away from the tubular frame.

In an application, the balloon, in its inflated state, has a tapered distal portion that tapers distally away from the tubular frame.

In an application, the widest part of the balloon is disposed longitudinally between the proximal portion and the distal portion.

In an application, each of the projections has a tip-portion that abuts a proximal surface of the tubular frame.

In an application, the tip-portion of each of the projections is not attached to the tubular frame.

In an application, inflation of the balloon simultaneously increases (i) a radial distance between the tip-portion of one of the projections and the tip-portion of an opposite one of the projections, and (ii) a circumference of the tubular frame.

There is further provided, in accordance with an application of the present invention, apparatus for use in a heart of a subject, the apparatus including:
a tubular frame that circumscribes a longitudinal axis to define a lumen along the longitudinal axis;
a valve member, disposed within the lumen and coupled to the tubular frame;
an outer frame:
  disposed radially outward from the tubular frame,
  including a flange, and
  defining an eyelet; and
a pin:
  defining a shaft and a head, and
  coupling the outer frame to the tubular frame,
and:
the outer frame is composed of a shape-memory alloy,
the tubular frame and the pin are composed of a material that is not the shape-memory alloy,
the head is disposed against the outer frame, radially outward from the eyelet,
the shaft extends from the head through the eyelet to the tubular frame, and
the shaft is welded to the tubular frame.

In an application, the outer frame further includes an upstream support portion, shape-set to extend radially outward from the tubular frame.

In an application, the flange is shape-set to extend radially outward from the tubular frame.

In an application, the outer frame further includes an upstream support portion, upstream support portion is shape-set to extend radially outward from the tubular frame, and the flange is shape-set to extend radially outward from the tubular frame and toward the upstream support portion.

In an application:
the flange has a root-portion and a tip, and extends away from the tubular frame from the root-portion to the tip,
the eyelet is defined at the root-portion of the flange, and
the head is disposed against the root-portion of the flange, radially outward from the eyelet.

In an application, the eyelet is an outer eyelet, and the tubular frame defines an inner eyelet, the shaft extending through the inner eyelet.

In an application, the shape-memory alloy is nickel titanium.

In an application, the material is not a shape-memory material.

In an application, the material is steel.

In an application, the material is cobalt chrome.

In an application, the flange is one of a plurality of flanges, and the outer frame includes the plurality of flanges, and circumscribes the tubular frame.

In an application, the eyelet is one of a plurality of eyelets, and the outer frame defines the plurality of eyelets.

In an application, the flanges of the plurality of flanges are equal in number to the eyelets of the plurality of eyelets.

In an application, the eyelet is one of a plurality of eyelets, and the root-portion of each flange of the plurality of flanges defines a respective eyelet of the plurality of eyelets.

There is further provided, in accordance with an application of the present invention, a method for constructing a prosthetic heart valve, the method including:
from a tube of a shape-memory alloy, cutting an outer frame that includes a flange and defines an eyelet;
from a tube of a material that is not the shape-memory alloy, cutting a tubular frame that circumscribes a longitudinally axis to define a lumen along the longitudinal axis;
positioning the outer frame against the tubular frame, radially-outward from the tubular frame;
passing a shaft of a pin through the eyelet such that (i) the shaft of the eyelet extends to the tubular frame, and (ii) a head of the pin is disposed against the outer frame radially outward from the eyelet, the pin being composed of the material;
welding the shaft to the tubular frame;
lining at least part of the lumen with a lining; and
securing a plurality of prosthetic leaflets within the lumen.

In an application, the method further includes shape-setting the flange to extend radially outward.

In an application:
cutting the outer frame includes cutting the outer frame such that the flange has a root-portion and a tip, and defines the eyelet at the root-portion, and
passing the shaft of the pin through the eyelet such that the head of the pin is disposed against the outer frame radially outward from the eyelet, includes passing the shaft of the pin through the eyelet such that the head of the pin is disposed against the root-portion of the flange, radially outward from the eyelet.

In an application:
the eyelet is an outer eyelet, and cutting the tubular frame includes cutting the tubular frame such that the tubular frame defines an inner eyelet, and
the step of passing the shaft includes passing the shaft through the outer eyelet and through the inner eyelet, and
welding the shaft to the tubular frame includes welding the shaft to the tubular frame at the inner eyelet.

In an application, the shape-memory alloy is nickel titanium, and cutting the outer frame from the tube of the shape-memory alloy includes cutting the outer frame from a tube of nickel titanium.

In an application, the material is not a shape-memory material, and cutting the tubular frame includes cutting the tubular frame from the material that is not a shape-memory material.

In an application, the material is steel, and cutting the tubular frame from the tube of the material includes cutting the tubular frame from a tube of steel.

In an application, the material is cobalt chrome, and cutting the tubular frame from the tube of the material includes cutting the tubular frame from a tube of cobalt chrome.

In an application, cutting the outer frame includes cutting the outer frame that further includes an upstream support portion.

In an application, the method further includes shape-setting the upstream support portion to extend radially outward.

In an application:
the flange is one of a plurality of flanges,
cutting the outer frame includes cutting the outer frame such that the outer frame defines the plurality of flanges, and
positioning the outer frame includes positioning the outer frame such that the outer frame circumscribes the tubular frame.

In an application, the eyelet is one of a plurality of eyelets, and cutting the outer frame includes cutting the outer frame such that the outer frame defines the plurality of eyelets.

In an application, cutting the outer frame includes cutting the outer frame such that the outer frame has an equal number of flanges and eyelets.

There is further provided, in accordance with an application of the present invention, a method for use at a native valve of a heart of a subject, the method including:
advancing, to the heart, an implant that includes a tubular frame, the tubular frame disposed on a distal portion of a tool, the distal portion of the tool including:
a distal end of a shaft,
an inflatable balloon, having a body portion that is disposed within the tubular frame,
one or more projections extending, from the shaft, distally over at least a proximal portion of the balloon toward the tubular frame, the proximal portion of the balloon being proximal from the body balloon-portion of the balloon;
pushing the projections distally against the tubular frame to apply a distal pushing force to the tubular frame; and
while maintaining contact between the projections and the tubular frame, inflating the balloon such that:
radial expansion of the body balloon-portion radially expands the tubular frame, and
radial expansion of the proximal portion deflects the projections radially outward.

In an application, pushing the projections distally against the tubular frame comprises pushing the projections distally against the tubular frame such that the projections collectively apply a distal pushing force of at least 3 N to the tubular frame.

In an application, pushing the projections distally against the tubular frame comprises pushing the projections distally against the tubular frame such that the projections collectively apply a distal pushing force of at least 3 N and no more than 100 N.

In an application, pushing the projections distally against the tubular frame comprises pushing the projections distally against the tubular frame such that the projections collectively apply a distal pushing force of at least 3 N and no more than 30 N.

In an application, pushing the projections distally against the tubular frame comprises pushing the projections distally against the tubular frame such that the projections collectively apply a distal pushing force of at least 6 N and no more than 30 N.

In an application, pushing the projections distally against the tubular frame comprises pushing the projections distally against the tubular frame such that the projections collectively apply a distal pushing force of at least 40 N and no more than 100 N.

In an application, pushing the projections distally against the tubular frame comprises pushing the projections distally against the tubular frame such that the projections collectively apply a distal pushing force of at least 40 N and no more than 80 N.

In an application, pushing the projections distally against the tubular frame comprises pushing the projections distally against the tubular frame such that the projections collectively apply a distal pushing force of at least 60 N and no more than 100 N.

In an application:
the implant includes one or more self-expanding flanges,
the tool distal portion of the tool includes a capsule;
advancing the implant includes advancing the tubular frame while at least the flanges are disposed within, and constrained by, the capsule,
the method further includes, prior to pushing the projections distally, allowing the flanges to self-expand by exposing the flanges from the capsule, and
the step of pushing the projections distally against the tubular frame includes pushing the implant distally such that the flanges press against tissue of the native valve.

In an application, advancing the implant includes advancing the implant while the projections are disposed within the capsule, and exposing the flanges from the capsule includes retracting the capsule proximally with respect to the implant such that the flanges and the projections become exposed from the capsule.

There is further provided, in accordance with an application of the present invention, a method for use at a native valve of a heart of a subject, the method including:
advancing, to the heart:
a distal portion of a delivery tool, the delivery tool including:
a shaft that extends to the distal portion of the delivery tool,
a capsule disposed at the distal portion of the delivery tool, and including an upstream capsule-portion and a downstream capsule-portion, and
a balloon, coupled to the shaft, and disposed at least partly within the capsule, and
an implant disposed within the capsule, and including a tubular frame and one or more shape-memory flanges, the tubular frame compressed around the balloon, and the flanges constrained within the downstream capsule-portion;
exposing the flanges from the downstream capsule-portion such that the flanges automatically deflect radially outward;

subsequently, pressing the flanges against a downstream surface of the native valve by moving the implant in an upstream direction; and while the flanges are in contact with the downstream surface, plastically expanding the tubular frame radially by inflating the balloon.

In an application, plastically expanding the tubular frame includes plastically expanding the tubular frame by radially by inflating the balloon while continuing to press the flanges against the downstream surface.

In an application, exposing the flanges from the downstream capsule-portion includes moving the downstream capsule-portion away from the upstream capsule-portion.

In an application, advancing the implant includes advancing the implant while the tubular frame is disposed within the downstream capsule-portion, and the method further includes exposing the tubular frame from the downstream capsule-portion.

In an application, exposing the tubular frame from the downstream capsule-portion includes exposing the tubular frame from the downstream capsule-portion prior to the step of pressing the flanges.

In an application, exposing the tubular frame from the downstream capsule-portion includes exposing the tubular frame entirely from the downstream capsule-portion without causing the tubular frame to expand.

In an application, the implant further includes a shape-memory upstream support portion, constrained within the upstream capsule-portion, and the method further includes, prior to expanding the tubular frame, exposing the upstream support portion from the upstream capsule-portion such that the upstream support portion automatically deflects radially outward.

In an application, moving the implant in the upstream direction includes moving the implant such that the upstream support portion, constrained within the upstream capsule portion, is disposed upstream of the native valve, and exposing the upstream support portion includes exposing the upstream support portion such that the upstream support portion automatically deflects radially outwards and contacts an upstream surface of the native valve.

In an application:
the implant is compressed around a body balloon-portion of the balloon,
the tool further includes one or more projections, each of the projections having a base-portion and a tip-portion,
the projections extend, from the shaft, over at least a downstream balloon-portion of the balloon toward the tubular frame, such that the tip-portion of each of the projections is closer than its corresponding base-portion to the tubular frame, and
pressing the flanges against the downstream surface by moving the implant in the upstream direction includes pushing the implant in the upstream direction by pushing the tip-portions against the tubular frame.

In an application, expanding the tubular frame includes inflating the balloon such that (i) the body balloon-portion radially expands the tubular frame by pressing radially outward against the tubular frame, and (ii) the downstream balloon-portion deflects the projections radially outward by pressing radially outward against the projections.

In an application, advancing the distal portion of the delivery tool includes advancing the distal portion of the delivery tool while the projections are disposed within the downstream capsule-portion, and the method further includes, prior to radially expanding the tubular frame, exposing at least the tips of the projections from the downstream capsule-portion.

In an application, exposing at least the tips of the projections from the downstream capsule-portion includes exposing at least the tips of the projections from the downstream capsule-portion prior to pressing the flanges against the downstream surface of the native valve.

There is further provided, in accordance with an application of the present invention, a method for use at a native valve of a heart of a subject, the method including:
advancing, to the heart:
a distal portion of a delivery tool, the delivery tool including:
a shaft that extends to the distal portion of the delivery tool,
a capsule disposed at the distal portion of the delivery tool, and
a balloon, coupled to the shaft, and
an implant disposed within the capsule, and including a tubular frame and an array of shape-memory flanges arranged around an outside of the tubular frame, the tubular frame compressed around the balloon, and the flanges constrained within the capsule;
subsequently, exposing the flanges from the capsule such that the flanges automatically deflect radially outward away from the tubular frame, and such that the array defines an inter-flange distance;
subsequently, by partially inflating the balloon to a partially-inflated state:
(i) partially radially expanding the tubular frame, and
(ii) partially increasing the inter-flange distance;
while the balloon remains in the partially-inflated state, pressing the flanges against a downstream surface of the native valve by moving the implant in an upstream direction; and
subsequently, by further inflating the balloon to a further-inflated state, further radially expanding the tubular frame.

In an application, inflating the balloon to a further-inflated state further includes increasing the inter-flange distance.

In an application:
exposing the flanges includes exposing the flanges while the flanges are positioned upstream of the native valve; and
the method further includes, prior to pressing the flanges against the downstream surface of the native valve, moving the exposed flanges to be downstream of the native valve.

In an application, partially inflating the balloon includes partially inflating the balloon while the flanges are positioned upstream of the native valve.

In an application, inflating the balloon to the further-inflated state includes inflating the balloon to the further-inflated state while continuing to press the flanges against the downstream surface.

In an application, exposing the flanges from the capsule includes moving a downstream capsule-portion of the capsule away from an upstream capsule-portion of the capsule.

In an application, advancing the implant includes advancing the implant while the tubular frame is disposed within the downstream capsule-portion, and the method further includes exposing the tubular frame from the downstream capsule-portion.

In an application, exposing the tubular frame from the downstream capsule-portion includes exposing the tubular frame from the downstream capsule-portion prior to pressing the flanges against the downstream surface of the native valve.

In an application, exposing the tubular frame from the downstream capsule-portion includes exposing the tubular frame entirely from the downstream capsule-portion without causing the tubular frame to expand.

In an application, the implant further includes a shape-memory upstream support portion, constrained within the capsule, and the method further includes, subsequent to pressing the flanges against a downstream surface of the native valve, exposing the upstream support portion from the capsule such that the upstream support portion automatically deflects radially outward.

In an application, exposing the upstream support portion includes exposing the upstream support portion such that the upstream support portion contacts an upstream surface of the native valve.

In an application:
advancing the implant disposed within the capsule, the tubular frame compressed around the balloon, includes advancing the implant disposed within the capsule, the tubular frame compressed around a body balloon-portion of the balloon;
the distal portion of the delivery tool includes one or more projections, each of the projections having a base-portion and a tip-portion;
advancing the distal portion of the delivery tool includes advancing the distal portion of the delivery tool while the one or more projections extend, from the shaft, over at least a downstream balloon-portion of the balloon toward the tubular frame, such that the tip-portion of each of the projections is closer than its corresponding base-portion to the tubular frame; and
pressing the flanges against the downstream surface by moving the implant in the upstream direction includes pushing the implant in the upstream direction by pushing the tip-portions against the tubular frame.

In an application, inflating the balloon includes inflating the balloon such that (i) the body balloon-portion radially expands the tubular frame by pressing radially outward against the tubular frame, and (ii) the downstream balloon-portion deflects the projections radially outward by pressing radially outward against the projections.

In an application, advancing the distal portion of the delivery tool includes advancing the distal portion of the delivery tool while the projections are disposed within the capsule, and the method further includes, prior to partially radially expanding the tubular frame, exposing at least the tip-portions of the projections from the capsule.

There is further provided, in accordance with an application of the present invention, an apparatus for delivery of a prosthetic heart valve to an annulus of a native heart valve, the apparatus including:
a shaft, having a longitudinal shaft-axis;
a capsule, disposed at a distal portion of the shaft;
a balloon, coupled to the shaft, and disposed within the capsule;
one or more projections extending distally from the shaft, such that the projections are arranged around a proximal portion of the balloon; and
a prosthetic valve, including a tubular frame, compressed around the balloon, and disposed within the capsule;
and:
the tubular frame is configured to remain compressed around the balloon upon exposure of the tubular frame from the capsule, such that:
inflation of the balloon to a partially-inflated state partially radially expands the tubular frame, and
inflation of the balloon to a further-inflated state further radially expands the tubular frame;
inflation of the balloon applies a radial force to each of the projections; and
each of the projections is:
sufficiently radially flexible that the radial force deflects the projections radially outward,
sufficiently rigid to axially push the tubular frame while:
the balloon is in the partially-inflated state within the tubular frame, and
the projections are radially outwardly deflected by the balloon in the partially-inflated state.

The present invention will be more fully understood from the following detailed description of applications thereof, taken together with the drawings, in which:

BRIEF DESCRIPTION OF THE DRAWINGS

FIGS. 1A-I are schematic illustrations of an implant, in accordance with some applications of the invention;

DETAILED DESCRIPTION OF EMBODIMENTS

Figure 1A:
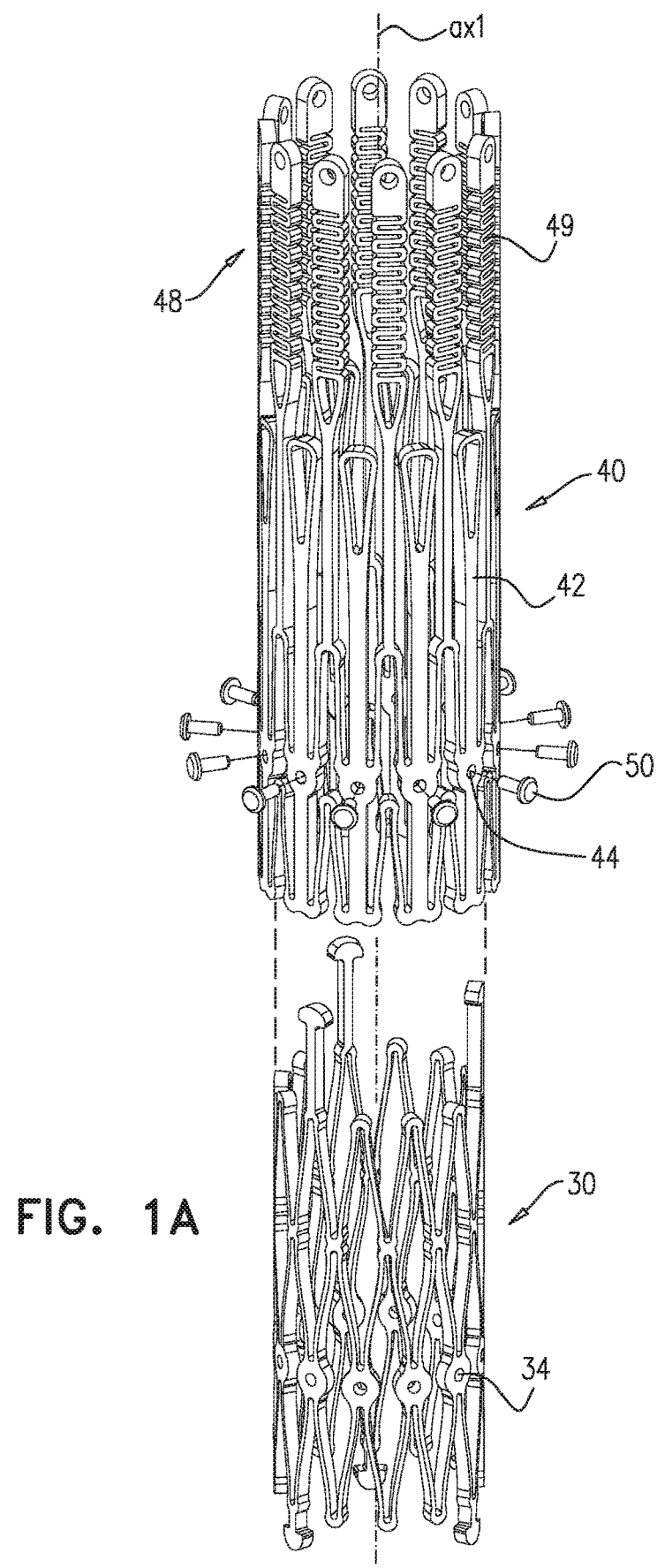
Figure 1B:
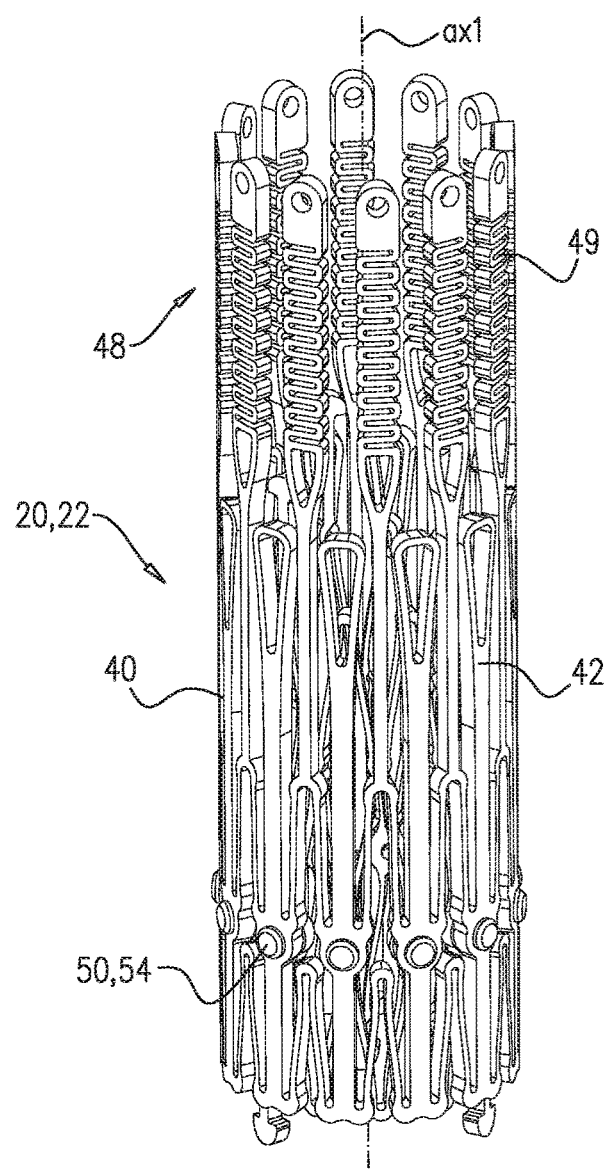
Figure 1C:
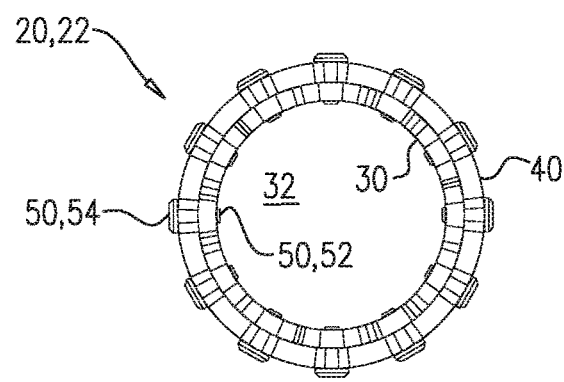
Figure 1D:
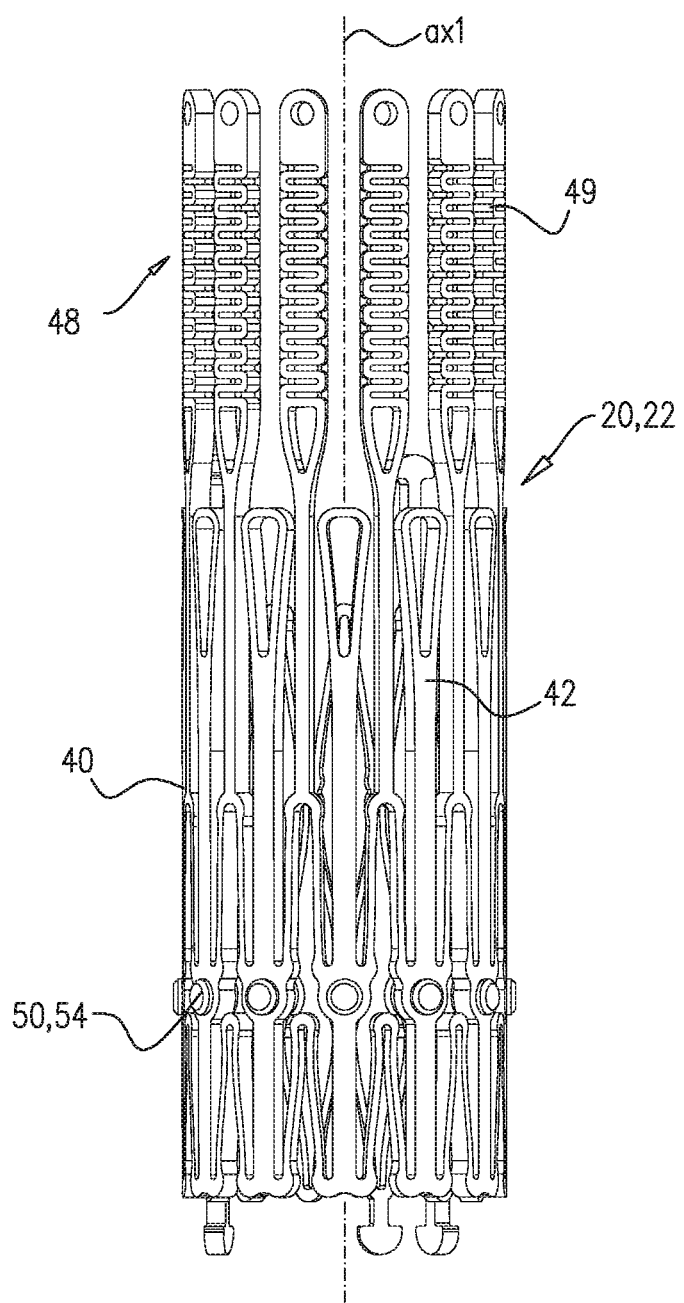
Figure 1E:
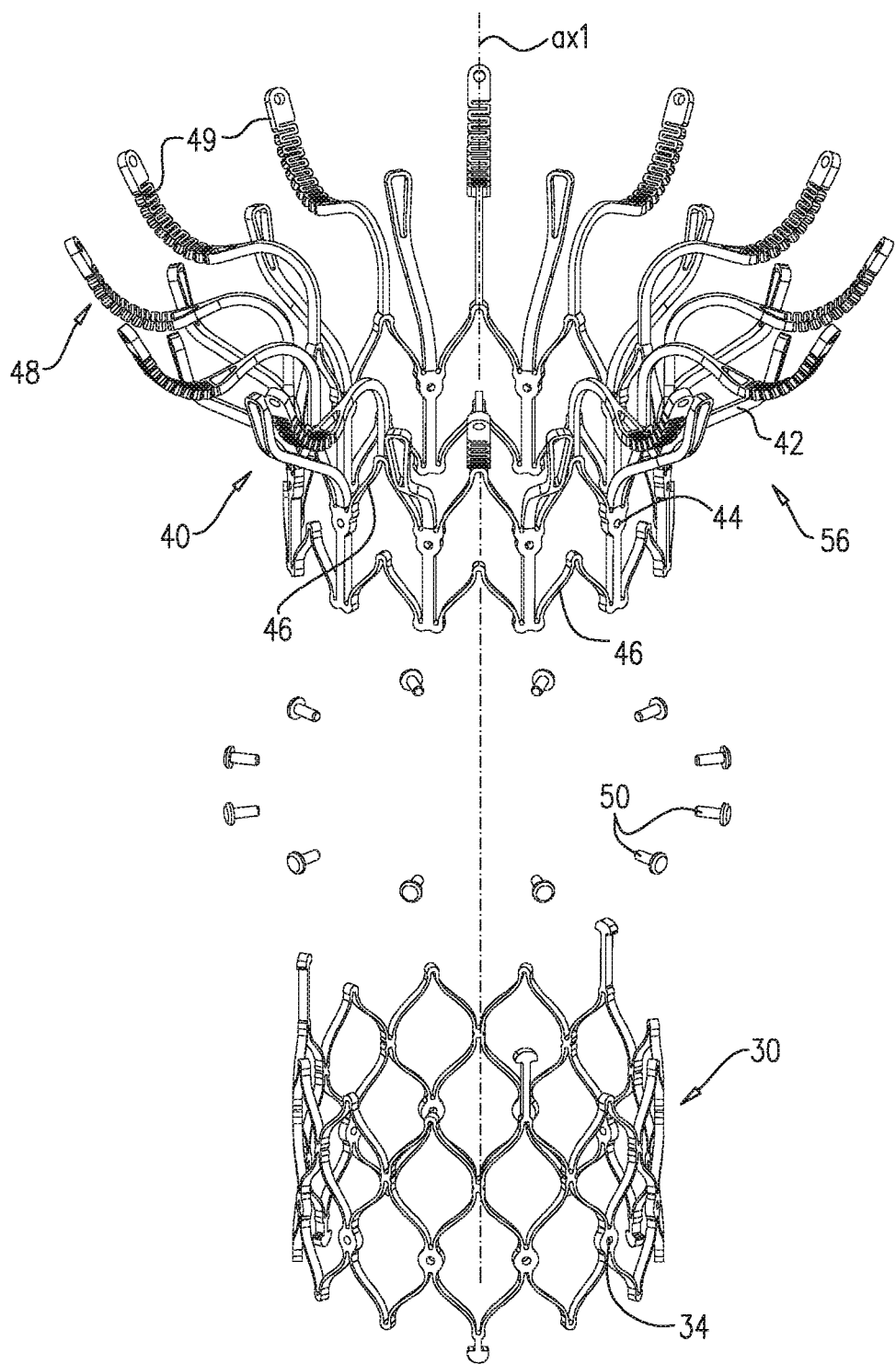
Figure 1F:
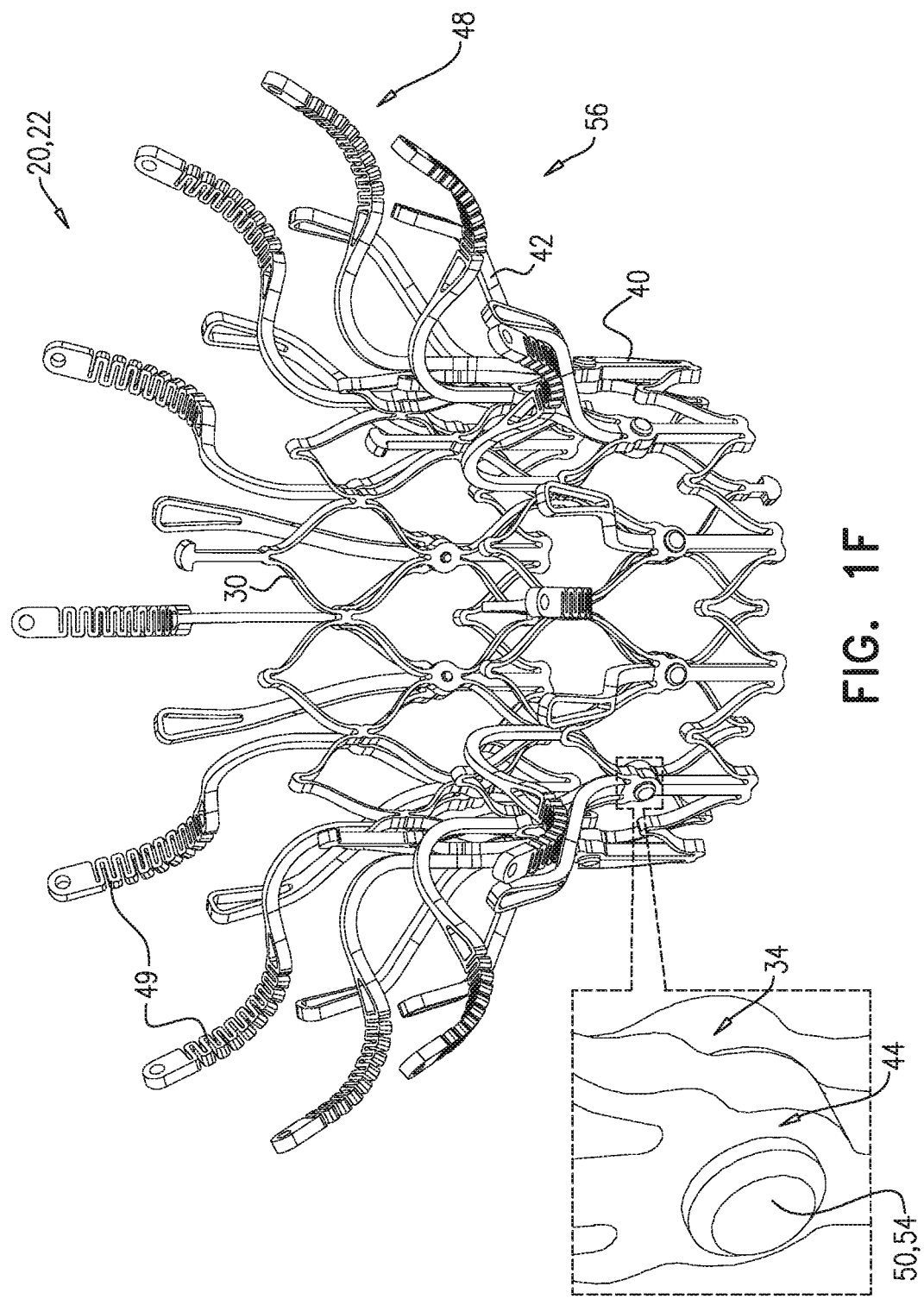

Reference is made to FIGS. 1A-I, which are schematic illustrations of an implant 20, in accordance with some applications of the invention.

Implant 20 comprises a tubular frame 30 that circumscribes a longitudinal axis ax1 to define a lumen 32 along axis ax1. Implant 20 typically further comprises at least one valve member (e.g., prosthetic leaflet 62) (FIG. 1I), disposed within lumen 32, and coupled to frame 30. Therefore implant 20 typically comprises or serves as a prosthetic valve 22.

Implant 20 further comprises an outer frame 40 and one or more pins 50. Outer frame 40 is disposed radially outward from tubular frame 30, comprises one or more flanges 42, and defines one or more eyelets, e.g., outer eyelets 44. Typically, frame 40 comprises a plurality of flanges (e.g., 3-18, such as 6-12, such as 8-12 flanges). Typically, frame 40 defines a plurality of eyelets 44 (e.g., 3-18, such as 6-12, such as 8-12 eyelets). For some applications, the number of eyelets 44 is equal to the number of flanges. Further typically, the number of pins 50 is equal to the number of eyelets 44. In the embodiment shown, there are 12 eyelets, 12 flanges, and 12 pins.

Typically, and as shown, frame 40 circumscribes tubular frame 30. For example, frame 40 may comprise at least one ring 46 that circumscribes tubular frame 30, and to which flanges 42 are coupled. Ring 46 typically defines alternating peaks and troughs, e.g., being zigzag or wavy in shape.

Typically, tubular frame 30 also defines one or more eyelets, e.g., inner eyelets 34. Typically, frame 30 defines a plurality of eyelets 34 (e.g., 3-18, such as 6-12, such as 8-12 eyelets). Typically, the number of eyelets 34 is equal to the number of eyelets 44.

Outer frame 40 is composed of a shape-memory alloy such as nickel titanium (e.g., Nitinol), whereas tubular frame 30 and pins 50 are composed of a material that is not the shape-memory alloy. That is, frame 30 and pins 50 are both composed of the same material, and that material is not the shape-memory alloy of which frame 40 is composed. Typically, the material of which frame 30 and pins 50 are composed is not a shape-memory material of any kind. For example, frame 30 and pins 50 may be composed of steel (e.g., stainless steel, such as 316LVM) or a cobalt chrome alloy (e.g., MP35N or L605). It is to be noted that throughout this patent application (including the specification and the claims) the term "composed of" x means that x is the primary substance from which an element is made, such that x confers its properties on the element that is made of x.

Pins 50 couple outer frame 40 to tubular frame 30. Each pin 50 defines a shaft 52 and a head 54. Shaft 52 is passed radially-inwardly through an eyelet 44 to tubular frame 30, such that head 54 is disposed against outer frame 40, radially outward from the eyelet 44. Shaft 52 is welded to tubular frame 30. Typically, shaft 52 is also passed radially inwardly through a respective eyelet 34, and is welded to tubular frame 30 at eyelet 34. Because pin 50 and frame 30 are both composed of the same material, they may be welded together. In contrast, frame 40 is composed of a different material than pin 50, and coupling therebetween is provided by head 54, which is larger than eyelet 44.

Typically, each flange 42 has a root-portion 41 and a tip 43, and extends away from the tubular frame from the root-portion to the tip. Each outer eyelet 44 is typically defined at (e.g., by) the root-portion 41 of a respective flange 42, e.g., such that the head 54 of the respective pin 50 is disposed against the root-portion of the flange, radially outward from the eyelet.

There is therefore provided, in accordance with some applications of the invention, apparatus for use in a heart of a subject, the apparatus comprising:
  a tubular frame that circumscribes a longitudinal axis to define a lumen along the longitudinal axis;
  a valve member, disposed within the lumen and coupled to the tubular frame;
  an outer frame:
    disposed radially outward from the tubular frame, comprising a flange, and
    defining an eyelet; and
  a pin:
    defining a shaft and a head, and
    coupling the outer frame to the tubular frame,
  wherein:
    the outer frame is composed of a shape-memory alloy,
    the tubular frame and the pin are composed of a material that is not the shape-memory alloy,
    the head is disposed against the outer frame, radially outward from the eyelet,
    the shaft extends from the head through the eyelet to the tubular frame, and
    the shaft is welded to the tubular frame.

Typically, frame 40 is cut from a tube of the shape-memory alloy. Typically, frame 30 is cut (e.g., laser cut) from a tube of the other material. In order to facilitate implant 20 serving as a prosthetic heart valve, lumen 32 is typically lined with a lining 60 (e.g., comprising a fabric), and a plurality of prosthetic leaflets 62 (e.g., comprising bovine pericardium) are secured within the lumen, e.g., by suturing the leaflets to lining 36 and/or to frame 30. For the sake of clarity, lining 60, leaflets 62, and other fabric elements are omitted in FIGS. 1A-H.

There is therefore further provided, in accordance with some applications of the invention, a method for constructing implant 20 (e.g., a prosthetic heart valve), the method comprising:
  from a tube of a shape-memory alloy, cutting an outer frame that comprises a flange and defines an eyelet;
  from a tube of a material that is not the shape-memory alloy, cutting a tubular frame that circumscribes a longitudinally axis to define a lumen along the longitudinal axis;
  positioning the outer frame against the tubular frame, radially-outward from the tubular frame;
  passing a shaft of a pin through the eyelet such that (i) the shaft of the eyelet extends to the tubular frame, and (ii) a head of the pin is disposed against the outer frame radially outward from the eyelet, the pin being composed of the material;
  welding the shaft to the tubular frame;
  lining at least part of the lumen with a lining; and
  securing a plurality of prosthetic leaflets within the lumen.

Typically, and as shown, implant 20 further comprises an upstream support portion 48, e.g., comprising a plurality of radial arms 49 optionally covered in an annular sheet. Further typically, it is outer frame 40 that defines upstream support portion 48, and therefore the upstream support portion is also composed of the shape-memory alloy. Flanges 42 extend radially outward from tubular frame 30, and toward upstream support portion 48. As discussed in more detail hereinbelow, flanges 42 are configured to engage a downstream surface of a native heart valve, and upstream support portion is configured (e.g., shaped and/or dimensioned) to be placed against an upstream surface of the native heart valve.

Figure 1G:
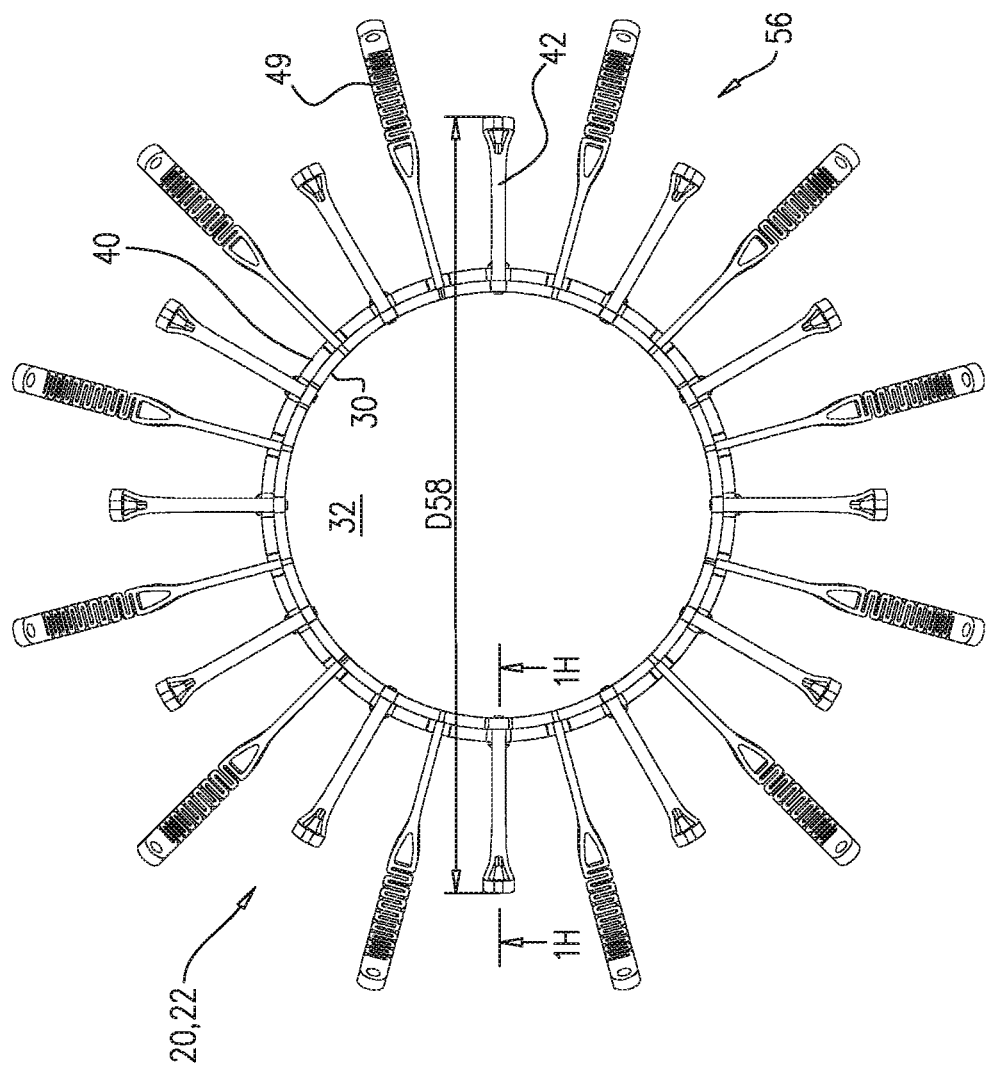
Figure 1H:
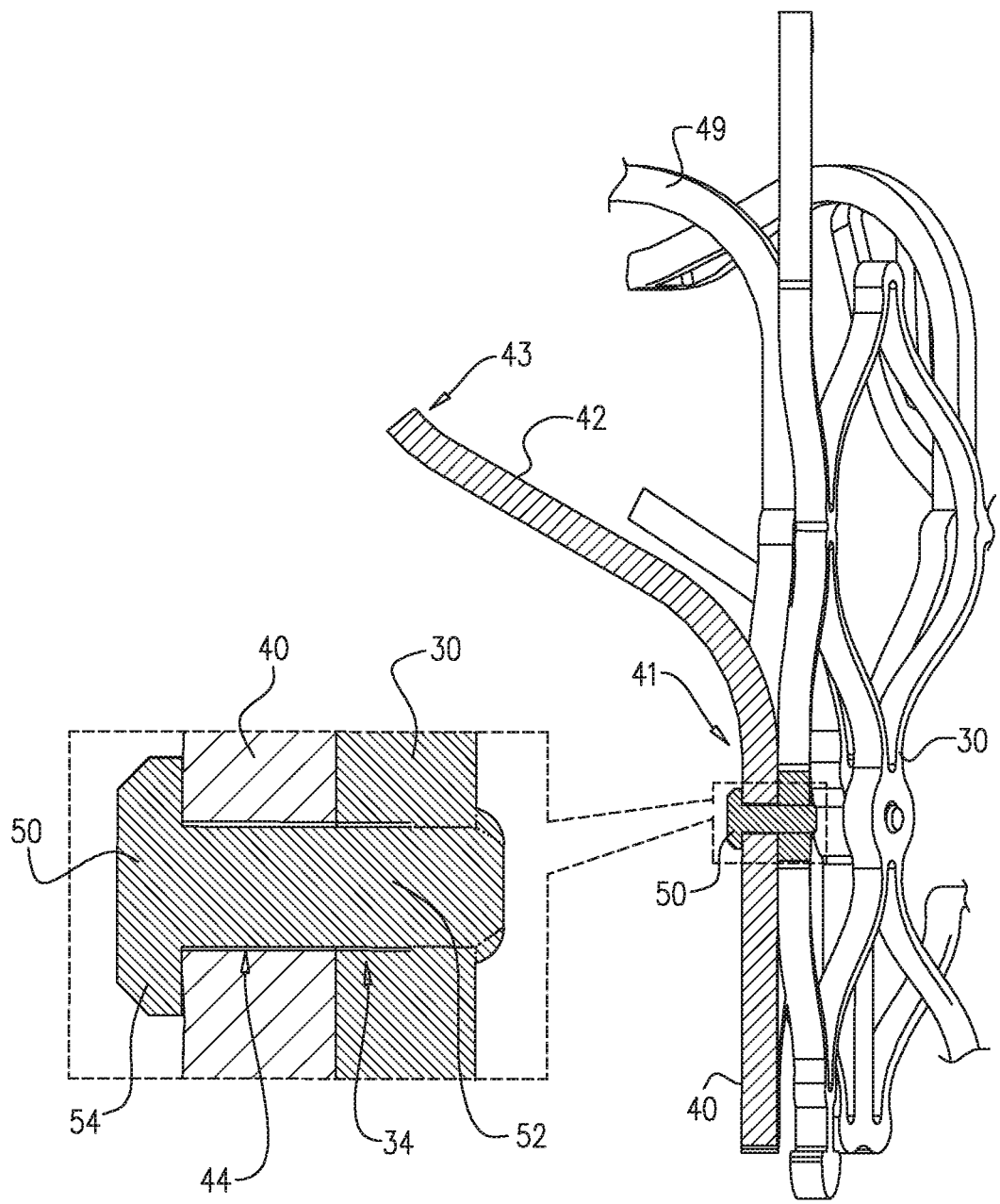
Figure 11:
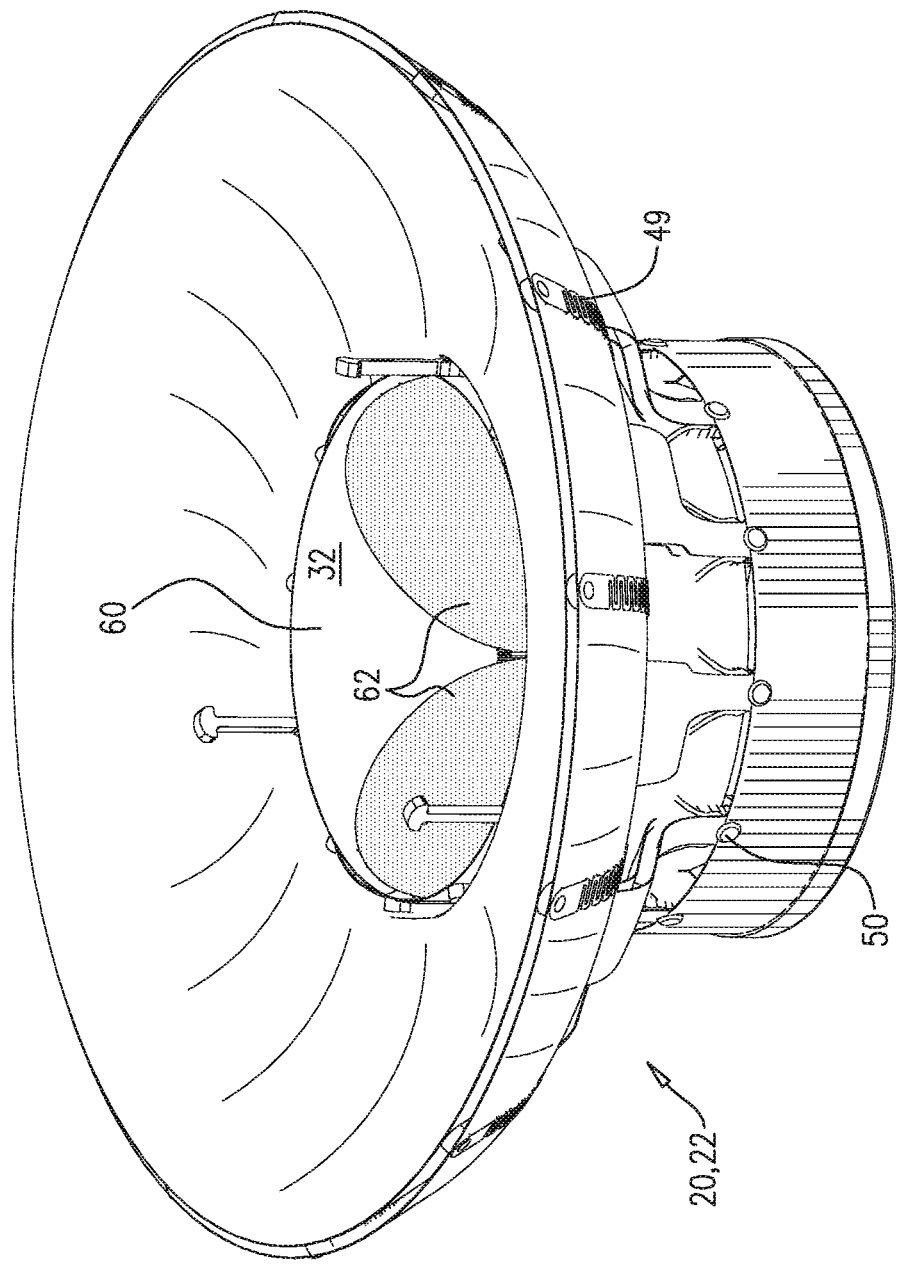

Frame 40 is shaped and memory-set such that, when unconstrained, upstream support portion 48 and flanges 42 extend radially outward from tubular frame 30. Typically, when unconstrained, flanges 42 are arranged in an array 56 around the outside of tubular frame 30, the array defining an inter-flange distance D58. Although inter-flange distance D58 is shown in FIG. 1G as a distance between opposing flanges 42, in some embodiments the inter-flange distance may refer to an alternative measurement (e.g., a distance between adjacent flanges 42). As discussed hereinbelow (e.g., with reference to FIGS. 3A-H), implant 20 is delivered while radially compressed (i.e., "crimped"), with upstream support portion 48 and flanges 42 constrained within a capsule. Because frame 40 is composed of the shape-memory alloy, upon being exposed from the capsule upstream support portion 48 and flanges 42 automatically deflect radially outward. In contrast, although tubular frame 30 is also radially compressed during delivery, it retains its radially-compressed state upon being exposed from the capsule, and is subsequently plastically-expanded, e.g., using a balloon. Typically, in the absence of frame 30, frame 40 (e.g., ring 46) would automatically radially expand upon being exposed from the capsule. However, because frame 40 is coupled to frame 30 (e.g., via pins 50), frame 30 inhibits frame 40 (e.g., ring 46 thereof) from radially expanding until frame 30 is plastically expanded. That is, despite the elasticity of frame 40, frame 30 is typically sufficiently rigid to inhibit frame 40 from automatically radially expanding upon exposure from the capsule. Similarly, the elasticity of frame 40 is typically insufficient to pull frame 30 into its radially expanded state (i.e., the state in which implant 20 functions as a prosthetic valve).

Reference is made to FIGS. 2A-D, which are schematic illustration of a tool 100, in accordance with some applications of the invention. For some applications, tool 100 is used to implant implant 20 at the native valve (e.g., as described with reference to FIGS. 3A-H).

Tool 100 comprises a shaft 106, a capsule 110, and a balloon 120, which is typically a non-compliant balloon. Shaft 106 has a central longitudinal shaft-axis ax2, which typically is the same as, or is collinear with, a central longitudinal axis of tool 100. Capsule 110 is disposed at a distal portion 104 of the tool (e.g., at a distal end of shaft 106), and comprises an upstream capsule-portion 112 and a downstream capsule-portion 114, and is openable by moving the upstream capsule-portion and the downstream capsule-portion apart. Balloon 120 is coupled to shaft 106, and is disposed within capsule 110 (e.g., downstream capsule-portion 114 thereof). As shown, tool 100 typically comprises a controller and/or handle 108 at a proximal portion 102 of the tool.

Figure 2A:
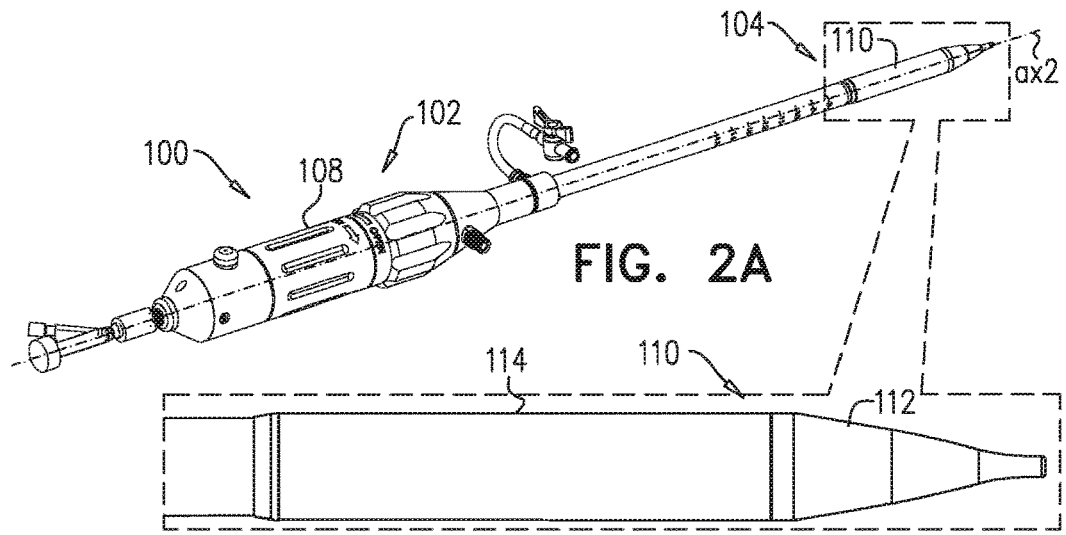
FIGS. 2A-D are schematic illustration of a tool, in accordance with some applications of the invention.
Figure 2B:
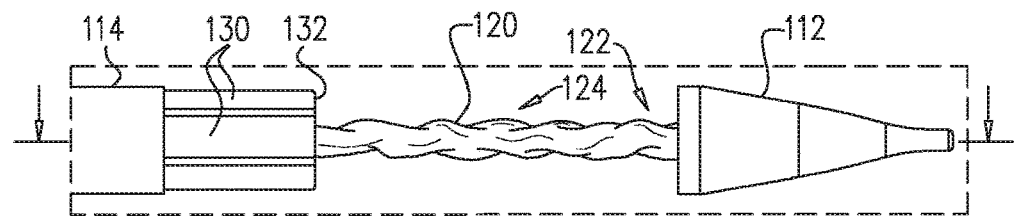
Figure 2C:
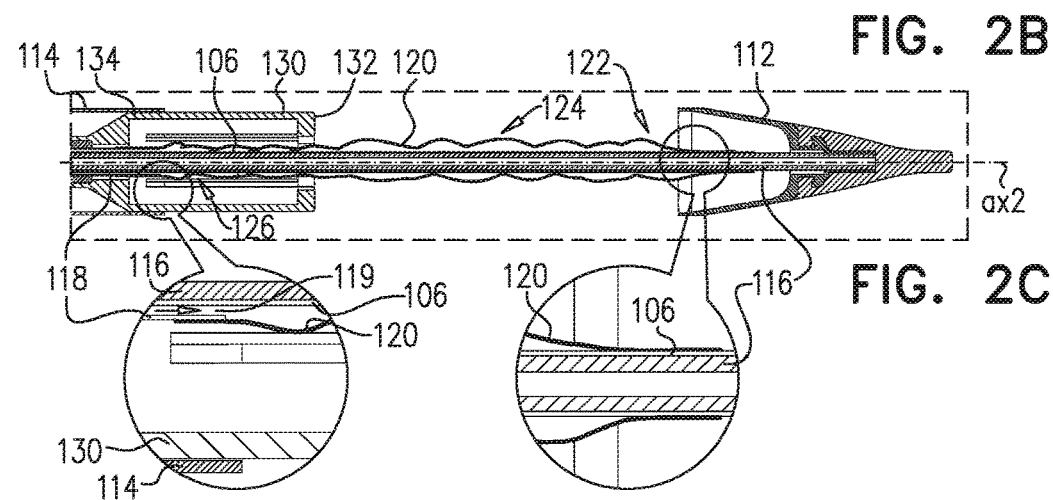
Figure 2D:
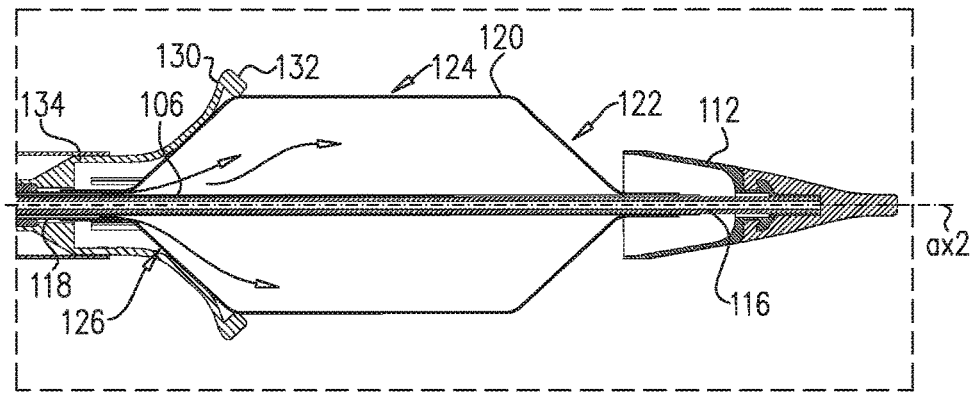

FIG. 2A shows tool 100 in a closed state, with capsule-portions 112 and 114 close to each other (e.g., in contact with each other). FIG. 2B shows tool 100 in an open state, after capsule 110 has been opened by retracting capsule-portion 114 away from capsule-portion 112. FIG. 2C shows a longitudinal cross-section of FIG. 2B. FIG. 2D shows the same longitudinal cross-section as FIG. 2C, but with balloon 120 inflated. For clarity, implant 20 is not shown in FIGS. 2A-D.

As described hereinabove, outer frame 40 of implant 20 is composed of a shape-memory alloy. Flanges 42 are shape-set to protrude radially outward. Upstream support portion 48 is (e.g., arms 49 thereof are) also shape-set to protrude radially outward. As described in more detail with reference to FIGS. 3A-H, flanges 42 and upstream support portion 48 are disposed within, and constrained radially inward by, capsule 110 during delivery. For example, flanges 42 may be constrained by downstream capsule-portion 114 (e.g., constrained within the downstream capsule-portion), and upstream support portion 48 may be constrained by upstream capsule-portion 112 (e.g., constrained within the upstream capsule-portion). For delivery of implant 20, tubular frame 30 is compressed around balloon 120, which will eventually be used to radially expand the tubular frame. Typically, during delivery tubular frame 30 is disposed within downstream capsule-portion 114. Therefore, in preparation for implantation of implant 20, an operator typically compresses (e.g., "crimps") tubular frame 30 around balloon 120, radially compresses and at least partly encapsulates flanges 42 within downstream capsule-portion 114, and radially compresses and at least partly encapsulates upstream support portion 48 (e.g., arms 49 thereof) within upstream capsule-portion 112.

In the delivery state of the apparatus, balloon 120 is typically disposed within capsule 110, flanges 42 are typically constrained within downstream capsule-portion 114, and upstream support portion 48 is typically constrained within upstream capsule-portion 112. For some applications, the term "within" means "entirely within," i.e., with no part of the balloon, flange, or upstream support portion disposed outside of the capsule or capsule-portion. For some applications, the term "within" means "at least partly within," i.e., part of the balloon, flange, or upstream support portion may be disposed outside of the capsule or capsule-portion.

There is therefore provided, in accordance with some applications of the invention, apparatus comprising:
a delivery tool, comprising:
    a shaft, having a shaft-axis;
    a capsule, disposed at a distal portion of the tool, and comprising an upstream capsule-portion and a downstream capsule-portion, the capsule being openable by moving the upstream capsule-portion and the downstream capsule-portion apart; and
    a balloon, coupled to the shaft, and disposed within the capsule; and
a prosthetic valve, comprising:
    a tubular frame, compressed around the balloon, and disposed within the capsule;
    one or more shape-memory flanges, constrained within the downstream capsule-portion; and
    a shape-memory upstream support portion, constrained within the upstream capsule-portion,
wherein:
    the flanges are configured to automatically deflect radially outward upon exposure of the tubular frame from the downstream capsule-portion,
    the upstream support portion is configured to automatically deflect radially outward upon exposure from the upstream capsule-portion,
    the tubular frame is configured to remain compressed around the balloon upon exposure from the capsule, and
    while the tubular frame is exposed from the capsule, inflation of the balloon plastically expands the tubular frame radially.

Balloon 120 has an upstream (e.g., distal) balloon-portion 122, a downstream (e.g., proximal) balloon-portion 126, and a body (e.g., intermediary) balloon-portion 124 therebetween. Body balloon-portion 124 typically comprises the widest part of balloon 120. Typically, body balloon-portion 124 is disposed within lumen 32 of tubular frame 30. That is, for delivery, tubular frame 30 is typically compressed around body balloon-portion 25. As shown in FIG. 2D, when inflated, body balloon-portion 124 is typically cylindrical, and balloon-portions 122 and 126 typically taper away from the body balloon-portion and from tubular frame 30. For example, balloon-portions 126 and 126 may be conical or hemispherical.

Typically, balloon 120 is fixed to shaft 106, e.g., by at least one end of the balloon being attached to the shaft. For example, and as shown, balloon-portion 124 may be attached to shaft 106. Tool 100 defines an inflation channel 119 from proximal portion 102 to distal portion 104. For some applications, and as shown, tool 100 comprises a pipe 118 through which shaft 106 extends, and channel 119 is defined between the pipe and the channel. For such applications, balloon-portion 126 of balloon 120 is typically attached to pipe 118, placing balloon 120 in fluid communication with channel 119 such that the balloon is inflatable via the channel.

Typically, pipe 118 is fixed with respect to shaft 106. However, both upstream capsule-portion 112 and downstream capsule-portion 114 are typically axially movable with respect to shaft 106, such as by one of the capsule-portions being attached to a rod 116 that is slidable through the shaft, and the other one of the capsule-portions being attached to a tube (not shown) that is slidable over the shaft. For example, and as shown, capsule-portion 112 may be attached to rod 116, and capsule-portion 114 may be attached to the tube. Upstream capsule-portion 112 is retractable from over upstream support portion 48 by being moved away from balloon 120 (i.e., in an upstream direction), and downstream capsule-portion 114 is retractable from over flanges 42 by being moved away from the balloon (i.e., in a downstream direction).

Typically, tool 100 comprises one or more (typically a plurality of) elongate projections 130. Projections 130 are configured to apply an axial pushing force against implant 20 (e.g., tubular frame 30 thereof), in order to maintain the positioning of the implant during deployment. For example, and as described in more detail with reference to FIGS. 3A-H, after flanges 42 are exposed and allowed to expand, the flanges may be pushed and held against a downstream surface of the native valve (e.g., leaflets thereof), typically until balloon 120 is at least partly inflated. Typically, each of projections 130 is sufficiently stiff (e.g., axially stiff) that, when pushed against tubular frame 30, it is capable of applying an axial pushing force of at least 0.5 N, e.g., at least 5 N, such as at least 10 N—e.g., without the projection buckling. For example, each projection 130 may be capable of applying a pushing force of 0.5-50 N, e.g., 0.5-20 N (e.g., 0.5-15 N) or 5-50 N (e.g., 5-20 N, e.g., 5-15 N, such 5-10 N or 10-15 N). Typically, projections 130 are collectively capable of applying an axial pushing force of at least 3 N, (e.g., at least 6 N, e.g., at least 20 N, e.g., at least 40 N, such as at least 60 N) to tubular frame 30—e.g., without the projection buckling. For example, projections 130 may be collectively capable of applying a pushing force of 3-100 N e.g., 3-30 N (e.g., 6-30 N) or 40-100 N (e.g., 40-80 N or 60-100 N). For clarity, these axial pushing force values are as measured with the projection or projections aligned parallel to axis ax1.

During delivery (i.e., in a delivery state of tool 100 and implant 20), projections 130 are typically disposed within downstream capsule-portion 114. Each projection 130 has a tip-portion (e.g., a free end) 132, and a base-portion 134. Base-portion 134 is disposed deeper into the downstream capsule-portion than is tip-portion 132. Projections 130 are arranged circumferentially around shaft-axis ax2, such that tip-portions 132 are arranged circumferentially around balloon-portion 126 of balloon 120, with the tip-portion of each projection being closer than its corresponding base-portion 134 to tubular frame 30. Typically, in the delivery state, tip-portions 132 abut tubular frame 30 (e.g., a proximal and/or downstream surface thereof). However, projections 130 (e.g., tip-portions 132 thereof) are typically not attached to tubular frame 30. Therefore, after expansion of tubular frame 30 and deflation of balloon 120 (e.g., as described with reference to FIGS. 3A-H), projections 130 can be withdrawn without actively disengaging them from the tubular frame.

Tool 100 is typically configured to facilitate continued application, by projections 130, of the axial pushing force against tubular frame 30 while the tubular frame is being expanded, despite the presence of tapered balloon-portion 126. This feature, and its advantages, are discussed in more detail hereinbelow with reference to FIGS. 4A-B, 5A-B, and 6A-B. Once tubular frame 30 and tip-portions 132 are exposed from downstream capsule-portion 114, inflation of balloon 120 both (i) radially expands the tubular frame (e.g., by body balloon-portion 124 pressing radially outward against the tubular frame), and (ii) deflects each of projections 130 radially outward (e.g., by balloon-portion 124 pressing radially outward against the projection).

The apparatus may be configured such that projections 130 deflect simultaneously and/or at the same rate that the tubular frame expands, allowing contact between the projections and the tubular frame to be maintained. For example, tubular frame 30 may define a frame-circumference, the tip-portions may collectively define a projection-circumference, and while the tubular frame and the tip-portions are exposed from the downstream capsule-portion, inflation of balloon 120 may increase the projection-circumference at the same rate as it increases the frame-circumference.

Each projection 130 is therefore sufficiently flexible (e.g., radially flexible) that it is deflected by a radial force F1 applied by the radial expansion of balloon-portion 126. Nonetheless, as described hereinabove, each projection 130 is also typically capable of applying an axial pushing force F2 of at least 0.5 N to tubular frame 30 (e.g., to overcome an axial resistance force F3, of frame 30 against the projections, in the opposite direction of force F2). Forces F1, F2, and F3 are indicated in FIG. 4B.

For some applications of the invention, this configuration is facilitated by each projection 130 being non-isometrically flexible. For example, each projection 130 may have a radial stiffness in its radial plane 136, and a lateral stiffness in its lateral plane 138, the lateral stiffness being greater than (e.g., more than twice as great as) the radial stiffness. For clarity, radial plane 136 is a plane on which the projection and axis ax2 lie, and in which the projection deflects, and lateral plane 138 is typically transverse to the radial plane. Lateral plane 138 may also be tangential to the projection-circumference collectively defined by the tip-portions of projections 130.

For some applications of the invention, outward radial force F1 is of a greater magnitude than axial resistance force F3. It is hypothesized by the inventors that, for at least some such applications of the invention, F1 being greater than F3 facilitates deflection of projections 130 simultaneously with the projections axially pushing tubular frame 30.

For some applications, and as shown, tip-portions 132 are shaped to define a face that has a greater transverse cross-sectional area than parts of projection 130 that are closer to base-portion 134. These faces are visible in FIGS. 2C-D. The difference in transverse cross-sectional area may be understood by comparing the element labeled "130" in the lower cross-section of FIG. 3B, with the element labeled "130, 132" in the upper cross-section of FIG. 3B. It is hypothesized by the inventors that, due to their greater transverse cross-sectional area, these faces facilitate application of the axial pushing force to tubular frame 30.

Reference is now made to FIGS. 3A-H, which are schematic illustrations showing tool 100 being used to deliver implant 20 to a native valve 10 of a heart 4 of a subject, in accordance with some applications of the invention. Although FIGS. 3A-H show a percutaneous transapical approach, it is to be noted that the scope of the present invention includes other percutaneous approaches, such as transatrial, or transluminal (e.g., transfemoral), mutatis mutandis. It is to be noted that the scope of the present invention includes modifications to tool 100 that facilitate these approaches. Although FIGS. 3A-H show valve 10 as being a mitral valve, it is to be noted that the scope of the present invention includes the native valve being a tricuspid valve, an aortic valve, or a pulmonary valve, mutatis mutandis.

Figure 3A:
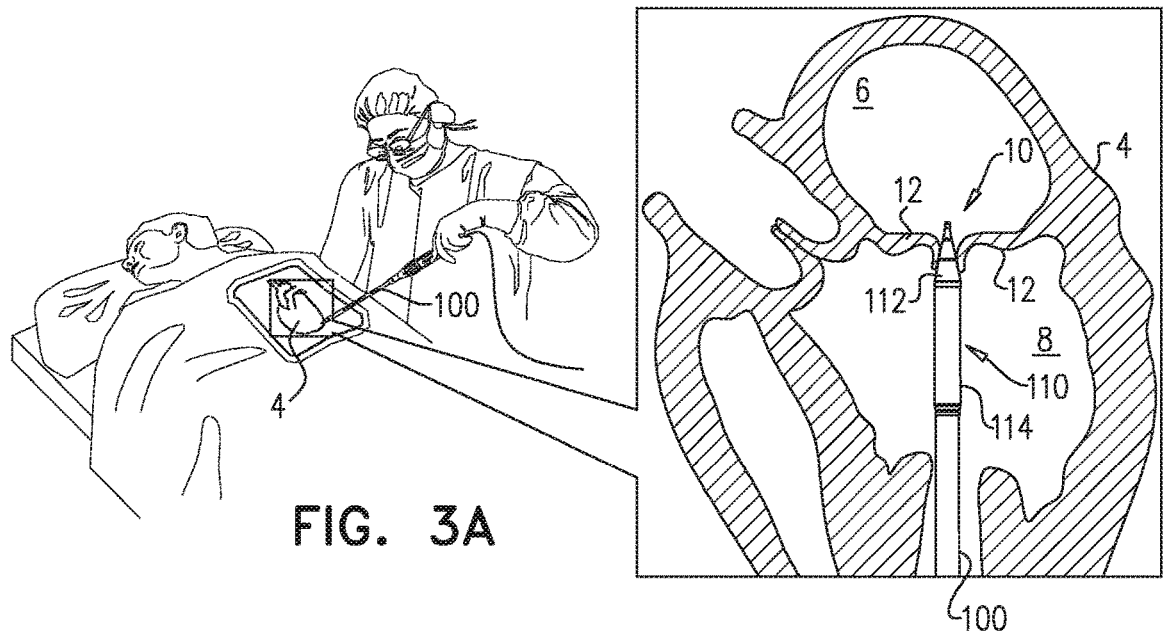
FIGS. 3A-H are schematic illustrations showing the tool being used to deliver the implant to a native valve of a heart of a subject, in accordance with some applications of the invention.
Figure 3B:
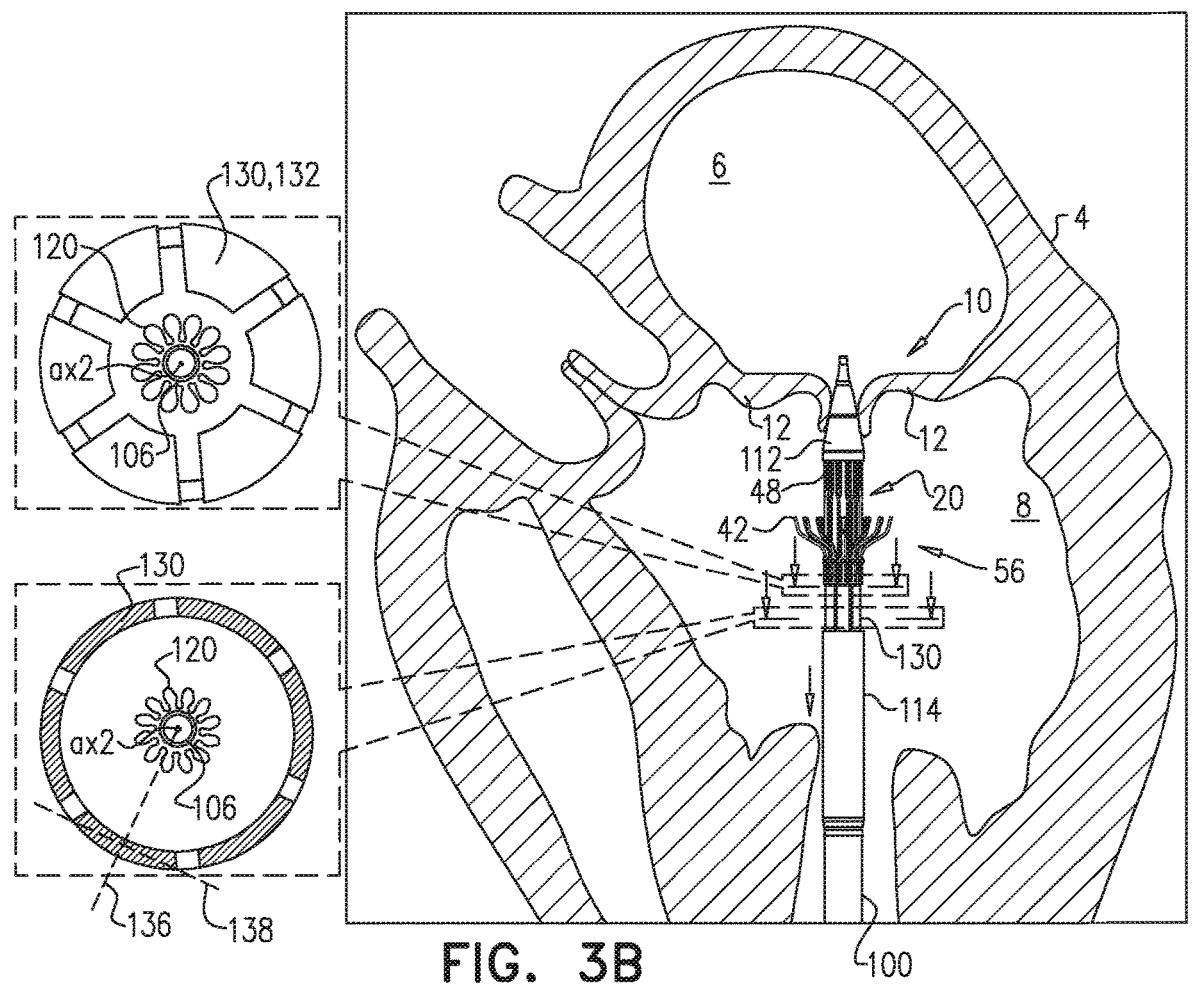
Figure 3C:
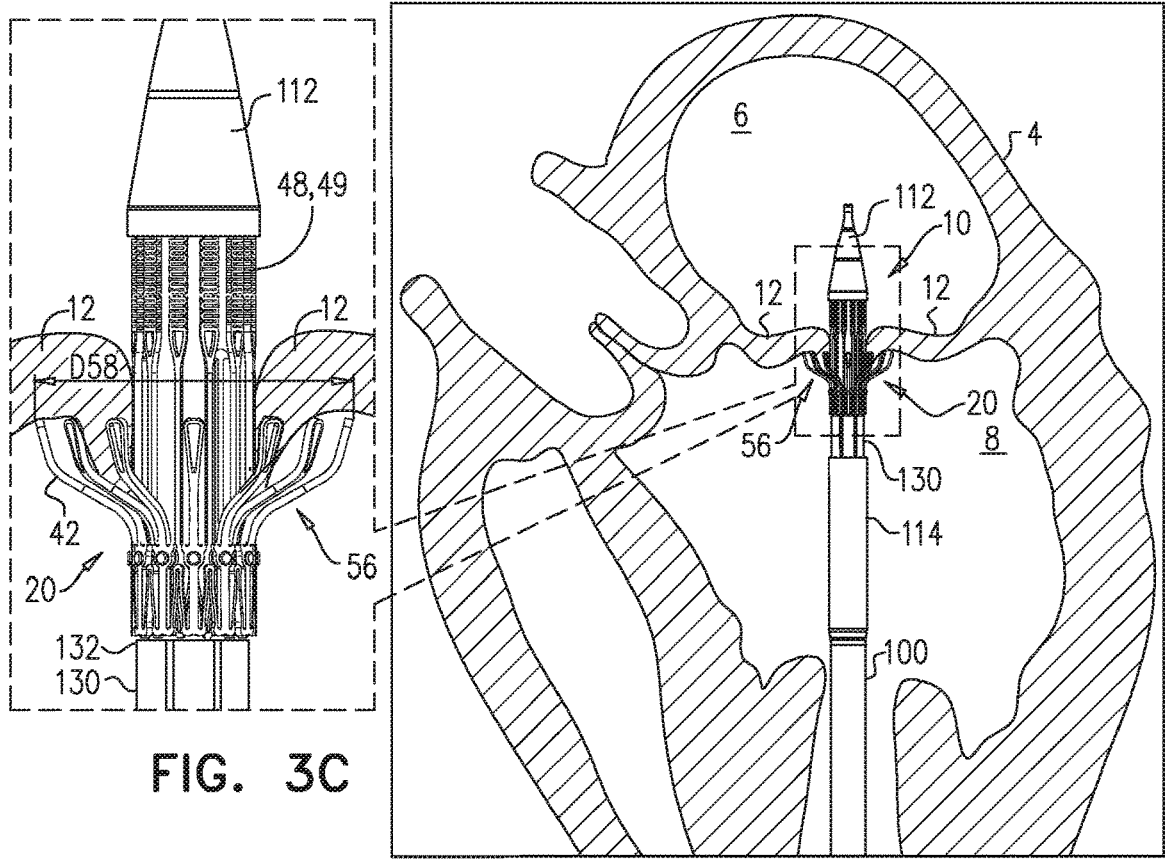

While tool 100 and implant 20 are in the delivery state (e.g., with capsule 110 closed, and implant 20 compressed therewithin), tool 100 is transapically advanced into left ventricle 8 (FIG. 3A). For some applications, and as shown, tool 100 is positioned (e.g., facilitated by fluoroscopy) such that capsule-portion 112 is disposed between native leaflets 12 of valve 10. Capsule-portion 114 is then retracted, in a downstream direction, away from capsule-portion 112, exposing (i) at least flanges 42 of implant 20, and (ii) at least tip-portions 132 of projections 130 (FIG. 3B). Flanges 42 automatically deflect radially outward upon becoming exposed. Typically, and as shown in the inset of FIG. 3C, flanges 42 are arranged in array 56 around the outside of tubular frame 30, the array defining inter-flange distance D58. Typically, this step also exposes tubular frame 30 from capsule-portion 114. As described hereinabove, tubular frame 30 typically does not expand upon becoming exposed from capsule-portion 114.

FIG. 3B includes two cross-sections. The upper cross-section is at the level of contact between projections 130 and implant 20, and therefore shows tip-portions 132 of the projections arranged circumferentially around uninflated balloon 120, through which shaft 106 extends. The lower cross-section is further downstream/proximal, closer to base-portions 134 of projections 130. The lower cross-section also shows, for one projection 130, a radial plane 136 and a lateral plane 138. As described hereinabove, radial plane 136 is a plane on which projection 130 and axis ax1 lie, and in which the projection deflects, and lateral plane 138 is typically transverse to the radial plane.

Flanges 42 are subsequently pressed against a downstream surface of native valve 10 by moving implant 20 in an upstream direction (FIG. 3C). This is performed by applying, via projections 130, the axial pushing force described hereinabove. Typically, flanges 42 are pressed against leaflets 12 of the native valve.

As shown in FIG. 3C, for applications in which prosthetic valve 22 comprises upstream support portion 48, this movement of implant 20 includes placing the upstream support portion, constrained by capsule-portion 112, upstream of native valve 10 (i.e., into left atrium 6). For such applications, projections 130 typically facilitate retention of upstream support portion 48 within capsule-portion 112 by obstructing implant 20 from moving axially away from the capsule-portion.

Figure 3D:
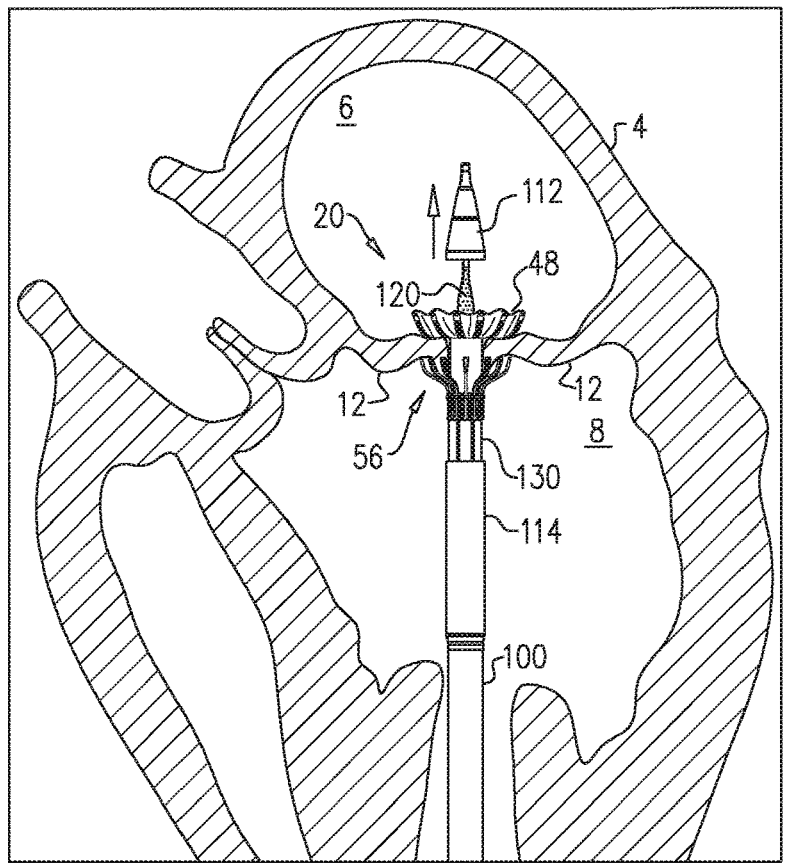

Subsequently, upstream support portion 48 is exposed from capsule-portion 112 and automatically deflects radially outward, e.g., contacting an upstream surface of native valve 10 (FIG. 3D).

Figure 3E:
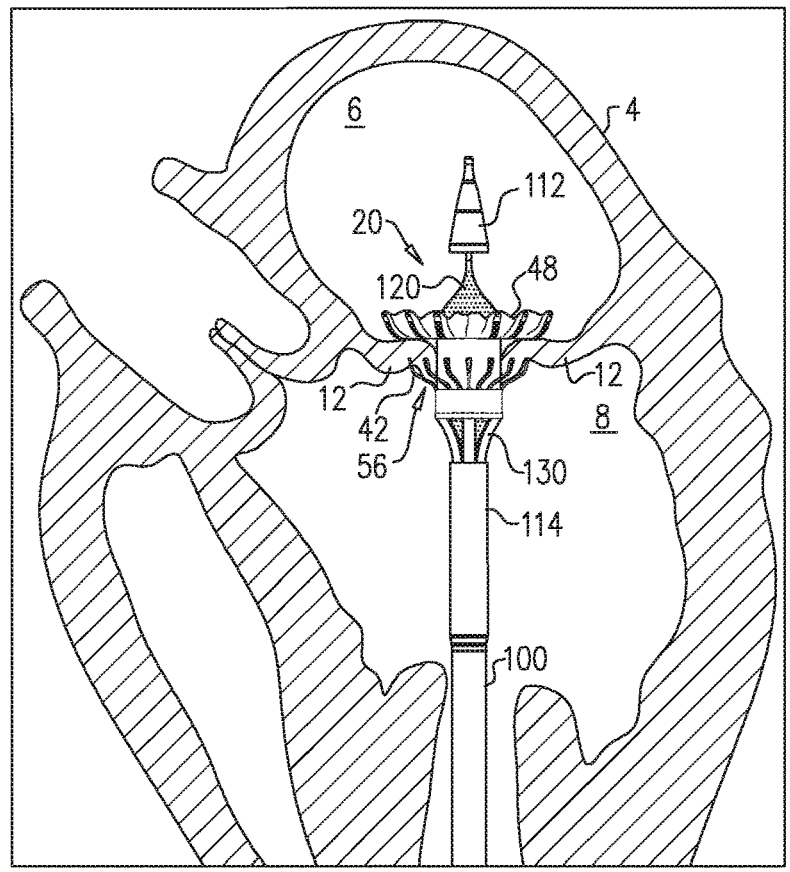
Figure 3F:
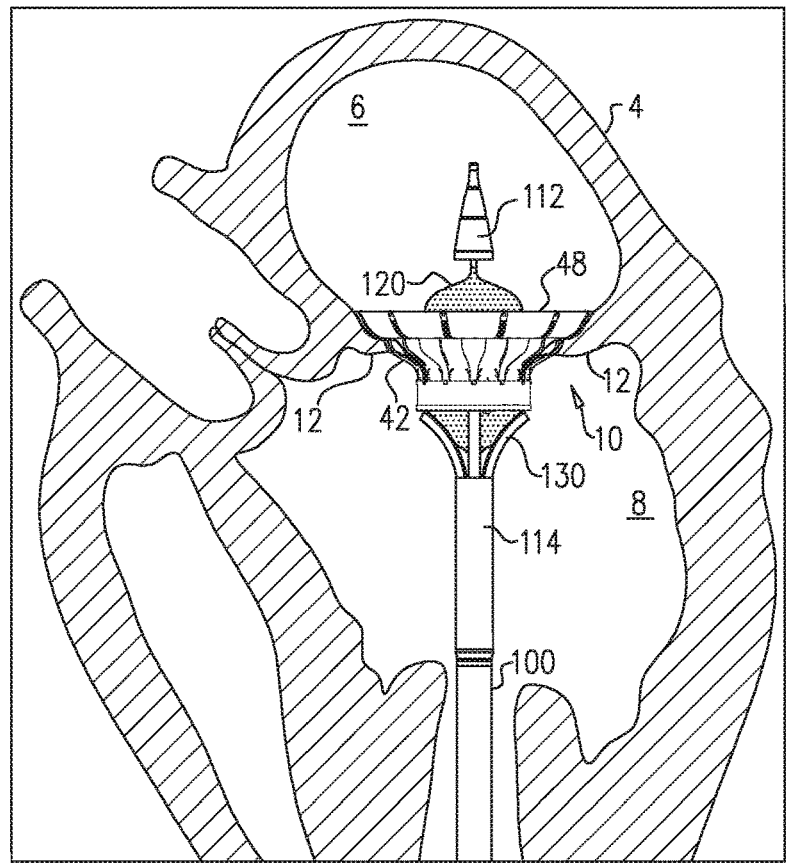

While flanges 42 remain in contact with the downstream surface of the native valve, and typically while upstream support portion 48 remains in contact with the upstream surface of the native valve, tubular frame 30 is plastically expanded radially by inflating balloon 120 (FIGS. 3E-F). For some applications, this is performed while continuing to press flanges 42 against the downstream surface using projections 130. As described hereinabove, projections 130 are configured to deflect radially outwardly as tubular frame 30 expands upon inflation of balloon 120, and therefore (i) do not inhibit radial expansion of the balloon, and (ii) facilitate optional continued application of the axial pushing force during inflation of the balloon.

Figure 3G:
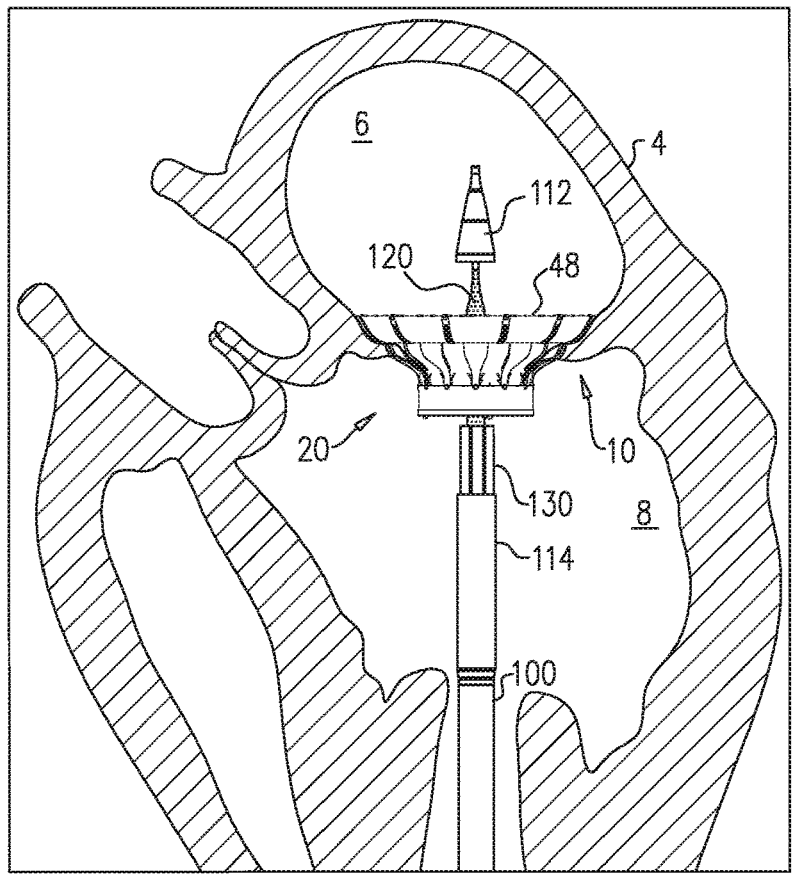
Figure 3H:
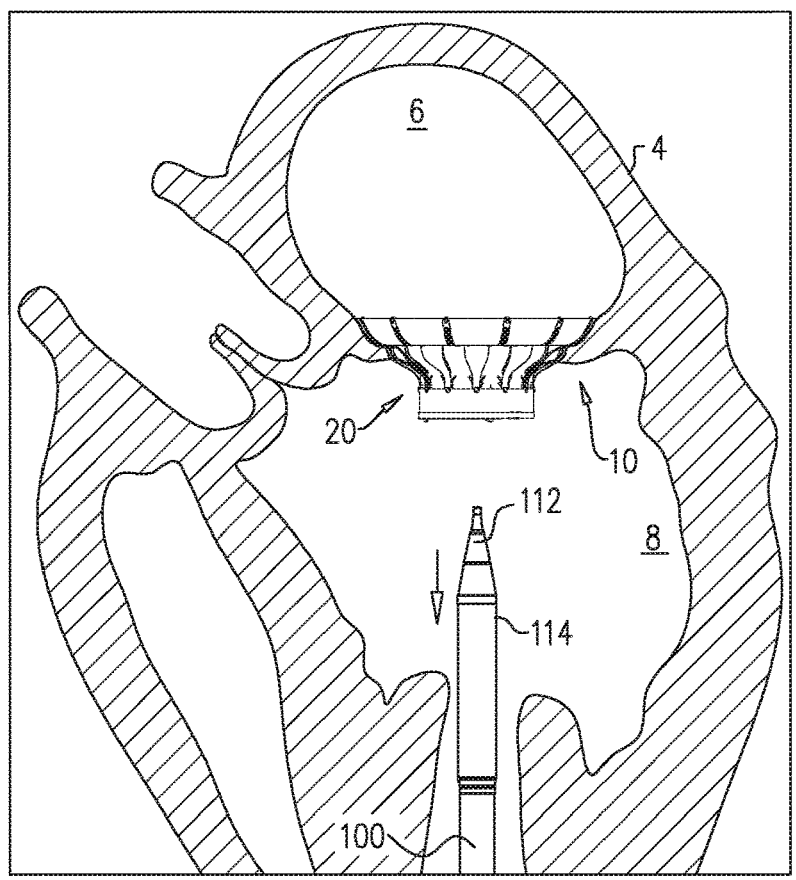

After implant 20 has been implanted and expanded, balloon 120 is deflated, and tool 100 is removed from the subject, typically after closing capsule 110 (FIGS. 3G-H).

Reference is now made to FIGS. 4A-B, 5A-B, and 6A-B, which are schematic illustrations of implant-delivery tools 100, 200, and 300, in accordance with some applications of the invention. In FIGS. 4A-B, 5A-B, and 6A-B, a generic expandable implant 180 is shown being implanted using the respective tool. For some applications, implant 180 may represent tubular frame 30 of implant 20.

Figure 4A:
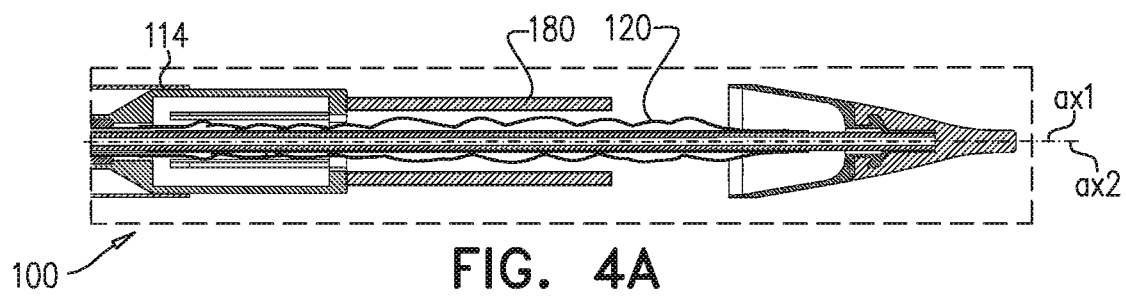
FIGS. 4A-B, 5A-B, and 6A-B, are schematic illustrations of implant-delivery tools, in accordance with some applications of the invention.
Figure 4B:
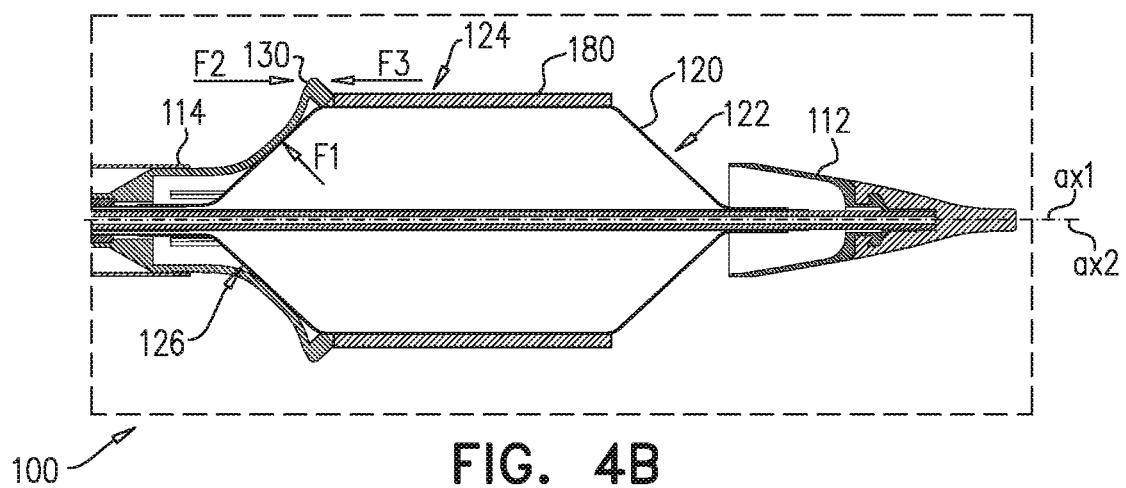
Figure 5A:
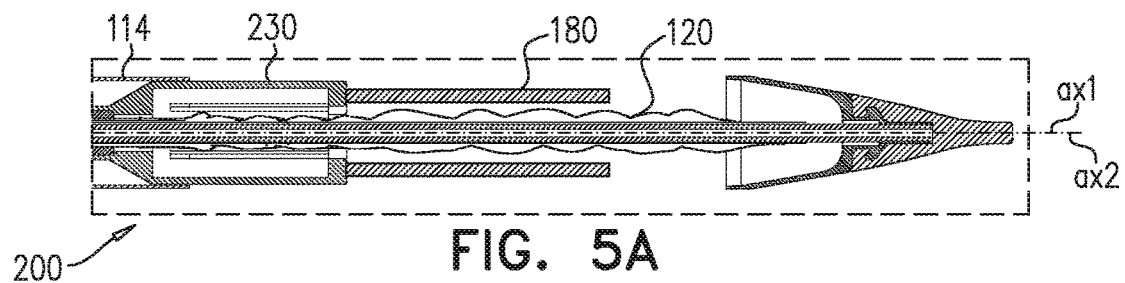
Figure 5B:
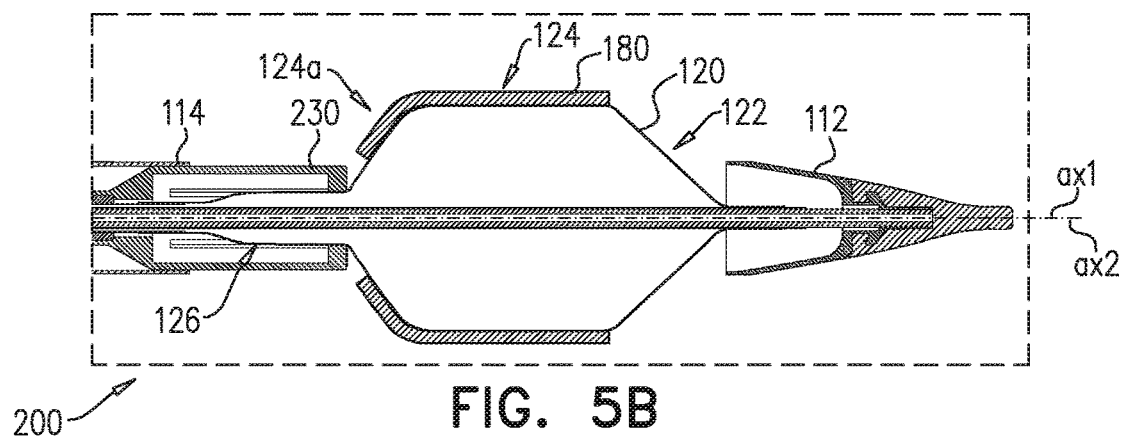
Figure 6A:
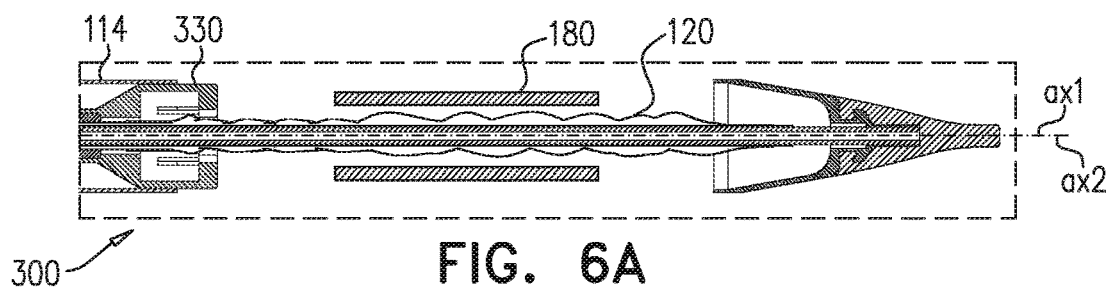
Figure 6B:
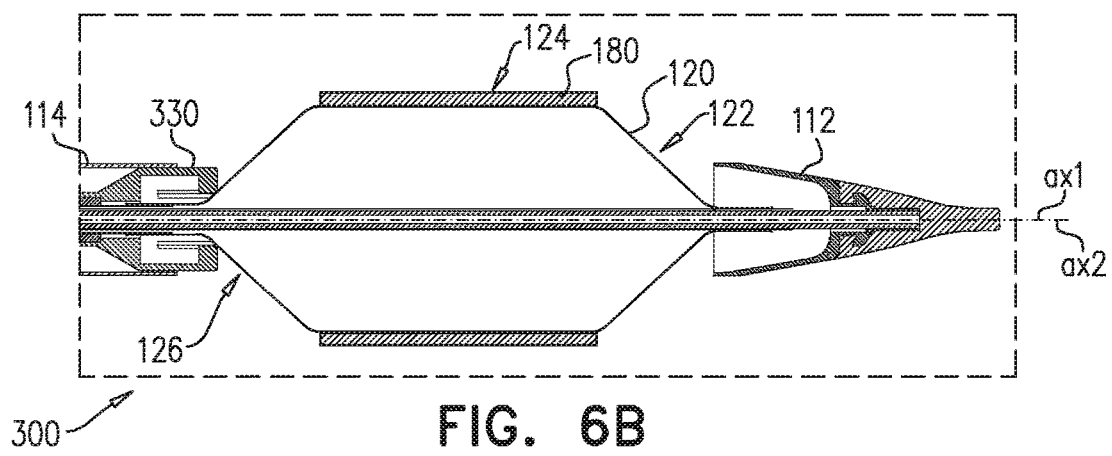

FIGS. 4A-B show tool 100 being used with implant 180, e.g., as described hereinabove for implant 20. The states of tool 100 in FIGS. 4A-B generally correspond to the state of tool 100 in FIGS. 2C-D, respectively, except that in FIGS. 4A-B implant 180 is shown. That is, (i) FIG. 4A shows implant 180 disposed around body balloon-portion 124 of balloon 120, with downstream capsule-portion 114 having been withdrawn, and balloon 120 not yet inflated, and (ii) FIG. 4B shows balloon 120 having been inflated. FIGS. 5A-B and 6A-B show the same states (e.g., the same steps of deployment) for tools 200 and 300.

Tool 200 is identical to tool 100, except that it comprises projections 230 instead of projections 130. Projections 230 are identical to projections 130, except that they are more rigid. Projections 330 are identical to projections 130 except that they are shorter, and therefore do not extend over balloon-portion 126 to implant 180. (Projections 330 may be flexible like projections 130 or rigid like projections 230.) As described hereinabove, tool 100 is typically configured to facilitate continued application, by projections 130, of the axial pushing force against tubular frame 30 while the tubular frame is being expanded, despite the presence of tapered balloon-portion 126. The advantage conferred by projections 130 may be illustrated by the following comparison of the results of using tool 200 and/or tool 300, to the result of using tool 100.

As described hereinabove, body balloon-portion 124 is typically cylindrical, and balloon-portions 122 and 126 typically taper away from the body balloon-portion. A balloon of this shape advantageously can withstand a greater inflation pressure than can a similar balloon that is entirely cylindrical (i.e., with flat ends). However, in order to expand implant 180 evenly, the implant is disposed around body balloon-portion 124, which is cylindrical when inflated.

Before inflation of balloon 120, there is no difference between using tool 100 and using tool 200. When balloon 120 of tool 100 is inflated, projections 130 are pushed radially outward by the balloon, allowing downstream balloon-portion 126 (over which the projections are disposed) to assume its conical shape, and body balloon-portion 124 to assume its cylindrical shape, thereby evenly expanding implant 180. When inflated, balloon 120 typically fills the lumen of implant 180 uniformly.

In contrast, when balloon 120 of tool 200 is inflated, projections 130 are not pushed radially outward by the balloon, and instead constrain balloon-portion 126 (over which the projections are disposed) from expanding. Therefore, a downstream region 124a of body balloon-portion 124 is inhibited from fully inflating and joining the rest of the body balloon-portion in becoming cylindrical. Therefore, the part of implant 180 that is disposed around region 124a is not expanded to the same degree as other parts of the implant. That is, implant 180 is not expanded evenly.

Projections 330 of tool 300 do not extend over balloon-portion 126 to implant 180, and therefore do not constrain balloon-portion 126 from expanding. However, because they do not reach implant 180, they are unable to serve the function of applying the axial force to the implant in order to correctly position the implant during implantation. Furthermore, in some instances, implant 180 may slip with respect to balloon 120 and become positioned over conical balloon-portion 126 or 122, which, as described hereinabove, may result in uneven expansion of the implant.

Therefore, the particular quality of projections 130 to be both (i) sufficiently rigid to apply the axial force to an implant, and (ii) sufficiently radially flexible to be pushed radially outward by balloon 120, provides tool 100 with the ability to both (i) control the position of an implant, and (ii) to evenly expand the implant.

Reference is made to FIGS. 7A-H and 8A-C, which are schematic illustrations of additional embodiments of implant-delivery tool 100 being used to deliver implant 20 to a native valve 10 of a heart 4 of a subject, in accordance with some applications of the invention. In such embodiments, balloon 120 is configured to be expandable to at least (i) a partially-inflated state and (ii) a further-inflated state. For example, proximal portion 102 of tool 100 (e.g., controller/handle 108) may be configured to inflate balloon 120 to a distinct partially-inflated state, and may be further configured to inflate balloon 120 to a further-inflated state. It is hypothesized by the inventors that regulated inflation of balloon 120, such that the balloon may be maintained in the partially-inflated state, may facilitate some applications of tool 100, as described hereinbelow. Since such embodiments share similarities with those described above in reference to FIGS. 3A-H, the following description will focus upon aspects differentiating between them and the embodiments described hereinabove in reference to FIGS. 3A-H.

Figure 7A:
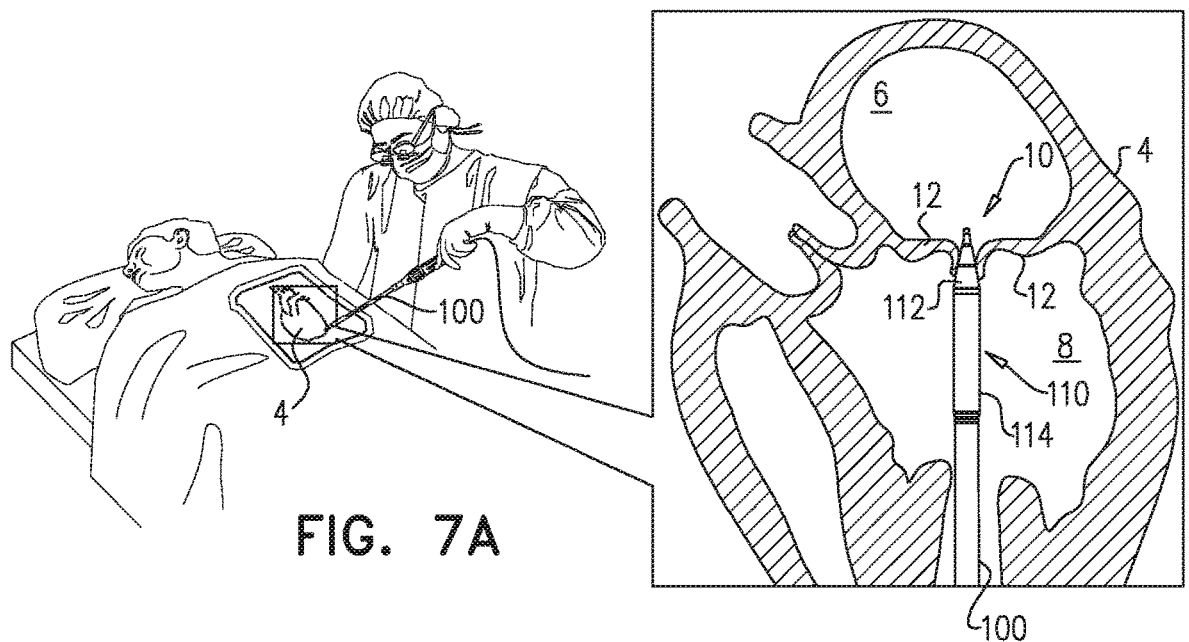
FIGS. 7A-H and 8A-C are schematic illustrations of additional embodiments of implant-delivery tools, in accordance with some applications of the invention.
Figure 7B:
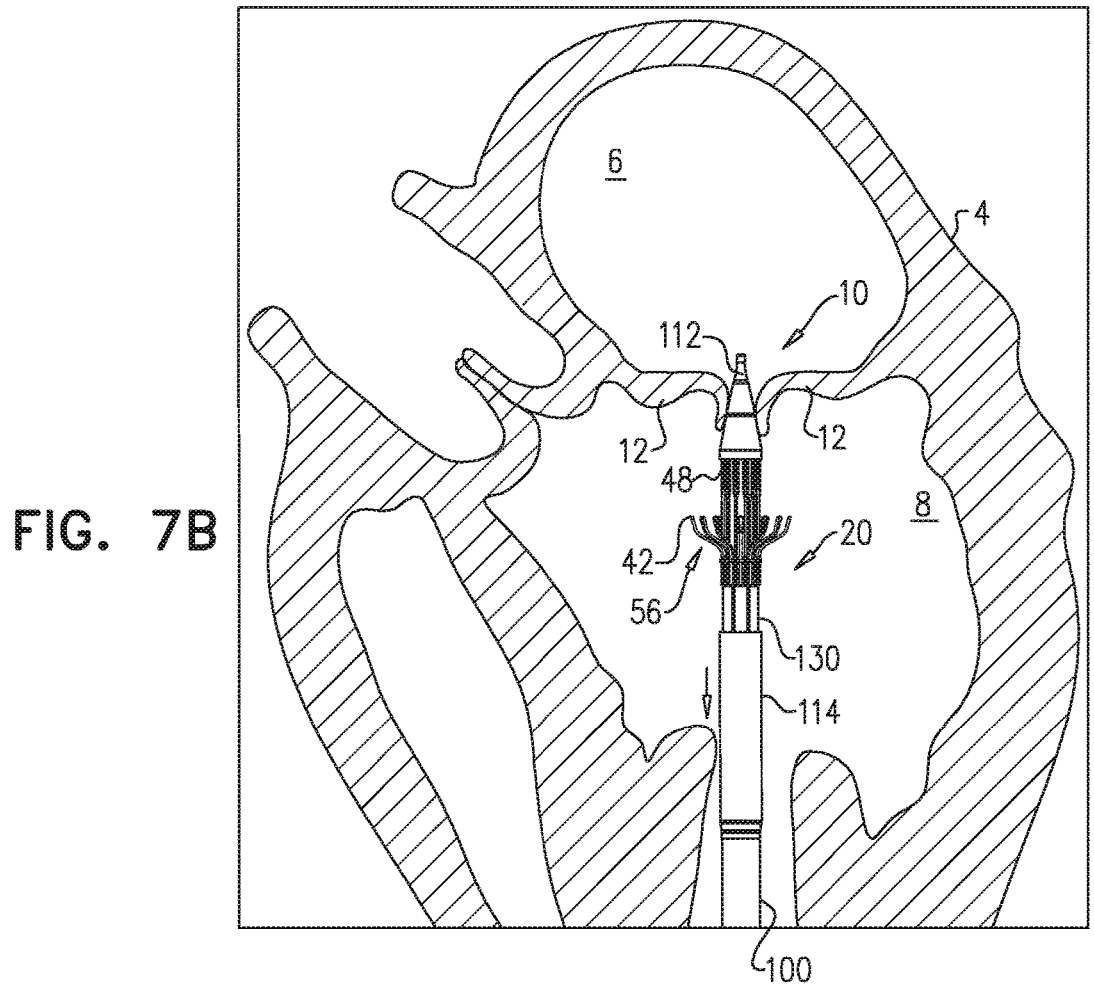

Although FIGS. 7A-H and 8A-C show a transapical approach to a native mitral valve, these embodiments of the invention may also be modified as necessary to accommodate alternate approaches to a mitral or other native heart valve, mutatis mutandis. FIG. 7A shows tool advanced while implant 20 is disposed within capsule 110, from which the implant is later exposed. Typically, and as shown in FIG. 7B, flanges 42 deflect automatically radially outward upon exposure from capsule 110, whereas tubular frame 30 typically does not expand upon being partially or entirely exposed from the capsule. Further typically, and as shown, capsule 110 comprises upstream capsule-portion 112 and downstream capsule-portion 114, and flanges 42 are exposed from the capsule by moving the downstream capsule-portion away from the upstream capsule-portion. Further typically, flanges 42 are (i) exposed from the downstream capsule-portion and (ii) arranged in array 56 around the outside of tubular frame 30, before the flanges are pressed against the downstream surface of the native valve 10.

Figure 7C:
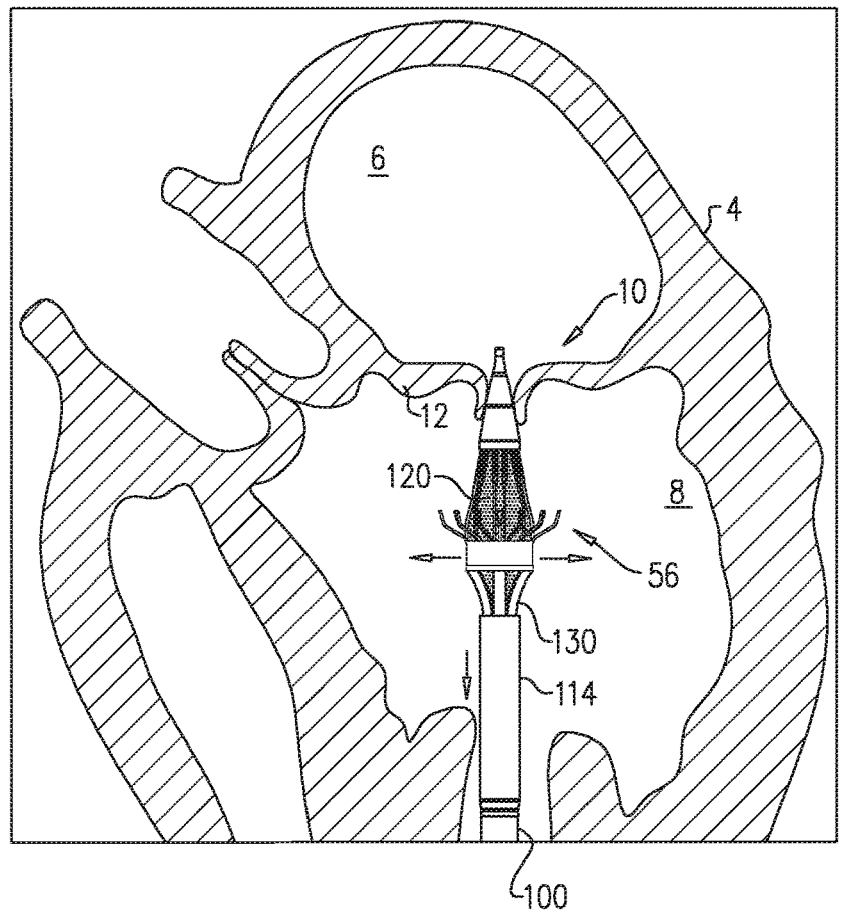
Figure 7D:
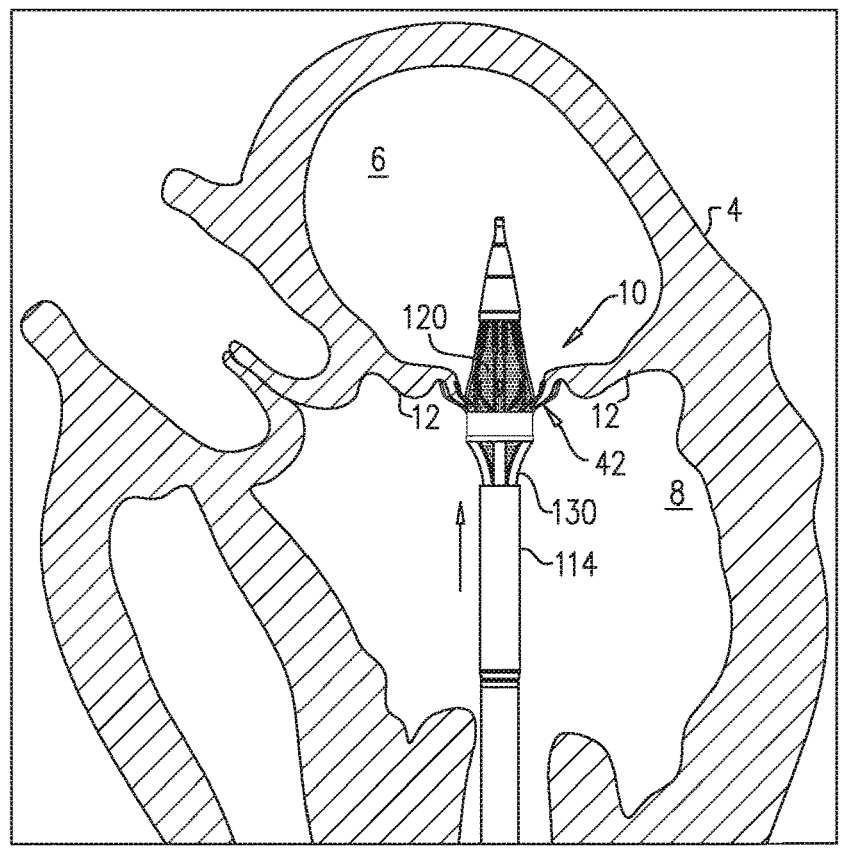

For some applications, it may be desirable to at least partially expand tubular frame and/or array 56 of flanges 42, prior to the flanges contacting the downstream surface of native valve 10. FIG. 7C shows inflation of balloon 120 to the partially-inflated state, before flanges 42 contact the surface of the native valve 10. Inflation of balloon 120 to the partially-inflated state enacts, inter alia, (i) partial radial expansion of tubular frame 30, and/or (ii) partial increasing of inter-flange distance D58 defined by array 56. FIG. 7D shows pressing of flanges 42 against a downstream surface of the native valve 10 by moving implant 20 in an upstream direction, while inter-flange distance D58 remains partially increased. Typically, and as shown, this is achieved by moving the implant in the upstream direction while balloon 120 remains in the partially-inflated state. In this way, partial inflation of balloon 120 may enable flanges to reach further laterally while contacting the downstream surface of native valve 10. It is hypothesized by the inventors that increasing inter-flange distance D58 defined by array 56, before flanges 42 press against the downstream surface, may facilitate capture of the tissue of native valve 10 (e.g., native leaflets 12)—e.g., increasing an amount of the tissue eventually captured between flanges 42 and upstream support portion 48.

Figure 7E:
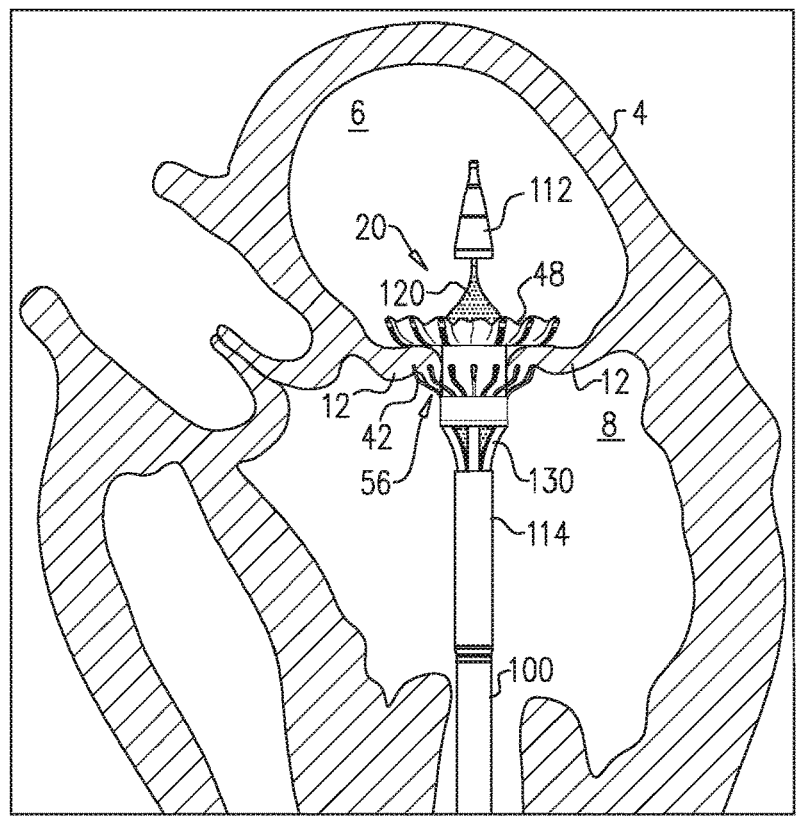

Subsequently, upstream support portion 48 is exposed from capsule 110 while flanges 42 remain in contact with the downstream surface (e.g., continue to press against the downstream surface), while inter-flange distance D58 remains partially increased, and typically while balloon 120 remains partially inflated (FIG. 7E). This may be analogous to the step shown in FIG. 3D, but with inter-flange distance D58 partially increased, and balloon 120 typically being partially inflated.

Figure 7F:
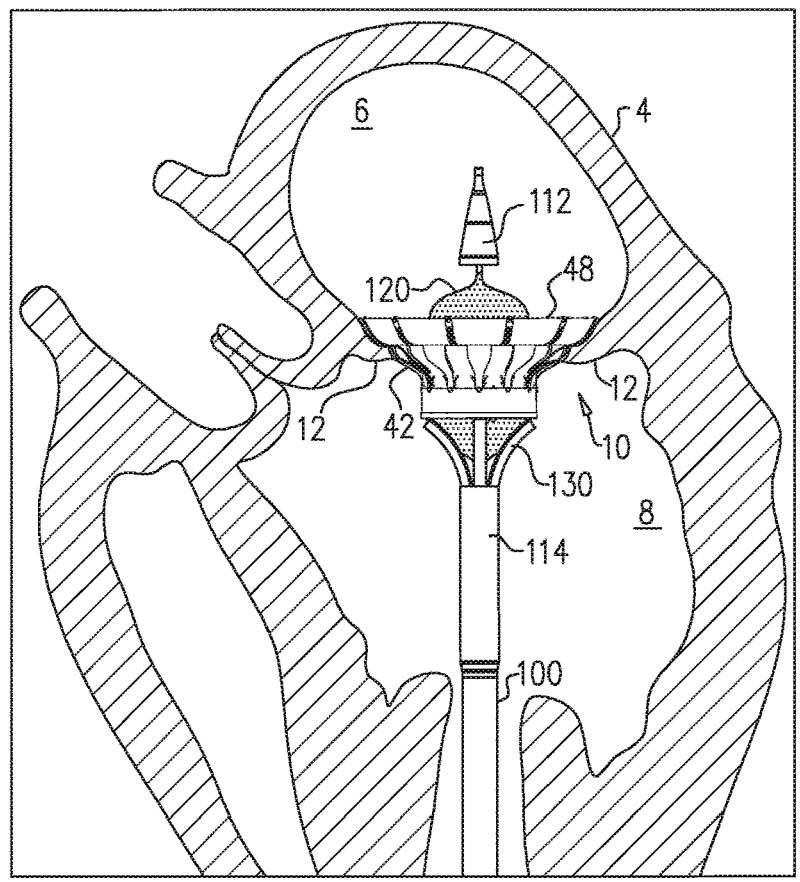

Subsequently, balloon 120 is further inflated to the further-inflated state further radially expanding tubular frame 30 (FIG. 7F). For some applications, this also further increases inter-flange distance D58 by expanding array 56. That is, further inflation of balloon 120 may enable the flanges to reach further laterally than when balloon 120 is in the partially-inflated state.

Figure 7G:
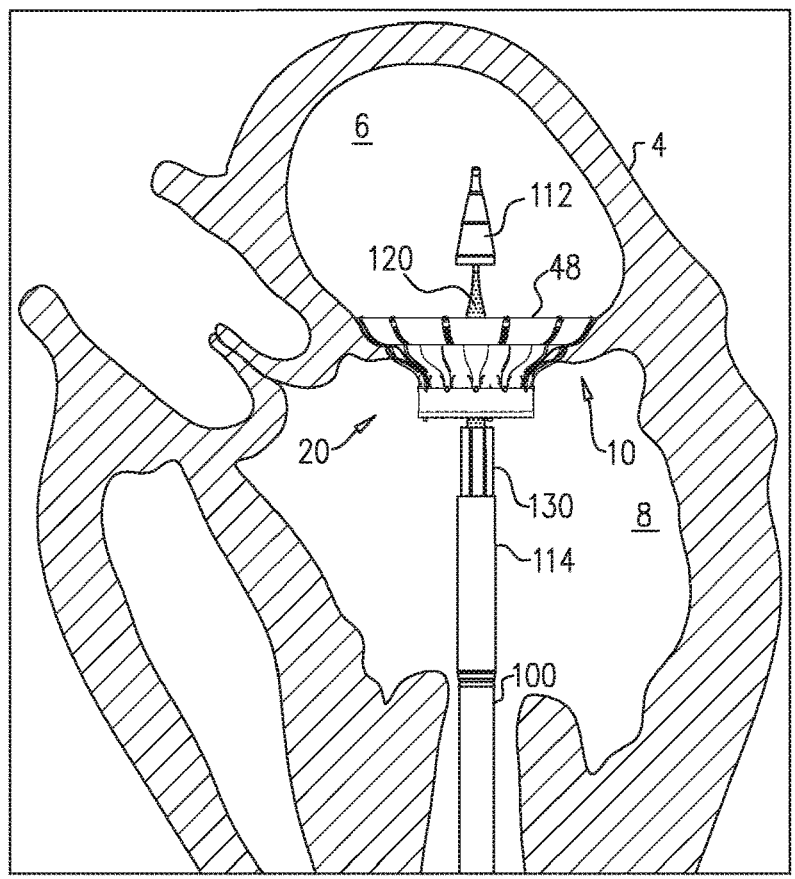
Figure 7H:
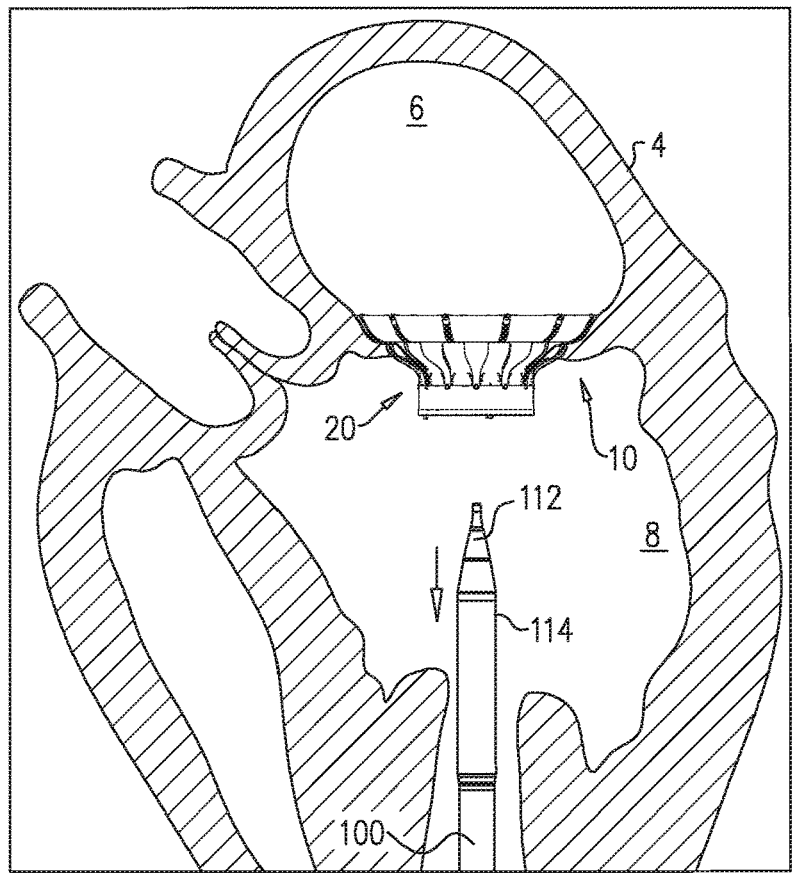

FIGS. 7G-H show subsequent deflation of balloon 120 and withdrawal of tool 100, e.g., analogous to FIGS. 3G-H, mutatis mutandis.

Figure 8A:
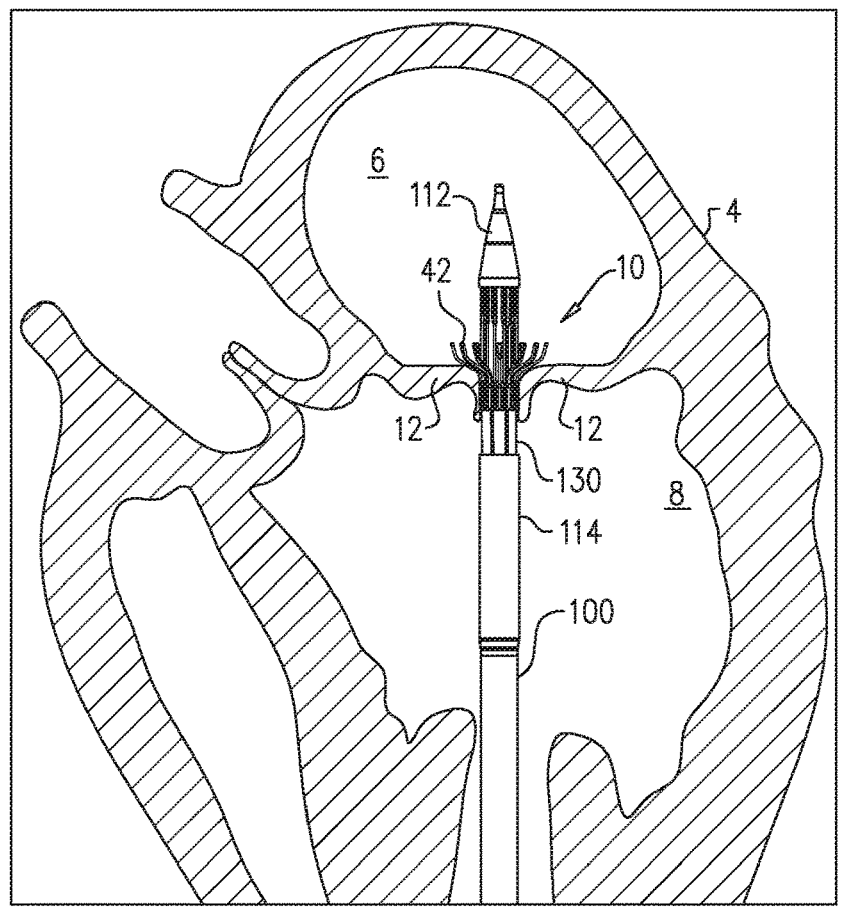
Figure 8B:
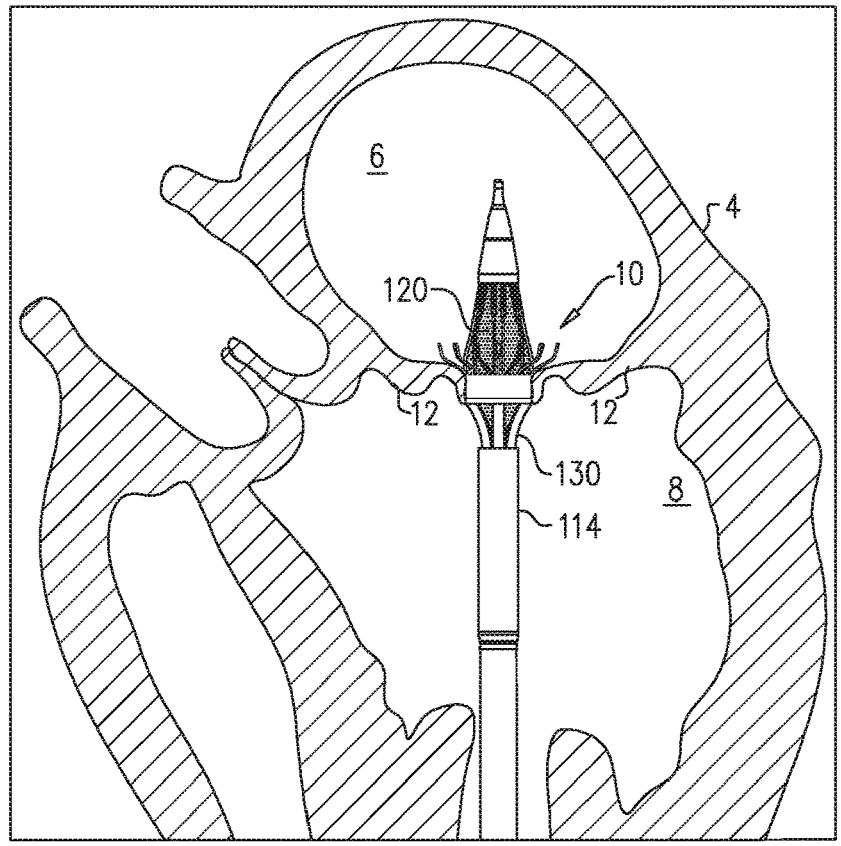
Figure 8C:
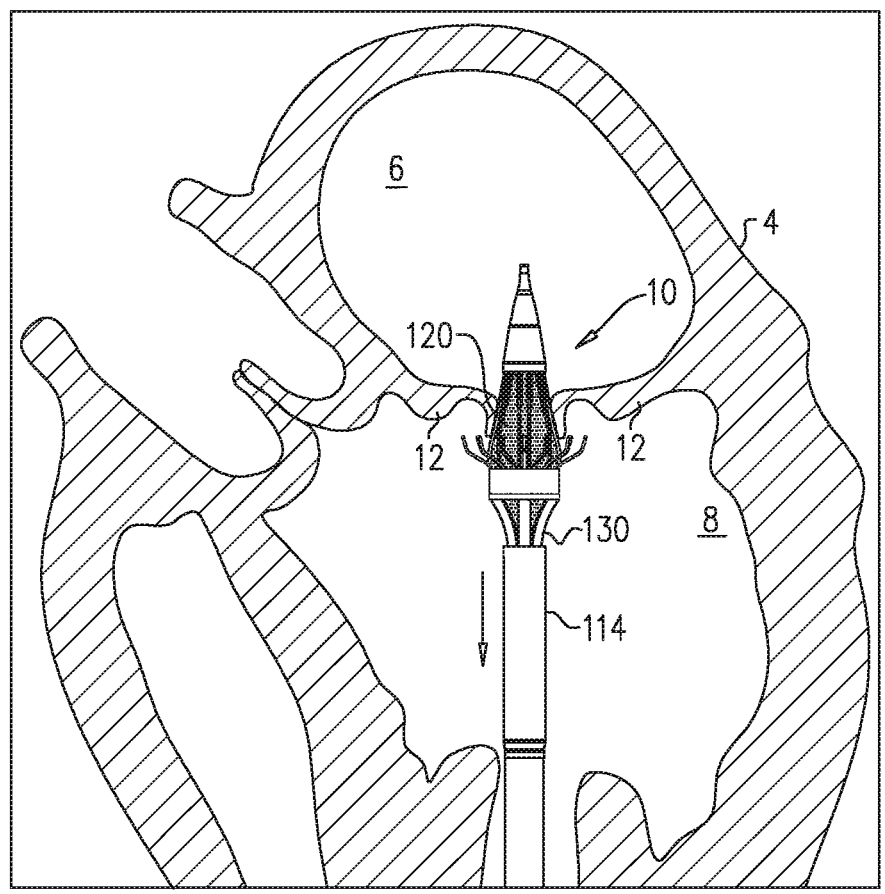

For some applications, it may be desirable to expose flanges 42 from capsule 110 and/or at least partially expand array 56, while the flanges are disposed upstream of the native valve 10 (e.g., within atrium 6), and to subsequently move the flanges downstream of the native valve (e.g., within ventricle 8) while the flanges remain in this state. FIGS. 8A-C relate to such applications.

FIG. 8A shows exposure of flanges disposed upstream of native valve 10, in accordance with some applications of the invention. Prior to this, tool 100 is typically positioned within the heart such that the flanges are disposed, within capsule 110, upstream of the native valve.

For some applications, and as shown in FIG. 8B, balloon 120 is then inflated to the partially-inflated state, while flanges 42 remain disposed upstream of native valve 10.

Subsequently, tool 100 is moved downstream (proximally, for a transapical approach) until the leaflets are observed (e.g., using fluoroscopy and/or ultrasound) to coapt upstream of flanges 42 (FIG. 8C). It is hypothesized by the inventors that this reduces how far downstream the flanges become disposed while deployed. That is, the position of implant 20 at which the leaflets coapt upstream of the flanges represents the minimal depth into the ventricle that the flanges are required to reach in order to subsequently ensnare the leaflets. This therefore reduces the distance that the deployed flanges must be moved in an upstream direction when subsequently engaging the leaflets. It is hypothesized by the inventors that this reduces the likelihood of inadvertently or prematurely ensnaring tissue such as chordae tendineae, which might otherwise occur if the deployed flanges were deeper within the ventricle, and therefore moved a greater distance, while in their deployed state, upstream through the ventricle. Similar techniques are described, mutatis mutandis, in US 2018/0014932 to Hammer et al. and WO 2016/125160 to Hariton et al. which are incorporated herein by reference.

For some applications in which flanges 42 are exposed upstream of the native valve, balloon 120 is partially inflated only after the exposed flanges are moved downstream of the native valve (embodiment not shown).

There is therefore provided, in accordance with some applications of the invention, method comprising:
  advancing, to the heart:
    a distal portion of a delivery tool, the delivery tool including:
      a shaft that extends to the distal portion of the delivery tool,
      a capsule disposed at the distal portion of the delivery tool, and
      a balloon, coupled to the shaft, and
    an implant disposed within the capsule, and including
      a tubular frame and an array of shape-memory flanges arranged around an outside of the tubular frame, the tubular frame compressed around the balloon, and the flanges constrained within the capsule;

subsequently, exposing the flanges from the capsule such that the flanges automatically deflect radially outward away from the tubular frame, and such that the array defines an inter-flange distance;

subsequently, by partially inflating the balloon to a partially-inflated state:
(i) partially radially expanding the tubular frame, and
(ii) partially increasing the inter-flange distance;

while the balloon remains in the partially-inflated state, pressing the flanges against a downstream surface of the native valve by moving the implant in an upstream direction; and subsequently, by further inflating the balloon to a further-inflated state, further radially expanding the tubular frame.

There is further provided, in accordance with some applications of the invention (e.g., as described in reference to FIGS. 8A-C) a method in which:

exposing the flanges comprises exposing the flanges while the flanges are positioned upstream of the native valve; and the method further comprises, prior to pressing the flanges against the downstream surface of the native valve, moving the exposed flanges to be downstream of the native valve.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for use at a native valve of a heart of a subject, the method comprising:
   advancing, to the heart:
     a distal portion of a delivery tool, the delivery tool including:
       a shaft that extends to the distal portion of the delivery tool,
       a capsule disposed at the distal portion of the delivery tool, and including an upstream capsule-portion and a downstream capsule-portion, and
       a balloon, coupled to the shaft, and disposed at least partly within the capsule, and
     an implant disposed within the capsule, and including a tubular frame and one or more shape-memory flanges, the tubular frame compressed around the balloon, and the flanges constrained within the downstream capsule-portion;
   exposing the flanges from the downstream capsule-portion such that the flanges automatically deflect radially outward;
   subsequently, pressing the flanges against a downstream surface of the native valve by moving the implant in an upstream direction; and
   while the flanges are in contact with the downstream surface, plastically expanding the tubular frame radially by inflating the balloon.

2. The method according to claim 1, wherein plastically expanding the tubular frame comprises plastically expanding the tubular frame by radially inflating the balloon while continuing to press the flanges against the downstream surface.

3. The method according to claim 1, wherein advancing the implant comprises advancing the implant while the tubular frame is disposed within the downstream capsule-portion, and the method further comprises exposing the tubular frame from the downstream capsule-portion.

4. The method according to claim 3, wherein exposing the tubular frame from the downstream capsule-portion comprises exposing the tubular frame entirely from the downstream capsule-portion without causing the tubular frame to expand.

5. The method according to claim 1, wherein the implant further includes a shape-memory upstream support portion, constrained within the upstream capsule-portion, and the method further comprises, prior to expanding the tubular frame, exposing the upstream support portion from the upstream capsule-portion such that the upstream support portion automatically deflects radially outward.

6. The method according to claim 1, wherein:
   the implant is compressed around a body balloon-portion of the balloon,
   the tool further includes one or more projections, each of the projections having a base-portion and a tip-portion,
   the projections extend, from the shaft, over at least a downstream balloon-portion of the balloon toward the tubular frame, such that the tip-portion of each of the projections is closer than its corresponding base-portion to the tubular frame, and
   pressing the flanges against the downstream surface by moving the implant in the upstream direction comprises pushing the implant in the upstream direction by pushing the tip-portions against the tubular frame.

7. The method according to claim 6, wherein expanding the tubular frame comprises inflating the balloon such that (i) the body balloon-portion radially expands the tubular frame by pressing radially outward against the tubular frame, and (ii) the downstream balloon-portion deflects the projections radially outward by pressing radially outward against the projections.

8. The method according to claim 6, wherein advancing the distal portion of the delivery tool comprises advancing the distal portion of the delivery tool while the projections are disposed within the downstream capsule-portion, and wherein the method further comprises, prior to radially expanding the tubular frame, exposing at least the tip-portions of the projections from the downstream capsule-portion.

9. The method according to claim 8, wherein exposing at least the tip-portions of the projections from the downstream capsule-portion comprises exposing at least the tip-portions of the projections from the downstream capsule-portion prior to pressing the flanges against the downstream surface of the native valve.

10. A method for use at a native valve of a heart of a subject, the method comprising:
    advancing, to the heart:
      a distal portion of a delivery tool, the delivery tool including:
        a shaft that extends to the distal portion of the delivery tool,
        a capsule disposed at the distal portion of the delivery tool, and
        a balloon, coupled to the shaft, and
      an implant disposed within the capsule, and including a tubular frame and an array of shape-memory flanges arranged around an outside of the tubular frame, the tubular frame compressed around the balloon, and the flanges constrained within the capsule;

subsequently, exposing the flanges from the capsule such that the flanges automatically deflect radially outward away from the tubular frame, and such that the array defines an inter-flange distance;

subsequently, by partially inflating the balloon to a partially-inflated state:
(i) partially radially expanding the tubular frame, and
(ii) partially increasing the inter-flange distance;

while the balloon remains in the partially-inflated state, pressing the flanges against a downstream surface of the native valve by moving the implant in an upstream direction; and subsequently, by further inflating the balloon to a further-inflated state, further radially expanding the tubular frame.

11. The method according to claim 10, wherein inflating the balloon to a further-inflated state further comprises increasing the inter-flange distance.

12. The method according to claim 10, wherein:
exposing the flanges comprises exposing the flanges while the flanges are positioned upstream of the native valve; and
the method further comprises, prior to pressing the flanges against the downstream surface of the native valve, moving the exposed flanges to be downstream of the native valve.

13. The method according to claim 12, wherein partially inflating the balloon comprises partially inflating the balloon while the flanges are positioned upstream of the native valve.

14. The method according to claim 10, wherein inflating the balloon to the further-inflated state comprises inflating the balloon to the further-inflated state while continuing to press the flanges against the downstream surface.

15. The method according to claim 10, wherein:
advancing the implant comprises advancing the implant while the tubular frame is disposed within a downstream capsule-portion of the capsule;
exposing the flanges from the capsule comprises moving the downstream capsule-portion of the capsule away from an upstream capsule-portion of the capsule; and
the method further comprises exposing the tubular frame from the downstream capsule-portion prior to pressing the flanges against the downstream surface of the native valve.

16. The method according to claim 10, wherein:
advancing the implant comprises advancing the implant while the tubular frame is disposed within a downstream capsule-portion of the capsule;
exposing the flanges from the capsule comprises moving the downstream capsule-portion of the capsule away from an upstream capsule-portion of the capsule; and
the method further comprises exposing the tubular frame from the downstream capsule-portion without causing the tubular frame to expand.

17. The method according to claim 10, wherein the implant further includes a shape-memory upstream support portion, constrained within the capsule, and the method further comprises, subsequent to pressing the flanges against a downstream surface of the native valve, exposing the upstream support portion from the capsule such that the upstream support portion automatically deflects radially outward.

18. The method according to claim 10, wherein:
advancing the implant disposed within the capsule, the tubular frame compressed around the balloon, comprises advancing the implant disposed within the capsule, the tubular frame compressed around a body balloon-portion of the balloon;
the distal portion of the delivery tool includes one or more projections, each of the projections having a base-portion and a tip-portion;
advancing the distal portion of the delivery tool comprises advancing the distal portion of the delivery tool while the one or more projections extend, from the shaft, over at least a downstream balloon-portion of the balloon toward the tubular frame, such that the tip-portion of each of the projections is closer than its corresponding base-portion to the tubular frame; and
pressing the flanges against the downstream surface by moving the implant in the upstream direction comprises pushing the implant in the upstream direction by pushing the tip-portions against the tubular frame.

19. The method according to claim 18, wherein inflating the balloon comprises inflating the balloon such that (i) the body balloon-portion radially expands the tubular frame by pressing radially outward against the tubular frame, and (ii) the downstream balloon-portion deflects the projections radially outward by pressing radially outward against the projections.

20. The method according to claim 18, wherein advancing the distal portion of the delivery tool comprises advancing the distal portion of the delivery tool while the projections are disposed within the capsule, and wherein the method further comprises, prior to partially radially expanding the tubular frame, exposing at least the tip-portions of the projections from the capsule.

* * * * *